(12) United States Patent
Narva et al.

(10) Patent No.: US 10,889,830 B2
(45) Date of Patent: Jan. 12, 2021

(54) BINARY INSECTICIDAL CRY TOXINS

(71) Applicant: Dow AgroSciences LLC, Indianapolis, IN (US)

(72) Inventors: Kenneth E. Narva, Zionsville, IN (US); Huarong Li, Zionsville, IN (US); Sek Yee Tan, Carmel, IN (US); Tao Xu, Indianapolis, IN (US); Timothy D. Hey, Zionsville, IN (US); Vimbai Chikwana, Indianapolis, IN (US); Sarah E. Worden, Indianapolis, IN (US)

(73) Assignee: DOW AGROSCIENCES LLC, Indianapolis, IN (US)

( * ) Notice: Subject to any disclaimer, the term of this patent is extended or adjusted under 35 U.S.C. 154(b) by 64 days.

(21) Appl. No.: 15/709,691

(22) Filed: Sep. 20, 2017

(65) Prior Publication Data

US 2018/0094277 A1  Apr. 5, 2018

Related U.S. Application Data

(60) Provisional application No. 62/402,316, filed on Sep. 30, 2016.

(51) Int. Cl.
| | |
|---|---|
| *C12N 15/82* | (2006.01) |
| *C07K 14/325* | (2006.01) |
| *C12N 9/00* | (2006.01) |
| *A01N 25/00* | (2006.01) |
| *A01N 63/10* | (2020.01) |

(52) U.S. Cl.
CPC ....... *C12N 15/8286* (2013.01); *A01N 25/006* (2013.01); *A01N 63/10* (2020.01); *C07K 14/325* (2013.01); *C12N 9/93* (2013.01); *C12N 15/8213* (2013.01); *G01N 2430/12* (2013.01); *Y02A 40/162* (2018.01)

(58) Field of Classification Search
CPC .................................................. C12N 15/8286

USPC ........................................................... 800/302
See application file for complete search history.

(56) References Cited

U.S. PATENT DOCUMENTS

| | | | |
|---|---|---|---|
| 10,433,557 | B2 | 10/2019 | Narva et al. |
| 2006/0205653 | A1* | 9/2006 | Larrinua ................ A01N 63/00 435/69.1 |
| 2008/0148432 | A1 | 6/2008 | Abad |
| 2009/0175974 | A1 | 7/2009 | Oppert et al. |
| 2011/0167514 | A1 | 7/2011 | Brover |
| 2015/0047076 | A1 | 2/2015 | Anderson |
| 2015/0274786 | A1 | 10/2015 | Bowen |

FOREIGN PATENT DOCUMENTS

| | | |
|---|---|---|
| WO | 2002077183 A2 | 10/2002 |
| WO | 2015059690 A1 | 4/2015 |
| WO | 2016144686 A1 | 9/2016 |

OTHER PUBLICATIONS

International Search Report, Written Opinion, and International Preliminary Report on Patentability for International Application PCT/US2017/052392 dated Feb. 13, 2018.
Pardo-Lopez, et al.; "Strategies to improve the insecticidal activity of Cry toxins from Bacillus thuringiensis"; Peptides (2009) 30:589-595.
EP Supplemental Search report dated Mar. 30, 2020.

\* cited by examiner

*Primary Examiner* — Li Zheng

(57) ABSTRACT

The subject invention concerns new classes of insecticidally-active proteins and the polynucleotide sequences which encode these proteins. More specifically, insecticidal proteins of approximately 12-24 kDa and of approximately 12-14 kDa are used for controlling corn rootworms. The subject invention includes methods and transgenic plants for controlling Western Corn Rootworm and other coleopteran insects.

6 Claims, 1 Drawing Sheet
Specification includes a Sequence Listing.

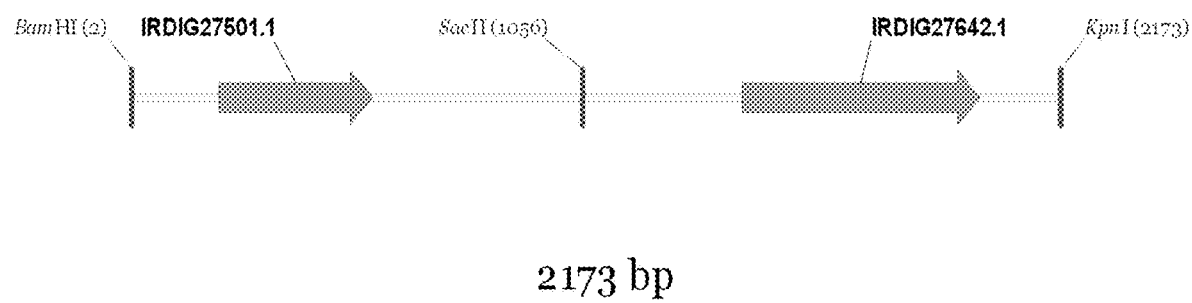

BINARY INSECTICIDAL CRY TOXINS

CROSS-REFERENCE TO RELATED APPLICATIONS

This Application claims priority from, and benefit of, U.S. Provisional Application 62/402,316 filed on Sep. 30, 2016. The entire contents of this application is hereby incorporated by reference into this application.

SEQUENCE IDENTIFICATION LISTING INCORPORATION

The official copy of the sequence listing is submitted electronically via EFS-Web as an ASCII formatted sequence listing with a file named "77990-US-NP_20170920_20170920Seq_ST25.txt", created on Aug. 30, 2017, and having a size of 83.8 KB, and is filed concurrently with the specification. The sequence listing contained in this ASCII formatted document is part of the specification, and is incorporated herein by reference in its entirety.

TECHNICAL FIELD

The present invention relates generally to the field of molecular biology as applied to agricultural sciences. More particularly, certain embodiments concern methods for the use of DNA segments as diagnostic probes and templates for protein production, and the use of proteins, fusion protein carriers and peptides for insect control and in various immunological and diagnostic applications. Also disclosed are methods of making and using nucleic acid segments in the development of plant-incorporated protectants in transgenic plant cells containing the DNA segments disclosed herein.

BACKGROUND

Billions of dollars are spent each year to control insect pests that plague agriculture. Additional billions are lost annually to the damage inflicted by these insect pests. Synthetic organic chemical insecticides have been the primary tools used to control insect pests but biological insecticides, such as insecticidal proteins derived from *Bacillus thuringiensis* (B.t.), have played an important role in some areas. The ability to produce insect-resistant plants by genetically transforming plant cells with B.t. insecticidal protein genes has revolutionized modern agriculture and heightened the importance and value of insecticidal proteins and their genes.

B.t. is a gram-positive bacterium that produces endotoxins known as crystal proteins, often referred to as Cry proteins or Cry toxins, which are selectively toxic to certain orders, genera, and species of insects. Many different strains of B.t. have been shown to produce insecticidal Cry proteins. Compositions including B.t. strains that produce insecticidal Cry proteins have been commercially available and used as environmentally acceptable insecticides.

The majority of insecticidal B.t. strains are active against insects of the order Lepidoptera, i.e., caterpillar insects. Other B.t. strains are insecticidally active against insects of the order Diptera, i.e., flies and mosquitoes, or against both lepidopteran and dipteran insects. In recent years, a few B.t. strains have been reported as producing crystal proteins that are toxic to insects of the order Coleoptera, i.e., beetles, such as corn rootworms. Such currently deployed toxic proteins include Cry3Bb1, a modified Cry3A, eCry3.1Ab, and a binary toxin Cry34Ab1/Cry35Ab1 (requiring two different proteins for toxic activity). These proteins are effective for controlling *Diabrotica* species that infest corn roots, whether deployed singly, or in various combinations to decrease the likelihood of the development of resistance. Even though these proteins have been successfully deployed as insect control agents in transgenic crop plants, resistance to their effects can develop.

The classification of these Cry proteins was previously based on their target insect types. Nomenclature is currently employed that systematically classifies the Cry genes based upon amino acid sequence homology rather than upon insect specificities (Crickmore, N. et al. Microbiol. and Mol. Bio. Rev. (1998) Vol. 62: 807-813).

The cloning and characterization of the gene for a 30-kDa toxin protein with activity on coleopteran and dipteran insects has been described (Intl. Pat. Appl. Pub. No. WO 95/02693, 1995). This gene, isolated from B.t. PS201T6, encodes a protein of 29,906 Da which exhibits a 64% sequence identity with the CytA toxin of B.t. var. *israelensis*.

Numerous B.t. proteins have been used as plant incorporated protectants to create insect-resistant transgenic plants that have been successfully registered, deregulated, and commercialized to date. An insecticidal protein system was discovered in B.t. and disclosed in WO 97/40162. This system comprises two proteins, one of approximately 14-15 kDa and the other of about 44-45 kDa. See also U.S. Pat. Nos. 6,083,499 and 6,127,180. These proteins have been assigned to the Cry designations of Cry34 and Cry35, respectively. Other related binary protein toxin systems have been disclosed. See U.S. Pat. No. 6,372,480; WO 01/14417; and WO 00/66742. Plant-optimized genes that encode such proteins, wherein the genes are engineered to use codons for optimized expression in plants, have also been disclosed. See U.S. Pat. No. 6,218,188.

Over 10 million acres of U.S. corn are infested with corn rootworm species complex each year. The corn rootworm species complex includes the northern corn rootworm (*Diabrotica barberi*), the southern corn rootworm (*D. undecimpunctata howardi*), and the western corn rootworm (*D. virgifera virgifera*). Other species include *Diabrotica virgifera zeae* (Mexican corn rootworm), *Diabrotica balteata* (Brazilian corn rootworm). The Brazilian corn rootworm complex includes *Diabrotica viridula* and *Diabrotica speciosa*.

The western corn rootworm (WCR, *Diabrotica virgifera virgifera* LeConte) is a significant maize pest throughout the U.S. corn-belt. WCR control has been a significant challenge due to resistance development against both chemical pesticides and transgenic plants expressing B.t. Cry toxins. WCR has developed significant resistance to Cry3Aa and Cry3Bb but not to Cry34/35 a binary protein pair that has been outstanding in the market. However, the Cry34/35 trait is under ever increasing selection pressure due to emergence of WCR Cry3-resistant populations.

Resistance to a deployed toxin, whether chemical or protein, is more likely to develop in a number of situations which enhance resistance development. Generally, the development of resistance is directly dependent on the length of time that a toxin is deployed into the environment. Resistance development is also more likely to increase in situations in which the dose of the toxin is insufficient to ensure mortality to the pest consuming a single bite of tissue containing the toxin. Accordingly, it is crucial to deliver a lethal dose of toxin with each bite; otherwise, development of resistance to a particular toxin is more likely to occur.

Repetitive use of the same toxin within a common geographic region on or in multiple species of plants which are susceptible to the same or similar pests within a common geographic region is more likely to cause rapid development of resistance to the toxin, particularly in climates in which there are multiple generations of a particular target pest within a single growing season. For all the forgoing reasons, dependence on a limited number of toxic proteins or toxic chemistries can result in the development of resistance to these pest control agents.

Other proteins disclosed in the art that are asserted to exhibit toxic effects to corn rootworms include patatin, TIC100/101 binary toxin, ET33/34 binary toxin, TIC863, ET80/76 binary toxin, ET70, Cry3Bb (U.S. Pat. No. 6,501,009), Cry1C variants, Cry3A variants, Cry3, Cry3B, Cry34/35, 5307, Axmi184, Axmi205, AxmiR1, TIC901, TIC1201, TIC407, TIC417, TIC431, TIC807, TIC853, TIC3131, DIG-10, eHIPs (U.S. Patent Application Publication No. 2010/0017914), and ω-Hex atoxin-Hv 1a (U.S. Patent Application Publication US2014-0366227 A1). These proteins may be provided alone or in combinations with other toxic agents in subsequent commercial embodiments to insure durability of the rootworm product and to decrease the likelihood of resistance development.

Despite the discovery of many selective protein toxins from B.t., there remains a critical need to discover new, effective pest control agents that provide economic benefits to farmers, are capable of delaying or preventing the development of resistant insects, and are environmentally acceptable. Particularly needed are agents targeted to control a wide spectrum of economically important insect pests that effectively control insect populations that are, or could become, resistant to existing insect control agents and those with equal to or increased potency compared to currently deployed insecticidal protein toxins.

SUMMARY OF THE INVENTION

The present invention relates in part to materials and methods for the control of coleopteran pests. In specific embodiments, the materials and methods described herein are used to control corn rootworm species. Plants that produce these protein toxins are included within the scope of the subject invention.

The present invention provides novel B.t. insecticidal protein binary toxins that are lethal or stunting when administered in combination to coleopteran pests. These binary toxins are comprised of a potentiator protein and a toxin protein. Some of the toxin proteins have lethal or sub-lethal properties when administered alone as describe in (78559 U.S. Prov Appl 62/319,428, filed Apr. 7, 2016). However all of the toxin proteins described herein are substantially more toxic when administered in binary form e.g. in combination with the potentiator protein.

The invention includes homologs, N-terminal deletions and extensions, derivatives, analogs, and mutant forms of these binary toxins, plant codon optimized nucleic acid sequences encoding the claimed binary toxins, methods for making and using the binary toxins and antibodies that selectively bind the binary toxins.

The subject invention includes polynucleotides which encode either of the insecticidal toxins, polynucleotides which encode portions or fragments of the full length toxins that retain pesticidal activity when used in combination, and polynucleotide sequences which encode both types of toxins. These binary toxins are active against coleopteran pests such as corn rootworm, and especially WCR.

In particular embodiments, the invention concerns isolated DNA segments and recombinant vectors incorporating DNA sequences that encode the claimed binary toxins. More preferably, the DNA segments comprise a nucleic acid sequence that encodes a protein or peptide species that includes within its amino acid sequence at least ten amino acid contiguous sequence of SEQ ID NOs:2, 4, 6, 8, 10, 12, 14, 16, 18, 20, 22, 24, 26, 63, 66, 68, 71, 74, 76, 78, 80, 82, 84, 86, 88, 91, 93, 95, 97, 99, 101, 103, and 105.

Similarly, a DNA segment comprising an isolated or purified protein-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes not only genomic sequences, including extrachromosomal DNA sequences, but also operon sequences or engineered gene segments that express, or may be adapted to express, proteins, polypeptides or peptides.

In a preferred embodiment, the subject invention concerns plants cells transformed with at least one polynucleotide sequence of the subject invention such that the transformed plant cells express pesticidal toxins in tissues consumed by the target pests.

Alternatively, the B.t. isolates of the subject invention, or recombinant microbes expressing the toxins described herein, can be used to control pests. In this regard, the invention includes the treatment of substantially intact B.t. cells, or recombinant cells containing the expressed toxins of the invention, treated to prolong the pesticidal activity when the substantially intact cells are applied to the environment of a target pest. The treated cell acts as a protective coating for the pesticidal toxin.

The toxins of the subject invention are oral intoxicants that affect the proper function an insect's midgut cells upon ingestion by the target insect. Exposing, administering or treating insects with these binary toxins means that the binary toxins enter the insect's digestive system most commonly by eating food containing such binary toxins. Thus, by consuming the binary toxins in any form or preferably in the form of recombinant plant cells expressing these toxins, the target insect is exposed to or contacts the protein toxins of the subject invention. Such contact or exposure to the binary toxins results in death, stunting or severe injury of the target pest.

The invention also is drawn to a method for controlling a coleopteran pest which comprises exposing the gut of said coleopteran pest to an effective combination of a potentiator protein and a toxin protein. The invention also is drawn to a nucleic acid construct for expression of a binary toxin comprising a genetic regulatory structure foreign to *Bacillus thuringiensis* and one or more binary toxin-encoding DNA segments. The invention further claims transgenic plants, plant parts, or seeds comprising a nucleic acid sequence encoding a binary toxin as well as compositions comprising formulated binary toxins. Also claimed is a method for producing a coleopteran-tolerant plant comprising breeding a non transgenic plant with a transgenic plant comprising a foreign DNA construct, capable of expressing a binary toxin, stably incorporated into the genome of the coleopteran-tolerant plant and selecting progeny by analyzing for at least a portion of the foreign DNA construct emanating from the transgenic plant.

BRIEF DESCRIPTION OF THE FIGURES

FIG. 1: Connection and orientation of IRDIG27501 and IRDIG27642 for co-expression in B.t.

BRIEF DESCRIPTION OF THE SEQUENCES

SEQ ID NO: 1 is a B.t. DNA sequence encoding IRDIG27501 potentiator protein; 357 nt.

SEQ ID NO:2 is the B.t. IRDIG27501 protein sequence, 118 aa.

SEQ ID NO:3 is a B.t. DNA sequence encoding IRDIG27642; 555 nt.

SEQ ID NO: 4 is the B.t. protein sequence of IRDIG27642; 184 aa.

SEQ ID NO:5 is a B.t. DNA sequence encoding IRDIG28672; 555 nt.

SEQ ID NO:6 is the B.t. protein sequence of IRDIG28672; 184 aa.

SEQ ID NO:7 is a B.t. DNA sequence encoding IRDIG28674; 555 nt.

SEQ ID NO:8 is the B.t. protein sequence of IRDIG28674; 184 aa.

SEQ ID NO:9 is a B.t. DNA sequence encoding IRDIG28676; 624 nt.

SEQ ID NO:10 is the B.t. protein sequence of IRDIG28676; 207 aa.

SEQ ID NO:11 is a B.t. DNA sequence encoding IRDIG28680; 333 nt.

SEQ ID NO:12 is the B.t. protein sequence of IRDIG28680; 110 aa.

SEQ ID NO:13 is a B.t. DNA sequence encoding IRDIG28682; 564 nt.

SEQ ID NO:14 is the B.t. protein sequence of IRDIG28682; 187 aa.

SEQ ID NO:15 is a B.t. DNA sequence encoding IRDIG28684; 564 nt.

SEQ ID NO:16 is the B.t. protein sequence of IRDIG28684; 187 aa.

SEQ ID NO:17 is a B.t. DNA sequence encoding IRDIG28686; 564 nt.

SEQ ID NO:18 is the B.t. protein sequence of IRDIG28686; 187 aa.

SEQ ID NO:19 is a B.t. DNA sequence encoding IRDIG28688; 570 nt.

SEQ ID NO:20 is the B.t. protein sequence of IRDIG28688; 189 aa.

SEQ ID NO:21 is a B.t. DNA sequence encoding IRDIG28690; 570 nt.

SEQ ID NO:22 is the B.t. protein sequence of IRDIG28690; 189 aa.

SEQ ID NO:23 is a B.t. DNA sequence encoding IRDIG28692; 579 nt.

SEQ ID NO:24 is the B.t. protein sequence of IRDIG28692; 192 aa.

SEQ ID NO:25 is a B.t. DNA sequence encoding IRDIG28694; 366 nt.

SEQ ID NO:26 is the B.t. protein sequence of IRDIG28694; 121 aa.

SEQ ID NOs:27 to 60 are primers used to amplify portions of the insecticidal proteins listed above.

SEQ ID NO:61 IRDIG27501 DNA codon optimized using the maize high GC (ZmHGC) strategy; 357 nt.

SEQ ID NO:62 IRDIG27501 DNA codon optimized using the maize highest GC (Zm Highest GC) strategy; 357 nt.

SEQ ID NO:63 IRDIG27501 protein; from codon optimized DNA sequence using the maize high GC (ZmHGC) strategy (protein for SEQ ID NOs:61-62); 118 aa.

SEQ ID NO:64 TraP4 fused to IRDIG27501 Zm Highest GC; 570 nt.

SEQ ID NO:65 TraP4 fused to IRDIG27501 ZmHGC; 570 nt.

SEQ ID NO:66 TraP4 fused to IRDIG27501 Zm Highest GC protein (protein for SEQ ID NOs:64-65); 189 aa.

SEQ ID NO:67 TraP8 IRDIG27501 ZmHGC; 555 nt.

SEQ ID NO:68 TraP8 IRDIG27501 ZmHGC protein; 184 aa.

SEQ ID NO:69 IRDIG27642 DNA codon optimized using the ZmHGC strategy; 555 nt.

SEQ ID NO:70 IRDIG27642 DNA codon optimized using the Zm Highest GC strategy; 555 nt.

SEQ ID NO:71 is the protein sequence from IRDIG27642; (protein for SEQ ID NOs:69-70); 184 aa.

SEQ ID NO:72 DNA codon optimized TraP8 fused to IRDIG27642 Zm Highest GC; 753 nt.

SEQ ID NO:73 DNA codon optimized TraP8 fused to IRDIG27642 Zm High GC; 753 nt.

SEQ ID NO:74 is the protein sequence from TraP8 fused to IRDIG27642 (protein for SEQ ID NOs:72-73); 250 aa.

SEQ ID NO:75 DNA codon optimized TraP4 fused to IRDIG27642 ZmHGC; 768 nt.

SEQ ID NO:76 is the protein sequence from TraP4 fused to IRDIG27642; 255 aa.

SEQ ID NO:77 IRDIG27501.2 and IRDIG27642.2 fused with a 2A sequence; 981 nt.

SEQ ID NO:78 is the protein sequences for IRDIG27501.2 and IRDIG27642.2 fused with a 2A sequence; 326 aa.

SEQ ID NO:79 IRDIG27642.2 and IRDIG27501.2 fused with a 2A sequence; 981 nt.

SEQ ID NO:80 is the protein sequence of IRDIG27642.2 and IRDIG27501.2 fused with a 2A sequence; 326 aa.

SEQ ID NO:81 is a truncated B.t. DNA of IRDIG27642.1, 324 nt.

SEQ ID NO:82 is a truncated B.t. protein for IRDIG27642.1; 107 aa.

SEQ ID NO:83 is a truncated B.t. DNA sequence from IRDIG27501; 297 nt.

SEQ ID NO:84 is a truncated B.t. protein sequence from IRDIG27501; 98 aa.

SEQ ID NO:85 is a truncated B.t. DNA sequence from IRDIG28674; 324 nt.

SEQ ID NO:86 is a truncated B.t. protein sequence from IRDIG28674; 107 aa.

SEQ ID NO:87 is a truncated B.t. DNA sequence from IRDIG28680; 327 nt.

SEQ ID NO:88 is a truncated B.t. protein sequence from IRDIG28680;

SEQ ID NO:89 is a truncated B.t. DNA sequence from IRDIG28682; 333 nt.

SEQ ID NO:90 is a truncated B.t. DNA sequence from IRDIG28688; 333 nt.

SEQ ID NO:91 is a truncated B.t. protein sequence from IRDIG28682 and IRDIG28688; 110 aa.

SEQ ID NO:92 is a truncated B.t. DNA sequence from IRDIG28684; 333 nt.

SEQ ID NO:93 is a truncated B.t. protein sequence from IRDIG28684; 110 aa.

SEQ ID NO:94 is a truncated B.t. DNA sequence from IRDIG28686; 333 nt.

SEQ ID NO:95 is a truncated B.t. protein sequence from IRDIG28686; 110 aa.

SEQ ID NO:96 is a truncated B.t. DNA sequence from IRDIG28672; 324 nt.

SEQ ID NO:97 is a truncated B.t. protein sequence from IRDIG28672; 108 aa.

SEQ ID NO:98 is a truncated B.t. DNA sequence from IRDIG28676; 342 nt.

SEQ ID NO:99 is a truncated B.t. protein sequence from IRDIG28676; 113 aa.

SEQ ID NO:100 is a truncated B.t. DNA sequence from IRDIG28690; 333 nt.

SEQ ID NO: 101 is a truncated B.t. protein sequence from IRDIG28690; 110 aa.

SEQ ID NO:102 is a truncated B.t. DNA sequence from IRDIG28692; 348 nt.

SEQ ID NO: 103 is a truncated B.t. protein sequence from IRDIG28692; 115 aa.

SEQ ID NO:104 is a truncated B.t. DNA sequence from IRDIG28694; 273 nt.

SEQ ID NO:105 is a truncated B.t. protein sequence from IRDIG28694; 90 aa.

DETAILED DESCRIPTION OF THE INVENTION

The following words and phrases have the meanings set forth below. Unless specifically indicated, the terms "a", "an", and "the" signify "at least one" as used herein.

"An insecticidal protein" that may also be referred to as a "toxin protein" is defined as SEQ ID NOs:4, 6, 8, 10, 12, 14, 16, 18, 20, 22, 24, 26, 63, 66, 68, 71, 74, 76, 78, 80, 82, 84, 86, 88, 91, 93, 95, 97, 99, 101, 103, 105, and protein toxins have at least 70% sequence identity with any of the foregoing including derivatives, analogs, and mutant forms. A more preferred group of insecticidal proteins consists of SEQ ID NOs:4, 6, 8, 10, 12, 14, 16, 18, 20, 22, 24, 26, 63, 66, 68, 71, 74, 76, 78, 80, 82, 84, 86, 88, 91, 93, 95, 97, 99, 101, 103, 105, and protein toxins have at least 80% sequence identity with any of the foregoing sequences. Another preferred group of insecticidal proteins consists of SEQ ID NOs:4, 6, 8, 10, 12, 14, 16, 18, 20, 22, 24, 26, 63, 66, 68, 71, 74, 76, 78, 80, 82, 84, 86, 88, 91, 93, 95, 97, 99, 101, 103, 105, and protein toxins have at least 90% sequence identity with any of the foregoing sequences. Another preferred group of insecticidal proteins consists of SEQ ID NOs:4, 6, 8, 10, 12, 14, 16, 18, 20, 22, 24, 26, 63, 66, 68, 71, 74, 76, 78, 80, 82, 84, 86, 88, 91, 93, 95, 97, 99, 101, 103, 105, and protein toxins have at least 95% sequence identity with any of the foregoing sequences. Another preferred group of insecticidal proteins consists of SEQ ID NOs:4, 6, 8, 10, 12, 14, 16, 18, 20, 22, 24, 26, 63, 66, 68, 71, 74, 76, 78, 80, 82, 84, 86, 88, 91, 93, 95, 97, 99, 101, 103, 105, and protein toxins have at least 99% sequence identity with any of the foregoing sequences. The most preferred group of insecticidal proteins consists of SEQ ID NOs:4, 6, 8, 10, 12, 14, 16, 18, 20, 22, 24, 26, 63, 66, 68, 71, 74, 76, 78, 80, 82, 84, 86, 88, 91, 93, 95, 97, 99, 101, 103, and 105.

"A potentiator protein" is defined as SEQ ID NO:2 or any functional amino acid sequence comprising SEQ ID NO:2. Potentiator proteins further include any functional amino acid sequences having at least 70% sequence identity to SEQ ID NO:2. A more preferred group of potentiator proteins consists of any functional amino acid sequences having at least 80% sequence identity to SEQ ID NO:2 Another preferred group of potentiator proteins consists of any functional amino acid sequences having at least 90% sequence identity to SEQ ID NO:2 Another preferred group of potentiator proteins consists of any functional amino acid sequences having at least 95% sequence identity to SEQ ID NO:2 Another preferred group of potentiator proteins consists of any functional amino acid sequences having at least 99% sequence identity to SEQ ID NO:2. The most preferred potentiator protein is SEQ ID NO:2.

"DNA segment" refers to a DNA molecule that has been isolated free of total genomic DNA of a particular species. Therefore, a DNA segment encoding a protein or peptide refers to a DNA segment that contains protein coding sequences yet is isolated away from, or purified free from, total genomic DNA of the species from which the DNA segment is obtained, which in the instant case is the genome of the Gram-positive bacterial genus, *Bacillus*, and in particular, the species known as B.t. Included within the term "DNA segment", are DNA segments and smaller fragments of such segments, and also recombinant vectors, including, for example, plasmids, cosmids, phagemids, phage, viruses, and the like.

"Isolated substantially away from other coding sequences" means that the gene of interest, in this case, a gene encoding a bacterial insecticidal protein, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

"Expression" is defined as the combination of intracellular processes, including transcription and translation, undergone by a coding DNA molecule such as a structural gene to produce polypeptide.

By the use of the term "genetic material" herein, it is meant to include all genes, nucleic acid, DNA and RNA. The term "dsRNA" refers to double-stranded RNA. For designations of nucleotide residues of polynucleotides, DNA, RNA, oligonucleotides, and primers, and for designations of amino acid residues of proteins, standard IUPAC abbreviations are employed throughout this document. Nucleic acid sequences are presented in the standard 5' to 3' direction, and protein sequences are presented in the standard amino (N) terminal to carboxy (C) terminal direction.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a fertile plant from a plant cell (e.g., plant protoplast or explant).

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose genome has been altered by the introduction of an exogenous DNA molecule into that cell.

Transgenic cell: Any cell derived or regenerated from a transformed cell or derived from a transformed cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and to which another DNA segment can be operatively linked so as to bring about replication of the attached segment. A plasmid is an exemplary vector.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding the whole or a portion of the peptide sequence disclosed in SEQ ID NOs:2, 4, 6, 8, 10, 12, 14, 16, 18, 20, 22, 24, 26, 63, 66, 68, 71, 74, 76, 78, 80, 82, 84, 86, 88, 91, 93, 95, 97, 99, 101, 103, 105, or that are identical to or complementary to DNA sequences which encode the peptide disclosed in SEQ ID NOs:2, 4, 6, 8, 10, 12, 14, 16, 18, 20, 22, 24, 26, 63, 66, 68, 71, 74, 76, 78, 80, 82, 84, 86, 88, 91, 93, 95, 97, 99, 101, 103, 105, and particularly the DNA segment disclosed in SEQ ID NOs:1, 3, 5, 7, 9, 11, 13, 15, 17, 19, 21, 23, 25, 61, 62, 64, 65, 67, 69, 70, 72, 73, 75, 77, 79, 81, 83, 85, 87, 89, 90, 92, 94, 96, 98, 100, 102, and 104. For example, DNA sequences such as about 14 nucleotides, and that are up to about 10,000, about 5,000, about 3,000, about 2,000, about 1,000, about 500, about 200, about 100, about 50, and about 14 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200-500; 500-1,000; 1,000-2,000; 2,000-3,000; 3,000-5,000; and up to and including sequences of about 10,000 nucleotides and the like.

It will also be understood that this invention is not limited to the particular nucleic acid sequences which encode peptides of the present invention, or which encode the amino acid sequence of SEQ ID NOs:2, 4, 6, 8, 10, 12, 14, 16, 18, 20, 22, 24, 26, 63, 66, 68, 71, 74, 76, 78, 80, 82, 84, 86, 88, 91, 93, 95, 97, 99, 101, 103, 105, including the DNA sequence which is particularly disclosed in SEQ ID NOs:1, 3, 5, 7, 9, 11, 13, 15, 17, 19, 21, 23, 25, 61, 62, 64, 65, 67, 69, 70, 72, 73, 75, 77, 79, 81, 83, 85, 87, 89, 90, 92, 94, 96, 98, 100, 102, and 104. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The insecticidal protein-encoding gene encodes the insecticidal protein having an amino acid sequence and size shown in Table 1.

TABLE 1

Insecticidal gene and protein SEQ ID NOs and insecticidal protein size

| Name | Gene SEQ ID NO | Protein SEQ ID NO | Predicted Protein Size (kDa) |
| --- | --- | --- | --- |
| IRDIG27501 | 1 | 2 | 12.7 |
| IRDIG27642 | 3 | 4 | 21.1 |
| IRDIG28672 | 5 | 6 | 21.1 |
| IRDIG28674 | 7 | 8 | 20.9 |
| IRDIG28676 | 9 | 10 | 23.7 |
| IRDIG28680 | 11 | 12 | 12.3 |
| IRDIG28682 | 13 | 14 | 21.6 |
| IRDIG28684 | 15 | 16 | 21.5 |
| IRDIG28686 | 17 | 18 | 21.6 |
| IRDIG28688 | 19 | 20 | 21.8 |
| IRDIG28690 | 21 | 22 | 21.9 |
| IRDIG28692 | 23 | 24 | 22 |
| IRDIG28694 | 25 | 26 | 13.6 |

The DNA segments of the present invention encompass biologically-functional, equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level. Fragments and equivalents which retain the pesticidal activity of the exemplified toxins would be within the scope of the subject invention. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR technology, in connection with the compositions disclosed herein.

In addition to their use in directing the expression of insecticidal proteins or peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NOs:1, 3, 5, 7, 9, 11, 13, 15, 17, 19, 21, 23, 25, 61, 62, 64, 65, 67, 69, 70, 72, 73, 75, 77, 79, 81, 83, 85, 87, 89, 90, 92, 94, 96, 98, 100, 102, and 104 will find particular utility. Longer contiguous identical or complementary sequences, e.g., those of about 20, 30, 40, 50, 100, 200, 500, 1000, 2000, 5000, 10000 etc. (including all intermediate lengths and up to and including full-length sequences) will also be of use in certain embodiments.

The ability of such nucleic acid probes to specifically hybridize to protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10-14, 15-20, 30, 50, or even of 100-200 nucleotides or so, identical or complementary to the DNA sequence of SEQ ID NOs:1, 3, 5, 7, 9, 11, 13, 15, 17, 19, 21, 23, 25, 61, 62, 64, 65, 67, 69, 70, 72, 73, 75, 77, 79, 81, 83, 85, 87, 89, 90, 92, 94, 96, 98, 100, 102, or 104, are particularly contemplated as hybridization probes for use in, e.g., Southern and Northern blotting. Smaller fragments will generally find use in hybridization embodiments, wherein the length of the contiguous complementary region may be varied, such as between about 10-14 and about 100 or 200 nucleotides, but larger contiguous complementary stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Toxins and genes of the subject invention can be identified and obtained by using oligonucleotide probes, for example, these probes are detectable nucleotide sequences. The probes (and the polynucleotides of the subject invention) may be DNA, RNA, or PNA (peptide nucleic acid). These sequences may be detectable by virtue of an appropriate label or may be made inherently fluorescent as described in International Application No. WO93/16094. Depending on the application envisioned, one will desire to employ varying conditions of hybridization to achieve varying degrees of selectivity of probe towards target sequence. Typically, stringent conditions will be those in which the salt concentration is less than about 1.5 M Na ion, typically about 0.01 to 1.0 M Na ion concentration (or other salts) at pH 7.0 to pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. Optionally, wash buffers may comprise about 0.1% to about 1% SDS. Duration of hybridization is generally less than about 24 hours, usually about 4 to about 12 hours. Such selective conditions tolerate little, if any, mismatch between the probe and the template or target strand, and would be particularly suitable for isolating protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses.

Specificity is typically the function of post-hybridization washes, the critical factors being the ionic strength and temperature of the final wash solution. For DNA/DNA hybrids, the thermal melting point ($T_m$) is the temperature (under defined ionic strength and pH) at which 50% of a complementary target sequence hybridizes to a perfectly matched probe. $T_m$ is reduced by about 1° C. for each 1% of mismatching; thus, $T_m$, hybridization conditions, and/or wash conditions can be adjusted to facilitate annealing of sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, highly stringent conditions can utilize a hybridization and/or wash at 1° C., 2° C., 3° C., or 4° C. lower than the $T_m$; moderately stringent conditions can utilize a hybridization and/or wash at 6° C., 7° C., 8° C., 9° C., or 10° C. lower than the $T_m$, and low stringency conditions can utilize a hybridization and/or wash at 11° C., 12° C., 13° C., 14° C., 15° C., or 20° C. lower than the $T_m$.

$T_m$ (in ° C.) may be experimentally determined or may be approximated by calculation. For DNA-DNA hybrids, the $T_m$ can be approximated from the equation:

$$T_m(°\text{C.})=81.5°\text{C.}+16.6(\log M)+0.41(\% \text{ GC})-0.61(\% \text{ formamide})-500/L;$$

where M is the molarity of monovalent cations, % GC is the percentage of guanosine and cytosine nucleotides in the DNA, % formamide is the percentage of formamide in the hybridization solution (w/v), and L is the length of the hybrid in base pairs.

Alternatively, the $T_m$ is described by the following formula (Beltz et al., 1983).

$$T_m(°\text{C.})=81.5°\text{C.}+16.6(\log [\text{Na+}])+0.41(\% \text{ GC})-0.61(\% \text{ formamide})-600/L$$

where [Na+] is the molarity of sodium ions, % GC is the percentage of guanosine and cytosine nucleotides in the DNA, % formamide is the percentage of formamide in the hybridization solution (w:v), and L is the length of the hybrid in base pairs.

Using the equations, hybridization and wash compositions, and desired $T_m$, those of ordinary skill will understand that variations in the stringency of hybridization and wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993). Also see Sambrook et al. (1989).

Of course, for some applications, for example, where one desires to prepare mutants employing a mutant primer strand hybridized to an underlying template or where one seeks to isolate protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

In preferred embodiments, the insecticidal proteins are used together, and the proteins are pesticidal in combination. Thus, the two classes of proteins of the subject invention can be referred to as "binary toxins." As used herein, the term "toxin" includes either class of pesticidal proteins. The subject invention concerns polynucleotides which encode either insecticidal toxin, polynucleotides which encode portions or fragments of the full length toxins that retain pesticidal activity when used in combination, and polynucleotide sequences which encode both types of toxins. In a preferred embodiment, these toxins are active against coleopteran pests, more preferably corn rootworm, and most preferably Western corn rootworm.

Certain specific toxins are exemplified herein. For toxins having a known amino acid sequence, the molecular weight is also known. Those skilled in the art will recognize that the apparent molecular weight of a protein as determined by gel electrophoresis will sometimes differ from the true molecular weight. Therefore, reference herein to, for example, a 21 kDa protein or a 12 kDa protein is understood to refer to proteins of approximately that size even if the true molecular weight is somewhat different.

The subject invention concerns not only the polynucleotide sequences which encode these classes of toxins, but also the use of these polynucleotide sequences to produce recombinant hosts which express the toxins. In a further aspect, the subject invention concerns the combined use of an insecticidal toxin of the subject invention together with an additional insecticidal toxin of the subject invention to achieve highly effective control of pests, including coleopterans such as corn rootworm.

Thus, control of coleopterans, including corn rootworm using the isolates, toxins, and genes of the subject invention can be accomplished by a variety of methods known to those skilled in the art. These methods include, for example, the application of B.t. isolates to the pests (or their location), the application of recombinant microbes to the pests (or their locations), and the transformation of plants with genes which encode the pesticidal toxins of the subject invention.

Recombinant microbes may be, for example, a B.t., *E. coli*, or *Pseudomonas*. Transformations can be made by those skilled in the art using standard techniques. Materials necessary for these transformations are disclosed herein or are otherwise readily available to the skilled artisan.

The new classes of toxins and polynucleotide sequences provided here are defined according to several parameters. One critical characteristic of the toxins described herein is pesticidal activity. In a specific embodiment, these toxins have activity against coleopteran pests. The toxins and genes of the subject invention can be further defined by their amino acid and nucleotide sequences. The sequences of the molecules within each novel class can be defined herein in terms of homology to certain exemplified sequences as well as in terms of the ability to hybridize with, or be amplified by, certain probes and primers. The classes of toxins provided herein can also be identified based on their immunoreactivity with certain antibodies and based upon their adherence to a generic formula.

It should be apparent to a person skilled in this art that genes encoding binary toxins according to the subject invention can be identified and obtained through several means. These genes, and toxins, of the subject invention can be constructed synthetically.

With the teachings provided herein, one skilled in the art could readily produce and use the various toxins and polynucleotide sequences of the novel classes described herein.

Other isolates of the subject invention can also be characterized in terms of the shape and location of toxin inclusions.

In a preferred embodiment, the toxins of the subject invention have at least one of the following characteristics:

(a) said toxin is encoded by a nucleotide sequence which hybridizes under stringent conditions with a nucleotide sequence selected from the group consisting of: DNA which encodes SEQ ID NO:4, DNA which encodes SEQ ID NO:6, DNA which encodes SEQ ID NO:8, DNA which encodes SEQ ID NO: 10, DNA which encodes SEQ ID NO: 12, DNA which encodes SEQ ID NO:14, DNA which encodes SEQ ID NO:16, DNA which encodes SEQ ID NO:18, DNA which encodes SEQ ID NO:20, DNA which encodes SEQ ID NO:22, DNA which encodes SEQ ID NO:24, DNA which encodes SEQ ID NO:26, DNA which encodes SEQ ID NO:71, DNA which encodes SEQ ID NO:74, DNA which encodes SEQ ID NO:76, DNA which encodes SEQ ID NO:78, DNA which encodes SEQ ID NO:80, DNA which encodes SEQ ID NO:82, DNA which encodes SEQ ID NO:84, DNA which encodes SEQ ID NO:86, DNA which encodes SEQ ID NO:88, DNA which encodes SEQ ID NO:91, DNA which encodes SEQ ID NO:93, DNA which encodes SEQ ID NO:95, DNA which encodes SEQ ID NO:97, DNA which encodes SEQ ID NO:99, DNA which encodes SEQ ID NO:101, DNA which encodes SEQ ID NO:103, and DNA which encodes SEQ ID NO:105;

(b) said toxin is encoded by a nucleotide sequence wherein a portion of said nucleotide sequence can be amplified by PCR using a primer pair selected from the group consisting of those listed in Table 4;

(c) said toxin comprises a pesticidal portion of the amino acid sequence shown in SEQ ID NOs:4, 6, 8, 10, 12, 14, 16, 18, 20, 22, 24, 26, 71, 74, 76, 78, 80, 82, 84, 86, 88, 91, 93, 95, 97, 99, 101, 103, or 105;

(d) said toxin comprises an amino acid sequence which has at least about 60% homology with a pesticidal portion of an amino acid sequence selected from the group consisting of SEQ ID NOs:4, 6, 8, 10, 12, 14, 16, 18, 20, 22, 24, 26, 71, 74, 76, 78, 80, 82, 84, 86, 88, 91, 93, 95, 97, 99, 101, 103, 105;

(e) said toxin is encoded by a nucleotide sequence which hybridizes under stringent conditions with a nucleotide sequence selected from the group consisting of DNA which encodes SEQ ID NOs:4, 6, 8, 10, 12, 14, 16, 18, 20, 22, 24, 26, 71, 74, 76, 78, 80, 82, 84, 86, 88, 91, 93, 95, 97, 99, 101, 103, 105;

(f) said toxin is encoded by a nucleotide sequence wherein a portion of said nucleotide sequence can be amplified by PCR using the primer pairs listed in Table 4; and (h) said toxin comprises an amino acid sequence which has at least about 60% homology with an amino acid sequence selected from the group consisting of SEQ ID NO:2, SEQ ID NO:63, SEQ ID NO:66, and SEQ ID NO:68.

Modification of Genes and Toxins. The genes and toxins useful according to the subject invention include not only the specifically exemplified full-length sequences, but also portions (including internal deletions compared to the full-length proteins), fragments (including terminal deletions compared to the full-length protein) of these sequences, variants, mutants, chimeric, and fusion proteins, including proteins having substituted amino acids, which retain the characteristic pesticidal activity of the proteins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

Variations of genes may be readily constructed using standard techniques for making point mutations, for example. Also, U.S. Pat. No. 5,605,793, for example, describes methods for generating additional molecular diversity by using DNA reassembly after random fragmentation. Fragments of full-length genes can be made using commercially available exonucleases or endonucleases according to standard procedures. For example, enzymes such as Ba131 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other B.t. toxins. These antibodies can then be used to specifically identify equivalent toxins with the characteristic activity by immunoprecipitation, enzyme linked immunosorbent assay (ELISA), or western blotting. Antibodies to the toxins disclosed herein, or to equivalent toxins, or fragments of these toxins, can readily be prepared using standard procedures in this art. The genes which encode these toxins can then be obtained from the microorganism.

Synthetic genes which are functionally equivalent to the toxins of the subject invention can also be used to transform hosts. Methods for the production of synthetic genes can be found in, for example, U.S. Pat. No. 5,380,831.

The invention also discloses and claims a composition comprising an insecticidal protein. The composition may comprise bacterial host cells which express an insecticidal protein, in the soluble fraction, inclusion bodies or crystals containing the insecticidal protein, culture supernatant, disrupted cells, cell extracts, lysates, homogenates, and the like. The compositions may be in aqueous form, or alternatively, in dry, semi-wet, or similar forms such as cell paste, cell pellets, or alternatively freeze dried, powdered, lyophilized, evaporated, or otherwise similarly prepared in dry form. Such means for preparing insecticidal proteins are well-known to those of skill in the art of bacterial protein isolation and purification. In certain embodiments, the proteins may be purified, concentrated, admixed with other reagents, or processed to a desired final form. Preferably, the composition will comprise from about 1% to about 90% by weight of the protein, and more preferably from about 5%, to about 50% by weight.

In a preferred embodiment, the protein compositions of the invention may be prepared by a process which comprises the steps of culturing a *Bacillus thuringiensis* cell which expresses an insecticidal protein under conditions effective to produce such a protein, and then obtaining the protein from the cell. The obtaining of such a protein may further include purifying, concentrating, processing, or mixing the protein with one or more reagents. Preferably, the insecticidal protein toxin is obtained in an amount of from between about 1% to about 90% by weight and more preferably from about 5% to about 50% by weight.

The invention also relates to a method of preparing an insecticidal protein composition. Such a method generally involves the steps of culturing a *Bacillus thuringiensis* cell which expresses an insecticidal protein toxin under conditions effective to produce the protein, and then obtaining the protein so produced. In a preferred embodiment the *Bacillus thuringiensis* cell is any *Bacillus thuringiensis* cell which contains an insecticidal protein gene segment. Alternatively, the recombinant plasmid vectors of the invention may be used to transform other suitable bacterial or eukaryotic cells to produce the protein of the invention. Prokaryotic host cells including Gram-negative cells such as *E. coli*, *Pseudomonas fluorescens* and related Enterobacteraceae, or Gram-positive cells such as *Bacillus* spp. (including *B. megaterium*, *B. subtilis*, and B.t.) and the like are all contemplated to be useful in the preparation of the insecticidal proteins of the invention. Particularly preferred are the commonly used *E. coli* expression strains.

In such embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the *Pichia* expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of peptides or epitopic core regions, such as may be used to generate anti-protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from SEQ ID NOs:2, 4, 6, 8, 10, 12, 14, 16, 18, 20, 22, 24, 26, 63, 66, 68, 71, 74, 76, 78, 80, 82, 84, 86, 88, 91, 93, 95, 97, 99, 101, 103, or 105.

In yet another aspect, the present invention provides methods for producing a transgenic cell, and in particular a plant or animal cell which expresses a nucleic acid segment encoding the novel insecticidal proteins of the present invention. The process of producing transgenic cells is well-known in the art. In general, the method comprises transforming a suitable host cell with a DNA segment which contains a promoter operatively linked to a coding region that encodes an insecticidal protein toxin. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant protein expressed in a particular transgenic cell, the invention also provides for the expression of protein antisense mRNA. The use of antisense mRNA as a means of controlling or decreasing the amount of a given protein of interest in a cell is well-known in the art.

In a preferred embodiment, the invention encompasses a plant cell which has been transformed with a nucleic acid segment of the invention, and which expresses a gene or gene segment encoding one or more of the novel polypeptide compositions disclosed herein. As used herein, the term "transgenic plant cell" is intended to refer to a plant cell that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of an insecticidal protein toxin-expressing transgene. In some instances, more than one transgene will be incorporated into the genome of the transformed host plant cell. Such is the case when more than one protein-encoding DNA segment is incorporated into the genome of such a plant. In certain situations, it may be desirable to have one, two, three, four, or even more B.t. crystal proteins (either native or recombinantly-engineered) incorporated and stably expressed in the transformed transgenic plant. In preferred embodiments, the introduction of the transgene into the genome of the plant cell results in a stable integration wherein the offspring of such plants also contain a copy of the transgene in their genome. The inheritability of this genetic element by the progeny of the plant into which the gene was originally introduced is a preferred aspect of this invention.

A preferred gene which may be introduced includes, for example, a protein-encoding a DNA sequence from bacterial origin, and particularly one or more of those described herein which are obtained from *Bacillus* spp. Highly preferred nucleic acid sequences are those obtained from B.t., or any of those sequences which have been genetically engineered to decrease or increase the insecticidal activity of the protein in such a transformed host cell.

Means for transforming a plant cell and the preparation of a transgenic cell line are well-known in the art (as exemplified in U.S. Pat. Nos. 5,550,318; 5,508,468; 5,482,852;

5,384,253; 5,276,269; and 5,225,341, all specifically incorporated herein by reference), and are briefly discussed herein. Vectors, plasmids, cosmids, YACs (yeast artificial chromosomes), and DNA segments for use in transforming such cells will, of course, generally comprise either the operons, genes, or gene-derived sequences of the present invention, either native, or synthetically-derived, and particularly those encoding the disclosed proteins. These DNA or nucleic acid constructs can further include regulatory structures such as promoters, enhancers, polylinkers, or even gene sequences which have positively- or negatively-regulating activity upon the particular genes of interest as desired. The DNA segment or gene may encode either a native or modified protein, which will be expressed in the resultant recombinant cells, and/or which will impart an improved phenotype to the regenerated plant.

Such transgenic plants may be desirable for increasing the insecticidal resistance of a monocotyledonous or dicotyledonous plant, by incorporating into such a plant, a transgenic DNA segment encoding an insecticidal protein which is toxic to insects. Particularly preferred plants include corn, wheat, soybeans, turf grasses, ornamental plants, fruit trees, shrubs, vegetables, grains, legumes, and the like, or any plant into which introduction of an insecticidal protein transgene is desired.

In a related aspect, the present invention also encompasses a seed produced by the transformed plant, a progeny from such seed, and a seed produced by the progeny of the original transgenic plant, produced in accordance with the above process. Such progeny and seeds will have a protein encoding transgene stably incorporated into its genome, and such progeny plants will inherit the traits afforded by the introduction of a stable transgene in Mendelian fashion. All such transgenic plants having incorporated into their genome transgenic DNA segments encoding an insecticidal protein toxin are aspects of this invention.

The toxin-encoding genes of the subject invention can be introduced into a wide variety of microbial or plant hosts. Expression of the toxin gene results, directly or indirectly, in the intracellular production and maintenance of the pesticide proteins. Thus, the target pest can contact the pesticidal proteins by ingesting plant tissue containing the pesticidal proteins, which are toxic to the pest. The result is control of the pest. Alternatively, suitable microbial hosts, e.g., *Pseudomonas*, can be applied to the situs of the pest, where some of which can proliferate, and are ingested by the target pests. The microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, certain host microbes should be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

B.t. or recombinant cells expressing a B.t. toxin can be treated to prolong the toxin activity and stabilize the cell. The pesticide microcapsule that is formed comprises the B.t. toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., *Animal Tissue Techniques*, W.H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bio-availability or bioactivity of the toxin.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of Cells. The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art.

In another important embodiment, the bioinsecticide composition comprises a wettable powder, dust, pellet, granule, collodial concentrate, or other formulation. This powder comprises bacterial cells which expresses a novel protein disclosed herein. Preferred bacterial cells are B.t. cells, however, bacteria such as *B. megaterium, B. subtilis, E. coli,* or *Pseudomonas* spp. cells transformed with a DNA segment disclosed herein and expressing the protein are also contemplated to be useful. Such dry forms of the insecticidal compositions may be formulated to dissolve immediately upon wetting, or alternatively, dissolve in a controlled-release, sustained release, or other time-dependent manner.

In an additional important embodiment, the bioinsecticide composition comprises an aqueous suspension of bacterial cells such as those described above which express the protein. Such aqueous suspensions may be provided as a concentrated stock solution which is diluted prior to application, or alternatively, as a diluted solution ready-to-apply. Formulations may include the addition of surfactants, dispersants, inert carriers, and other components to facilitate handling and application for particular target pests. These formulations and application procedures are all well known in the art. When the insecticidal compositions comprise intact B.t. cells expressing the protein of interest, such bacteria may be formulated in a variety of ways.

Formulated bait granules containing an attractant and spores and crystals of the B.t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. Plant and soil treatments of B.t. cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

In another important embodiment, the bioinsecticide composition comprises a water dispersible granule. This granule comprises bacterial cells which expresses a novel protein disclosed herein. Preferred bacterial cells are B.t. cells, however, bacteria such as *B. megaterium, B. subtilis, E. coli,* or *Pseudomonas* spp. cells transformed with a DNA segment disclosed herein and expressing the protein are also contemplated to be useful.

The inventors contemplate that the protein compositions disclosed herein will find particular utility as insecticides for topical and/or systemic application to field crops, grasses, fruits and vegetables, and ornamental plants. In a preferred embodiment, the bioinsecticide composition comprises an oil flowable suspension of bacterial cells which expresses a novel protein or proteins disclosed herein. Preferably the cells are B.t., however, any such bacterial host cell expressing the novel nucleic acid segments disclosed herein and producing a protein is contemplated to be useful, including but not limited to *B. megaterium, B. subtilis, E. coli,* or *Pseudomonas* spp.

The novel insecticidal proteins or insecticidal protein-derived toxins may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the protein and apply solutions, suspensions, or collodial preparations of such crystals and/or spores as the active bioinsecticidal composition.

Regardless of the method of application, the amount of the active component(s) are applied at an insecticidally-effective amount, which will vary depending on such factors as, for example, the specific insects to be controlled, the specific plant or crop to be treated, the environmental conditions, and the method, rate, and quantity of application of the insecticidally-active composition.

The insecticide compositions described may be made by formulating the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

The insecticidal compositions of this invention are applied to the environment of the target insect, typically onto the foliage and/or in the rhizosphere (the soil surrounding plant roots) of the plant or crop to be protected, by conventional methods, preferably by spraying. The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art.

The insecticidal composition of the invention may be employed in the method of the invention singly or in combination with other compounds, including and not limited to other pesticides. The method of the invention may also be used in conjunction with other treatments such as surfactants, detergents, polymers or time-release formulations. The insecticidal compositions of the present invention may be formulated for either systemic or topical use.

The concentration of insecticidal composition which is used for environmental, systemic, or soil application will vary widely depending upon the nature of the particular formulation, means of application, environmental conditions, and degree of biocidal activity. Typically, the bioinsecticidal composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the active ingredient by weight.

The insecticidal formulation may be administered to a particular plant or target area in one or more applications as needed, with a typical field application rate per hectare ranging on the order of from about 50 g to about 500 g of active ingredient, or of from about 500 g to about 1000 g, or of from about 1000 g to about 5000 g or more of active ingredient.

In particular embodiments, the inventors contemplate the use of antibodies, either monoclonal or polyclonal which bind to the proteins disclosed herein. Means for preparing and characterizing antibodies are well known in the art.

The present invention also provides compositions, methods and kits for screening samples suspected of containing an insecticidal protein toxin or a gene encoding such a toxin. Such screening may be performed on samples such as transformed host cells, transgenic plants, progeny or seed thereof, or laboratory samples suspected of containing or producing such a polypeptide or nucleic acid segment. A kit can contain a novel nucleic acid segment or an antibody of the present invention. The kit can contain reagents for detecting an interaction between a sample and a nucleic acid or an antibody of the present invention. The provided reagent can be radio-, fluorescently- or enzymatically-labeled. The kit can contain a known radiolabeled agent capable of binding or interacting with a nucleic acid or antibody of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent that may be provided.

In still further embodiments, the present invention concerns immunodetection methods and associated kits. It is proposed that the proteins or peptides of the present invention may be employed to detect antibodies having reactivity therewith, or, alternatively, antibodies prepared in accordance with the present invention, may be employed to detect proteins or protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a protein or peptide or a protein-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of proteins or related peptides and/or antibodies in a sample. Samples may include cells, cell supernatants, cell suspensions, cell extracts, enzyme fractions, protein extracts, or other cell-free compositions suspected of containing proteins or peptides. Generally speaking, kits in accordance with the present invention will include a suitable protein, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquoted. The kits of the present invention will also typically include a means for containing the antibody, antigen, and reagent containers in close confinement for commercial sale. Such containers may include injection or blow-molded plastic containers into which the desired vials are retained.

ELISAs and Immunoprecipitation

ELISAs may be used in conjunction with the invention. In an ELISA assay, proteins or peptides incorporating protein antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/TWEEN® surface active agent (ICI Americas, Inc., Wilmington, Del.). These added agents also tend to assist in the reduction of nonspecific background. The layered antisera is then allowed to incubate for from about 2 to about 4 hours, at temperatures preferably on the order of about 25° C. to about 27° C. Following incubation, the antisera-contacted surface is washed so as to remove non-immunocomplexed material. A preferred washing procedure includes washing with a solution such as PBS/TWEEN® surface active agent, or borate buffer.

Following formation of specific immunocomplexes between the test sample and the bound antigen, and subsequent washing, the occurrence and even amount of immunocomplex formation may be determined by subjecting to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS/TWEEN®) surface active agent.

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

The anti-protein antibodies of the present invention are particularly useful for the isolation of other protein antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Non-ionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

The compositions of the present invention will find great use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immuno-precipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

The present invention is also directed to protein or peptide compositions, free from total cells and other peptides, which comprise a purified protein or peptide which incorporates an epitope that is immunologically cross-reactive with one or more anti-protein antibodies. In particular, the invention concerns epitopic core sequences derived from insecticidal proteins or peptides.

As used herein, the term "incorporating an epitope(s) that is immunologically cross-reactive with one or more anti-protein antibodies" is intended to refer to a peptide or protein antigen which includes a primary, secondary, or tertiary structure similar to an epitope located within a protein or polypeptide. The level of similarity will generally be to such a degree that monoclonal or polyclonal antibodies directed against the protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of Cry immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, e.g., U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to proteins, and in particular insecticidal and insecticidal-related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the protein-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins. Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. The amino acid identity will typically be greater than 60%, preferably be greater than 75%, more preferably greater than 80%, more preferably greater than 90%, and can be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. Modification and changes may be made in the primary structure of the toxins of the present invention to produce derivatives, analogs and mutants and DNA segments which encode them and still obtain a functional insecticidal molecule that encodes a protein or peptide with desirable characteristics. In particular embodiments of the invention, mutated proteins are contemplated to be useful for increasing the insecticidal activity of the protein, and consequently increasing the insecticidal activity and/or expression of the recombinant transgene in a plant cell. The amino acid changes may be achieved by changing the codons of the DNA sequence, according to the codons given in Table 2.

TABLE 2

| Amino Acids | Abbreviation | Abbreviation | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |

TABLE 2-continued

| Amino Acids | Abbreviation | Abbreviation | Codons |
|---|---|---|---|
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected protein gene sequence, e.g., a sequence such as that shown in SEQ ID NOs:1, 3, 5, 7, 9, 11, 13, 15, 17, 19, 21, 23, 25, 61, 62, 64, 65, 67, 69, 70, 72, 73, 75, 77, 79, 81, 83, 85, 87, 89, 90, 92, 94, 96, 98, 100, 102, and 104. The ability of such nucleic acid probes to specifically hybridize to a protein-encoding gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a protein gene from B.t. using PCR™ technology. Segments of related protein genes from other species may also be amplified by PCR™ using such primers.

The present invention contemplates an expression vector comprising a polynucleotide of the present invention. Thus, in one embodiment an expression vector is an isolated and purified DNA molecule comprising a promoter operatively linked to a coding region that encodes a polypeptide of the present invention, which coding region is operatively linked to a transcription-terminating region, whereby the promoter drives the transcription of the coding region.

As used herein, the term "operatively linked" means that a promoter is connected to a coding region in such a way that the transcription of that coding region is controlled and regulated by that promoter. Means for operatively linking a promoter to a coding region are well known in the art.

In a preferred embodiment, the recombinant expression of DNAs encoding the proteins of the present invention is preferable in a *Bacillus* host cell. Preferred host cells include B.t., *B. megaterium, B. subtilis*, and related bacilli, with B.t. host cells being highly preferred. Promoters that function in bacteria are well-known in the art. An exemplary and preferred promoter for the *Bacillus* crystal proteins include any of the known crystal protein gene promoters, including the insecticidal protein gene promoter, and promoters specific for B.t. sigma factors, such as $\sigma^E$ and $\sigma^K$. Alternatively, mutagenized or recombinant crystal protein-encoding gene promoters may be engineered by the hand of man and used to promote expression of the novel gene segments disclosed herein.

In an alternate embodiment, the recombinant expression of DNAs encoding the proteins of the present invention is performed using a transformed Gram-negative bacterium such as an *E. coli* or *Pseudomonas* spp. host cell. Promoters which function in high-level expression of target polypeptides in *E. coli* and other Gram-negative host cells are also well-known in the art.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive, and temporally regulated, spatially regulated, and spatio-temporally regulated.

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Regardless of transformation technique, the gene is preferably incorporated into a gene transfer vector adapted to express the B.t. insecticidal toxin genes and variants in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus (CaMV), and the like may be used. Plant-derived promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g., actin, ubiquitin, CaMV 35S). Tissue specific promoters are responsible for gene expression in specific cell or tissue types, such as the seeds (e.g., zein, oleosin, lectin, napin, ACP (Acyl Carrier Protein)), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Exemplary tissue-specific promoters are corn sucrose synthetase 1, corn alcohol dehydrogenase 1, corn light harvesting complex, corn heat shock protein, pea small subunit RuBP Carboxylase, Ti plasmid mannopine synthase, Ti plasmid nopaline synthase, *petunia* chalcone isomerase, bean glycine rich protein 1, CaMV 35s transcript and Potato patatin. Preferred promoters are the cauliflower mosaic virus (CaMV 35S) promoter and the S-E9 small subunit RuBP carboxylase promoter.

Under certain circumstances it may be desirable to use an inducible promoter. An inducible promoter is responsible for expression of genes in response to a specific signal, such as: physical stimulus (e.g., heat shock genes); light (e.g., RUBP carboxylase); hormone (e.g., glucocorticoid); antibiotic (e.g., tetracycline); metabolites; and stress (e.g., drought). Other desirable transcription and translation elements that function in plants may be used, such as 5' untranslated leader sequences, RNA transcription termination sequences and poly-adenylate addition signal sequences. Numerous plant-specific gene transfer vectors are known to the art.

An expression vector containing a coding region that encodes a polypeptide of interest is engineered to be under control of the lectin promoter and that vector is introduced into plants using, for example, a protoplast transformation method. The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of Agrobacterium tumefaciens. However, several other plant integrating vector systems are known to function in plants including pCaMVCN transfer control vector. Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II (nptII) and nopaline synthase 3' non-translated region.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer insecticidal activity to a cell is preferably an insecticidal protein toxin-encoding gene.

A bacterium, a yeast cell, plant cell, or a plant transformed with an expression vector of the present invention is also contemplated. A transgenic bacterium, yeast cell, plant cell, or plant derived from such a transformed or transgenic cell is also contemplated. Means for transforming bacteria and yeast cells are well known in the art. Typically, means of transformation are similar to those well-known means used to transform other bacteria or yeast such as E. coli or Saccharomyces cerevisiae.

Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by Agrobacterium infection, direct delivery of DNA such as, for example, by PEG-mediated transformation of protoplasts, by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods; (2) physical methods such as microinjection, electroporation and the gene gun; (3) viral vectors; and (4) receptor-mediated mechanisms.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced insecticidal activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments.

Application of these systems to different plant strains depends upon the ability to regenerate that particular plant strain from protoplasts. Illustrative methods for the regeneration of cereals from protoplasts are described (WO 1997/013843).

To transform plant strains that cannot be successfully regenerated from protoplasts, other ways to introduce DNA into intact cells or tissues can be utilized. For example, regeneration of cereals from immature embryos or explants can be effected. In addition, "particle gun" or high-velocity microprojectile technology can be utilized.

Using that latter technology, DNA is carried through the cell wall and into the cytoplasm on the surface of small metal particles. The metal particles penetrate through several layers of cells and thus allow the transformation of cells within tissue explants.

By transforming a suitable host cell, such as a plant cell, with a recombinant insecticidal protein encoding gene-containing segment, the expression of the encoded protein (i.e., a bacterial protein or polypeptide having insecticidal activity against coleopterans) can result in the formation of insect-resistant plants.

By way of example, one may utilize an expression vector containing a coding region for a B.t. protein and an appropriate selectable marker to transform a suspension of embryonic plant cells, such as wheat or corn cells using a method such as particle bombardment to deliver the DNA coated on microprojectiles into the recipient cells. Transgenic plants are then regenerated from transformed embryonic calli that express the insecticidal proteins.

The formation of transgenic plants may also be accomplished using other methods of cell transformation which are known in the art such as *Agrobacterium*-mediated DNA transfer. Alternatively, DNA can be introduced into plants by direct DNA transfer into pollen, by injection of the DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art. This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art. In this procedure, transformants are cultured in the presence of a selection agent and in a medium that induces the regeneration of shoots in the plant strain being transformed.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of a coding region (e.g., an insecticidal gene) that encodes the polypeptide of interest. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal capacity against insects, preferably in the field, under a range of environmental conditions. The inventors contemplate that the present invention will find particular utility in the creation of transgenic plants of commercial interest including corn and various turf grasses, wheat, corn, rice, barley, oats, a variety of ornamental plants and vegetables, as well as a number of nut- and fruit-bearing trees and plants.

All patents, patent applications, provisional applications, and publications referred to or cited herein are incorporated by reference in their entirety to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting.

All percentages are by weight and all solvent mixture proportions are by volume unless otherwise noted. All temperatures are in degrees Celsius.

Example 1

Culturing of B.t. Isolates of the Invention

A subculture of the B.t. isolates, or mutants thereof, can be used to inoculate the following medium, a peptone, glucose, salts medium.

The salts solution and $CaCl_2$ solution are filter-sterilized and added to the autoclaved broth at the time of inoculation. Flasks are incubated at 30° C. on a rotary shaker at 200 rpm for 24-48 hours.

The above procedure can be readily scaled up to large fermenters by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

Example 2

Isolation of the Genes Encoding Insecticidal Proteins

Genomics and proteomics studies showed that, 6 out of the 7 WCR active B.t. and *Bacillus thuringiensis israelensis* (B.t.i.) strains were identified to have one or more known WCR active genes that may contribute to the WCR activity observed in screening bioassays, but one strain DBt12172 was found to have two hypothetical proteins via proteomic approach that were designated as IRDIG27501 and IRDIG27642, and a B.t. S-layer protein (IRDIG27674).

The three genes were cloned for protein expression and bioassays. Expression vectors pDAB122756, pDAB122768 and pDAB122774 were constructed using standard molecular biology procedures with an *E. coli*-B.t. shuttle vector pDAB101622 and the PCR products targeting these genes. The open reading frames with the 5' and 3' untranslated regions (UTRs) of IRDIG27501, IRDIG27642 and IRDIG27674 were amplified using the genomic DNA of DBt12172 as a template and the primers designed for each gene (Table 4) through PCR. Phusion High-Fidelity DNA Polymerase from New England Biolabs (NEB) was used for PCR following the program: 98° C. for 3 min followed by 98° C. for 50 sec, 51° C. for 30 sec, and 72° C. for 1 min (repeated for 5 cycles) and then 98° C. for 30 sec, 58° C. for 30 sec, and 72° C. for 1 min (repeated 35 cycles), and a final step of 72° C. for 5 min and held at 4° C. The resulting PCR products were sub-cloned into pCR-Blunt II-TOPO (Invitrogen) for sequencing confirmation and then cloned into pDAB101622 at BamHI/KpnI for IRDIG27501 and IRDIG27642, respectively, resulting in the expression vectors pDAB122756 and pDAB122774 that were used for expression of IRDIG27501 and IRDIG27642 separately in a toxin-minus (plasmid cured) B.t. strain 4Q7. For IRDIG27674, the In-Fusion strategy from Clontech was used to clone it into pDAB101622 and pDAB112695 respectively that were linearized by SmaI digestion. The resulting expression vectors were designated as pDAB122768 and pDAB122773. The vector pDAB101622 did not have a promoter and terminator to regulate target gene expression. All expression of these genes cloned into pDAB101622 were controlled by their own native promoters and terminators. However, pDAB112695 contained a Cry1Ac promoter and terminator from another B.t. strain. Thus, the B.t. S-layer protein expression in pDAB122773 was regulated by a Cry1Ac promoter and terminator.

Cloning for co-expression of these two novel genes, IRDIG27501 and IRDIG27642, was completed to test for binary activity. Two PCR products of IRDIG27501 and IRDIG27642 were generated respectively using the primers 12172-00709-F1BamHI & 12172-00709-R1SacII, and 12172-00733-F1SacII & 12172-00733-R1KpnI and then cloned into pDAB101622 simultaneously at BamHI, SacII and KpnI sites in the orientation as shown in FIG. 1, where IRDIG27501 and IRDIG27642 were connected to each other at SacII site.

The Nucleic acid sequences of IRDIG27501 and IRDIG27642 were searched through BLAST against the internal B.t. genomic sequence database of Dow AgroSciences LLC. IRDIG27501 search did not return any significant hit, and the closest neighbor sequence shares only 32% amino acid sequence identity. However, IRDIG27642 search returned many significant hits with a wide range of amino acid sequence identity from 100% to 40%. These hits were designated as homologs of IRDIG27642.

Nucleic acids encoding these homologous insecticidal proteins were isolated from various B.t. strains. Forward and reverse primers for Polymerase Chain Reaction (PCR) were designed and used to amplify nucleotide sequences encoding the full-length insecticidal proteins (Table 4). The amplified fragments were subcloned into a protein expression vector backbone. BLAST searches of these gene sequences against NCBI, Pfam, and GenomeQuest databases did not return any significant hits. These sequence search results indicate that these genes are novel among all known protein sequences.

Standard cloning methods were used in the construction of *Pseudomonas fluorescens* (Pf) expression plasmids engineered to produce full-length insecticidal protein toxins encoded by native and plant-optimized coding regions. Restriction endonucleases were obtained from New England BioLabs (NEB; Ipswich, Mass.) and T4 DNA Ligase (NEB; Ipswich, Mass.) was used for DNA ligation. DNA fragments were purified using a QIAquick® Gel Extraction Kit (Qiagen, Venlo, Limburg) after agarose Tris-acetate gel electrophoresis. Plasmid preparations were performed using the NucleoSpin® Plasmid Kit (Macherey-Nagel Inc, Bethlehem, Pa.) following the instructions of the suppliers for low-copy plasmid purification or the Qiagen Plasmid Plus Midi Kit® (Qiagen, Hilden, Germany).

All insecticidal proteins were analyzed phylogenetically and non-redundant representative proteins were selected for WCR activity validation. The open reading frame (ORF) sequences of unique representative insecticidal proteins were identified. These ORFs were amplified through PCR using the genomic DNAs isolated from the wild-type B.t. strains containing the target insecticidal proteins as a template and using the primers listed in Table 4.

The resulting IRDIG27501 and IRDIG27642 PCR products did not have their native promoters and terminators but have their native ribosomal binding site (RBS) sequences AGGAGA for IRDIG27501 and AGGAGT for IRDIG27642 prior to the ATG start codon. The PCR products were cloned into pDAB116687 and pDAB116693 at SpeI/XhoI respectively, resulting in pDAB121089 and pDAB121093. The ligation reaction was transformed following the standard protocol. This DNA/cell mix was transferred to a pre-labeled Bio-rad 0.2 cM electroporation cuvette which was chilled on ice. The cuvette was dried and pulsed with a Bio-Rad Gene Pulser Xcell electroporater using the pre-set *P. aeruginosa* setting (2.25 kV/cm, 25 µF, and 200Ω). The cuvette was placed back on ice, transferred to a laminar flow hood, diluted with SOC media, and struck out on an LB plate supplemented with 20 µg/ml tetracycline. The plate was placed at 28° C. overnight. Individual colonies were picked up for each Mini Prep, insert check, and construct validation through restriction enzyme digestion and sequencing.

TABLE 4

Primers used for PCR to amplify the open reading frames of insecticidal proteins for cloning and expression in either B.t. or P.f.

| IRDIG # | Primer ID | Sequence | SEQ ID NO |
|---|---|---|---|
| 27642 | 12172-00733-F1BamHI | GGATCCGTCGTAGTACCAGTATGACCAAGTTG | 27 |
|  | 12172-00733-R1KpnISacII | CCGCGGGGTACCCCAAAATAATATCTTTCTTGAATTGTTTCTC | 28 |
| 27642 | 12172-00733-F2BamHI | GGATCCAGGAGTAAAAACACATATGAATAATCATTTATTAG | 29 |
|  | 12172-00733-R2KpnI | GGTACCTTATTAAGCTTTACCATCATATGTTAAAGTATATTTTGGCC | 30 |
| 27642 | 12172-00733-F2SpeI | ACTAGTAGGAGTAAAAACACATATGAATAATCATTTATTAG | 31 |
|  | 12172-00733-R2XhoI | CTCGAGTTATTAAGCTTTACCATCATATGTTAAAGTATATTTTGGCC | 32 |

TABLE 4-continued

Primers used for PCR to amplify the open reading frames of insecticidal proteins for cloning and expression in either B.t. or P.f.

| IRDIG # | Primer ID | Sequence | SEQ ID NO |
|---|---|---|---|
| 27642 | 12172-00733-F1SacII | CCGCGGGTCGTAGTACCAGTATGACCAAGTTG | 33 |
| | 12172-00733-R1KpnI | GGTACCCCAAAATAATATCTTTCTTGAATTGTTTCTC | 34 |
| 27501 | 12172-00709-F1BamHI | GGATCCAGCACCAGAACCCTCCAAATAC | 35 |
| | 12172-00709-R1SacII | CCGCGGCCGTCTTTTCTGGAGATAGTTTGAGTTACTATC | 36 |
| 27501 | 12172-00709-F1SacII | CCGCGGAGCACCAGAACCCTCCAAATAC | 37 |
| | 12172-00709-R1KpnI | GGTACCCCGTCTTTTCTGGAGATAGTTTGAGTTACTATC | 38 |
| 28672 | 3286_28446F | GTGTACTAGTATGAATAACCAGTTATTAGATTTACTGTCAAAAACTC | 39 |
| | 3286_28446R | TCTCCTCGAGTTAAGCTCTGCCATCATAATGTAAATCATATTTTTGAC | 40 |
| 28674 | 10927_04813F | GTGTACTAGTATGGATAATCATTTTTTAGATTTAATCTCAAAAG | 41 |
| | 10927_04813R | TCTCCTCGAGTTAAGCTCTACCATCATAATGTAAATCATATTTTTGAC | 42 |
| 28676 | 10912_04716F | GTGTACTAGTATGTCTTTCTTGAACTGTTTCCCTTTAAAATATC | 43 |
| | 10912_04716R | TCTCCTCGAGCTAAGCTCTACCATCATATTTCAAAGTATATCTTAC | 44 |
| 28680 | 5792_00134F | GTGTACTAGTATGGCAACAGTTAGCGGAAAAATAATAATAAATAC | 45 |
| | 5792_00134R | TCTCCTCGAGTTAATTACTACTGTCATATTTTAAAATATATTTTTGTCCAAGC | 46 |
| 28682 | 10535_00259F | GTGTACTAGTATGAATAATACATTATTGGAATTACTTTCAAAAATAAAAAAAGAATTCTTTGG | 47 |
| | 10535_00259R | TCTCCTCGAGTTAAGCTCTACCTTTGTATTGTAATGTATATCTTTCTC | 48 |
| 28684 | 11805_03530F | GTGTACTAGTATGAATAATACATTATTGGAATTACTTTCAAAAATAAAAAAAGAATTCTTTGG | 49 |
| | 11805_03530R | TCTCCTCGAGTTAAGCTCTACCTTTGTATTGTAATGTATATCTTTCTCC | 50 |
| 28686 | 9974_00530F | GTGTACTAGTATGAATAACACATTATTGGAATTACTTTCAAAAATAAAAAAAGAATTCTTTGG | 51 |
| | 9974_00530R | TCTCCTCGAGTTAAGCCCTACCTTTGTATTGTAATGTATATCTTTCTCC | 52 |
| 28688 | 3066_03546F | GTGTACTAGTATGTATATGAATAATACATTATTGGAATTACTTTCAAAAATAAAAAAAGAATTCTTTGG | 53 |
| | 3066_03546R | TCTCCTCGAGTTAAGCTCTACCTTTGTATTGTAATGTATATCTTTCTCC | 54 |
| 28690 | F | GTGTACTAGTATGTATATGAATAATACATTATTGGAATTACTTTCAAAAATAAAAAAAG | 55 |
| | R | TCTCCTCGAGTTAAGCTCTACCTTTGTATTGTAATGTATATCTTTCTCC | 56 |
| 28692 | F | GTGTACTAGTATGGATAATCATTTATTAGGGTTACTTTCAAAAATCC | 57 |
| | R | TCTCCTCGAGTTAAGTTTTAGCTACAGGTGTCAAGGTGTATCTACTACC | 58 |
| 28694 | F | GTGTACTAGTATGAAAAAAGGATTTCTTGCCGTATCATTG | 59 |
| | R | TCTCCTCGAGTTAACGTGGAGCTAATGTATAGGTTTCAC | 60 |

Two 500 mL cultures of production media in 2.5-L Ultra Yield flasks were used for the expression of proteins. Two 1-mL glycerol stock of DPf45284 or DPf45134 was added to each of the autoclaved flasks containing media and flasks were incubated with shaking for 24 hours at 30° C., 300 rpm. Following 24 hours of growth, a 0.5 mL sample was obtained for an $OD_{600}$ read and pre-induction sample. A drop of antifoam 204 (Sigma, A8311-50ML) was added to each flask and protein expression was induced with IPTG. The cultures were returned to the shaker for an additional 48 hours. A half-milliliter sample was pulled every 24 hours from each flask again for protein expression analysis and $OD_{600}$ reads.

These samples and the pre-induction samples were resuspended in 500 µL BugBuster® Master Mix with 0.1 mm glass beads. The suspensions were incubated with shaking at room temperature for 30 minutes, and then lysed using a Geno/Grinder 2010 at 1750 rpm for 3 minutes. The samples were centrifuged, and the soluble and insoluble fractions were separated. The insoluble fraction was solubilized by adding 0.5 mL of extraction buffer (8 M urea, 0.5 M NaCl, 25 mM $NaPO_4$, pH 10.4). Both fractions were analyzed for protein expression via SDS-PAGE, using a NuPAGE® Novex® Tris-Glycine 4-20% Midi gel run in 1× Tris-Glycine SDS running buffer (Invitrogen). Samples were mixed with 25 µL 6× Tris-Glycine SDS sample buffer (Invitrogen) and 1 µL 1M DTT. The gel was run at 200 V for 60 minutes, and then stained with SimplyBlue™ SafeStain (Life Technologies, LC6060). Following staining, the gel was placed in water. To estimate expression levels, densitometry analysis was performed using a GE Image Scanner III (GE Healthcare). A standard curve was generated by loading 0.2, 0.5, 1.5, 3.0, and 6.0 µg of bovine serum albumin (BSA) per lane. Protein bands were detected and quantified using ImageQuant TL software (GE Healthcare).

Example 3

Design of Plant Codon-Optimized Insecticidal Toxin Genes

One skilled in the art of plant molecular biology will understand that multiple DNA sequences may be designed to encode a single amino acid sequence. A common means of increasing the expression of a coding region for a protein of interest is to tailor the coding region in such a manner that its codon composition resembles the overall codon composition of the host in which the gene is destined to be expressed. Guidance regarding the design and production of synthetic genes can be found in, for example, WO1997013402, U.S. Pat. Nos. 6,166,302, and 5,380,831.

A DNA sequence having a maize codon bias was designed and synthesized to produce an insecticidal protein in transgenic monocot plants. A codon usage table for maize (*Zea mays* L.) was calculated from hundreds of protein coding sequences obtained from sequences deposited in GenBank. A rescaled maize codon set was calculated after omitting any synonymous codon used less than about 10% of total codon uses for that amino acid.

Further refinements of the sequences were made to eliminate undesirable restriction enzyme recognition sites, potential plant intron splice sites, long runs of A/T or C/G residues, and other motifs that might interfere with mRNA stability, transcription, or translation of the coding region in plant cells. Other changes were made to introduce desired restriction enzyme recognition sites, and to eliminate long internal Open Reading Frames (frames other than +1). These changes were all made within the constraints of retaining the maize-biased rescaled codon composition. The maize-optimized DNA sequences encoding insecticidal toxins are disclosed as SEQ ID NOs:61, 62, 64, 65, 67, 69, 70, 72, 73, and 75.

The foregoing provides several embodiments of the isolated polynucleotide(s) according to the invention, including polynucleotides that are codon-optimized for expression of insecticidal toxin polypeptides of the invention.

Example 4

Construction of Expression Plasmid Encoding Insecticidal Protein Toxins in Bacterial Hosts Standard cloning methods were used in the construction of *Pseudomonas fluorescens* (Pf) expression plasmids engineered to produce the insecticidal protein toxins encoded by either the native or the maize-optimized coding sequences. Restriction endonucleases were obtained from New England BioLabs (NEB; Ipswich, Mass.) and T4 DNA Ligase (Invitrogen) was used for DNA ligation. Plasmid preparations were performed using the NucleoSpin® Plasmid Kit (Macherey-Nagel Inc, Bethlehem, Pa.) following the instructions of the supplier. DNA fragments were purified using the QIAQUICK Gel Extraction kit (Qiagen) after agarose Tris-acetate gel electrophoresis. The linearized vector was treated with Antarctic Phosphatase (NEB) to enhance formation of recombinant molecules.

The resulting PCR products lacking the native regulatory element sequences were cloned into pDAB122775 for expression in B.t. host 4Q7 and into pDOW1169 for expression in a Pfhost, respectively. The cloning sites used for both B.t. and Pf systems were XbaI/XhoI or SpeI/XhoI. B.t. expression vector pDAB122775 includes a Cry1Ac crystal protein gene promoter (expressed during B.t. cell sporulation), ribosomal binding site (RBS) and the Cry1Ac terminator, while in pDOW1169 these target gene expressions were driven by Ptac promoter and IPTG induction. pDOW1169 is a low copy plasmid with the RSF1010 origin of replication, a pyrF gene, and a ribosome binding site preceding the restriction enzyme recognition sites into which DNA fragments containing protein coding regions may be introduced (U.S. Pat. No. 7,618,799). If not expressed in either B.t. or Pf, they were cloned into an *E. coli* expression vector such as pET280(Kan) at SpeI/XhoI. Constructs were generated using standard molecular cloning procedures that are well known in the art.

The expression plasmids (pDAB121093, 127479, 127480, 127481, 127482, 127484, 127485, 127486, 127487, 127488, 127489, 127490, 127491) were transformed by electroporation into DC454 (a near wild-type *P. fluorescens* strain having mutations ΔpyrF and lsc::lacIQI), or derivatives thereof, recovered in SOC-Soy hydrolysate medium, and plated on selective medium (M9 glucose agar lacking uracil, Sambrook et al., supra).

Protein expression experiments for these insecticidal proteins were performed first in 4Q7 B.t. host and then in DPf10 Pf host. Briefly, recombinant B.t. cultures were grown in 50 ml of Dow AgroSciences Proprietary medium broth in a 250-ml baffled flask at 28° C./180-200 rpm for 24-32 hours. The mixture of the crystals and endospores was harvested by centrifugation at 6,000 g at 4° C. for 15 min and followed by washing in 10 ml of 1M NaCl, 0.1% Triton X-100 solution and then in 35 ml of ionized water. The final pellet was suspended in 2 ml deionized water for WCR feeding assays.

The B.t. 4Q7 transformed with empty vector pDAB122775 was included as a negative control.

The transformation and selection methods are generally described available in US Patent Application No. 20060008877, U.S. Pat. No. 7,681,799, and US Patent Application No. 20080058262, incorporated herein by reference. Recombinant colonies were identified by restriction digestion of miniprep plasmid DNA.

Example 5

Preparation of Insecticidal Protein Samples

Production of insecticidal proteins for characterization and insect bioassay was accomplished by shake-flask-grown *P. fluorescens* strain harboring expression construct strains DPf46314, 48284, 48285, 48286, 48287, 48289, 48290, 48291, 48292, 48293, 48294, 48295, 48296. Stored glycerol stocks of the strain were used to inoculate defined production medium with 9.5% glycerol (Teknova Catalog No. 3D7426, Hollister, Calif.). Expression of the insecticidal gene(s) was induced by addition of isopropyl-β-D-1-thiogalactopyranoside (IPTG) after an initial incubation of 24 hours at 30° C. with shaking. Cultures were sampled at the time of induction and at various times post-induction. Cell density was measured by optical density at 600 nm ($OD_{600}$). Other culture media suitable for growth of *Pseudomonas fluorescens* may also be utilized, for example, as described in US Patent Application No. 20060008877. The post- and pre-induction samples were analyzed for target protein expression in both cellular soluble and insoluble fractions following BugBuster® lysis and extraction procedures. To estimate expression levels, densitometry analysis was performed using a GE Image Scanner III (GE Healthcare). Protein bands were detected and quantified using ImageQuant TL software (GE Healthcare) and BSA as a standard. The insecticidal protein accumulated in the insoluble fraction of lysed cells as inclusion bodies (IB). The cells were flash frozen in liquid nitrogen and stored at −80° C.

Inclusion Body (IB) Preparation for Insecticidal Proteins.

Pf derived cell pastes expressing full length insecticidal proteins were transferred from −80° C. storage to room temperature. Approximately 10 g of each was taken out and resuspended in cold lysis buffer (40 mL of 50 mM Tris, 200 mM NaCl, 10% glycerol, 0.5% Triton X-100, 20 mM EDTA, 1 mM DTT, pH 7.5) at 20% w/v. The resuspended pellet was incubated at room temperature while rocking with 0.4 mg/ml lysozyme for 20 minutes. This was followed by adding 0.1 mg/mL DNase with 0.1 M $MgCl_2$ and further incubation at 30° C. in a water bath for 20 minutes. The sample was sonicated using a Branson sonifier for 1 minute, duty cycle-60, output control 4 followed by centrifugation at 16,000 rpm for 30 minutes in a JA-17 rotor. The pellets were resuspended 2 additional times in 20% w/v cold lysis buffer with metal beads. The final two washes were carried out using the lysis buffer in the absence of triton-x-100, the supernatants were colorless and the IB pellets became firm and off-white in color. The inclusion bodies were resuspended in sterile-filtered distilled water containing 10 mM EDTA, pH 8.0, aliquoted into 1.5 mL and frozen at −80° C. until needed.

Inclusion Body Solubilization.

Inclusion bodies were thawed at room temperature in a water bath. The inclusion bodies were brought up to 10 mL in 0.1 M CAPS, pH 11, followed by sonication for 1 min at output control 4, duty cycle 40%. The solubilized protein was centrifuged for 20 min at 16,000 rpm in a JA17 rotor. The samples were concentrated by 15 mL Amicon 3K MWCO to give a final volume of about 2 mL and buffer exchanged once by adding 18 mL 10 mM CAPS, pH 11 and concentrating them down to 2 mL. This was followed by desalting on PD10 columns that had been previously equilibrated using 10 mM CAPS pH 11.

Insecticidal protein purified from the IB preparations was analyzed by SDS-PAGE. Molecular weight was determined from amino acid sequence. One band was detected, as expected at ~21.1 kDa and was identified as IRDIG27642 by MALDI and N-terminal sequencing. Quantification of target bands was done by comparing densitometric values for the bands against Bovine Serum Albumin (BSA) samples run on the same gel to generate a standard curve.

The foregoing provides isolated polynucleotides, including nucleic acid constructs, and isolated insecticidal polypeptides according to the invention.

Purification of IRDIG27642 and its Homologs.

The inclusion body preparation and solubilization was performed as described earlier for the homologs. The supernatant was loaded onto a preequilibrated 5 mL HiTrap Q HP column with buffer A, 50 mM CAPS pH 11 at 1 mL/min. The protein was eluted over a gradient by increasing the concentration of buffer B (50 mM CAPS pH 11, 1 M NaCl) from 0 to 100% over 200 mL. SDS-PAGE analysis of the fractions was performed on a 4-20% Tris-glycine gel, ran in 1× Tris/Glycine/SDS buffer and stained the gel with GelCode Blue Stain Reagent and destained with water. All the fractions containing the target were identified by SDS-PAGE analysis and concentrated. The total protein was determined using the Bradford reagent and the target protein concentration was determined using densitometry.

IRDIG27501 Purification. IRDIG27501 Did not Form Inclusion Bodies and was Purified from Soluble Protein.

Approximately 50 g of pf cell paste was taken out and resuspended in cold lysis buffer at 20% w/v (50 mM Tris, 0.2 M NaCl, 10% glycerol, 20 mM ETDA, 4 mM Benzamidine, 1 mM DTT, 0.2% CHAPS, pH 7.5) with lysozyme at 0.25 mg/mL. The resuspended pellet was incubated at room temperature while rocking for 20 minutes. This was followed by adding 0.1 mg/mL DNase with 0.1 M $MgCl_2$ and further incubation at 30° C. in a water bath for another 20 minutes. The sample was sonicated twice using Branson Sonifier for 2 minute each, 30% duty cycle, output control-4 followed by centrifugation at 31,000 g for 30 minutes in a JA-17 rotor. The supernatants were saved for target protein analysis via SDS-PAGE before discarding. The pellets were resuspended 2 additional times in 20% w/v cold lysis buffer with metal beads. The pellet was solubilized in 0.1 M CAPS pH 11 at 4° C. with stirring for one hour followed by centrifugation at 31,000 g for 30 minutes.

The supernatant was loaded onto a preequilibrated 5 mL HiTrap Q HP column with buffer A, 50 mM CAPS pH 11 at 1 mL/min. The protein was eluted over a gradient by increasing the concentration of buffer B (50 mM CAPS pH 11, 1 M NaCl) from 0 to 100% over 200 mL. SDS-PAGE analysis of the fractions was performed on a 4-20% Tris-glycine gel, in 1× Tris/Glycine/SDS buffer and the gel was stained with GelCode Blue Stain Reagent and destained with water. All the fractions with the target protein were precipitated by addition of solid ammonium sulfate to give a final concentration of 30%, followed by incubation at 4° C. for 30 min and centrifugation at 31,000 g for 30 min in a JA-17 rotor.

The resuspended supernatant from the ammonium sulfate precipitation in 10 mM CAPS pH 11 was concentrated to ~25 ml with Amicon spin concentrators (3 kDa MWCO) then injected into a Superdex 75 column (XK26/100, ~450 ml bed volume) at 1 ml/min. All the fractions containing the target were identified by SDS-PAGE analysis and concentrated. The total protein was determined using the Bradford reagent and the target protein concentration was determined using densitometry.

Example 6

Insecticidal Activity of Proteins

Insecticidal proteins were tested and found to have insecticidal activity on larvae of the coleopteran insect, the western corn rootworm (*Diabrotica virgifera virgifera* LeConte).

Test insects were first instar (<24 hr after eclosion) western corn rootworm (WCR), *Diabrotica virgifera virgifera*. Non-diapausing *Diabrotica virgifera virgifera* eggs (Crop Characteristics, Inc., Farmington, Minn.) were incubated for 10 days at 28° C. and 60% RH. Black head eggs were surface sterilized with 10% formalin following the method by Pleau et al. (2002). Lepidopteran test insects comprised fall armyworm (FAW), *Spodopter afrugiperda* (J. E. Smith), corn earworm (CEW), *Heliothis zea* (Boddie), European corn borer (ECB), *Ostrinia nubilalis* (Hübner), and soybean looper (SBL), *Chrysodeixis includens*. There was no significant practical mortality or growth inhibition of IRDIG27501 combined with IRDIG27642 for these lepidopteran pests.

Proteins were bioassayed using a 48-well WCR bioassay format. An overlay diet bioassay was conducted in 48-well titer plates with each well containing 0.75 ml of the artificial Dow AgroSciences LLC proprietary WCR diet. Each test aliquot was pipetted at 40 μL/well onto the diet surface (0.95 $cm^2$) of 8 wells and dried under room temperature in a laminar flow. The treated diet surface of each well was infested with two *D. virgifera* neonates (24-48 hr old) and test insects were enclosed in the bioassay arena with Breathe Easy® gas permeable sealing membrane for micro titer plates (USA Scientific, Orlando, Fla.). Negative controls were 20 mM sodium citrate buffer, pH 3.5; 10 mM CAPS buffer, pH 11; the positive control was 100 μg/$cm^2$ Cry34/35Ab1 in sodium citrate buffer.

Bioassay trays were held under controlled environmental conditions (28° C., 60% relative humidity, 16:8 h light/dark) for 5 days. The total number of insects exposed to each protein sample, the number of dead insects, and the weight of surviving insects were recorded in all insect bioassays. Larvae which weighed 0.1 mg or less were considered moribund insects and were included in the percent practical mortality computation. Growth inhibition was calculated as follows:

$$GI=[1-(TWIT/TNIT)/(TWIBC/TNIBC)]$$

where TWIT is the Total Weight of Insects in the Treatment, TNIT is the Total Number of Insects in the Treatment, TWIBC is the Total Weight of Insects in the Background Check (Buffer control), and TNIBC is the Total Number of Insects in the Background Check (Buffer control). Bioassays were conducted under randomized complete block design and replicated at least 4 times, with 16 *D. virgifera virgifera* larvae per replicate. Data were analyzed with ANOVA and mean separation using Tukey HSD (P>0.05). Dose response analyses were performed. The growth inhibition concentration-response curves were determined using a nonlinear logistic 3-parameter model, and the effective concentrations required to cause 50% growth inhibition ($GI_{50}$) was estimated. These analyses were performed using JMP Pro, version 9.0.3, software (SAS Institute Inc., Cary, N.C.). Probit analyses of the pooled practical mortality data were conducted using POLO-PC (LeOra Software) to estimate the 50% lethal concentration ($LC_{50}$) of the concentration-response curves.

Both candidate insecticidal proteins IRDIG27501 and IRDIG27642 identified from DBt12172 crystal preparation (crystal and spore mixture) were expressed in a B.t. host separately and also in a combination. In addition, IRDIG27501 was expressed in a Pf host as well. The crystal preparations from the B.t. host expression system and the lysate of recombinant Pf expressing IRDIG27501 were tested for WCR activity separately and in combinations as shown in Table 5. Table 5 shows that crystal preparations for IRDIG27501 and IRDIG27642 did not exhibit obvious WCR activity when assayed separately; however, the combinations of IRDIG27501 and IRDIG27642 showed clear WCR activity either in manually mixed sample or in co-expressed sample.

WCR Hit rates of the crystal preparations derived from wild type DBt12172 and recombinant B.t. cultures expressing the candidate proteins IRDIG27501 and 27642 identified from this Bt strain are shown in Table 5. A Hit is visually scored and is defined as dead insects or live insects with equal or more than 50% of growth inhibition compared to negative control. Hit rates were calculated based on number of total Hit divided by total insect number tested.

TABLE 5

| pDAB ID/ Strain ID | IRDIG | Expression host | Rep 1 | Rep 2 | Rep 3 | Rep 4 | Mean | STDV |
|---|---|---|---|---|---|---|---|---|
| DBt12172 | wild type | Bt | 0.750 | 0.750 | 0.857 | 1.000 | 0.839 | 0.118 |
| pDAB122756 | 27501 | Bt | 0.000 | 0.250 | 0.375 | 0.143 | 0.192 | 0.159 |
| pDAB121089 | 27501 | Pf | 0.375 | 0.000 | 0.500 | 0.750 | 0.406 | 0.313 |
| pDAB122774 | 27642 | Bt | 0.125 | 0.125 | 0.000 | 0.000 | 0.063 | 0.072 |
| pDAB122769 | 27501 + 27642 (co-expression) | Bt | 1.000 | 1.000 | 0.875 | 1.000 | 0.969 | 0.063 |
| pDAB122756 + pDAB122774 | 27501 + 27642 (sample mix) | Bt + Bt | 0.500 | 0.500 | 0.429 | 0.250 | 0.420 | 0.118 |
| pDAB121089 + pDAB122774 | 27501 + 27642 (sample mix) | Pf + Bt | 1.000 | 1.000 | 0.625 | 1.000 | 0.906 | 0.188 |
| pDAB101662 | empty vector | Bt | 0.000 | 0.167 | 0.125 | 0.714 | 0.251 | 0.317 |
| 4Q7 | Bt host | Bt | 0.000 | 0.000 | 0.250 | 0.000 | 0.063 | 0.125 |

WCR insecticidal activity of homologous proteins of IRDIG27642 were tested further separately and in combinations with IRDIG27501 using purified protein samples expressed in either Pf or *E. coli*. The bioassay data demonstrate that most IRDIG27642 homologs alone showed significant WCR activity in either practical mortality or growth inhibition (Table 6), and the WCR activity clearly increased when mixed with IRDIG27501 (Table 7). Efficacy and growth inhibition of mixtures of IRDIG27501 with IRDIG28686, IRDIG28682, IRDIG28688, IRDIG28684, IRDIG28674, IRDIG28692, IRDIG28672 and IRDIG28680 at the tested concentrations were comparable to the positive control Cry34/35Ab1 (Table 7). Significant growth inhibition was determined for all the mixtures of the homologs with IRDIG27501. Tables 8 and 9 provided evidence that addition of IRDIG27501 to the homologs of IRDIG27642 significantly increase the % practical mortality and % growth inhibition by about 1.3-17.3 and 1.2-4.9-fold respectively.

TABLE 6

Mean percent practical mortality and mean percent growth inhibition of WCR for IRDIG27642 homologs tested alone

| | | | % Practical mortality | | | % Growth inhibition | | |
|---|---|---|---|---|---|---|---|---|
| Sample name | Rep | Conc. (ug/cm2) | Mean | Std Error | Tukey HSD (Pr > 0.05) | Mean | Std Error | Tukey HSD (Pr > 0.05) |
| Cry34/35Ab1 | 18 | 100 | 82.83 | 4.05 | A | 98.69 | 3.55 | A |
| IRDIG28684 | 6 | 23 | 35.75 | 7.02 | BC | 79.15 | 6.15 | AB |
| IRDIG28686 | 6 | 42 | 50.27 | 7.02 | B | 79.12 | 6.15 | AB |
| IRDIG28682 | 4 | 42 | 26.78 | 8.60 | BCD | 69.45 | 7.53 | ABC |
| IRDIG28688 | 6 | 42 | 49.67 | 7.02 | B | 69.27 | 6.15 | B |
| IRDIG28674 | 4 | 25 | 11.78 | 8.60 | BCD | 61.38 | 7.53 | BCD |
| IRDIG28680 | 4 | 42 | 21.11 | 8.60 | BCD | 56.51 | 7.53 | BCD |
| IRDIG28672 | 4 | 22 | 3.13 | 8.60 | CD | 34.20 | 7.53 | CDE |
| IRDIG27642 | 8 | 42 | 9.54 | 6.08 | CD | 30.59 | 5.32 | DE |
| IRDIG28692 | 4 | 42 | 9.55 | 8.60 | CD | 24.40 | 7.53 | DEF |
| IRDIG28676 | 4 | 42 | 5.36 | 8.60 | CD | 24.40 | 7.53 | DEF |
| IRDIG28694 | 4 | 42 | 4.90 | 8.60 | CD | 16.28 | 7.53 | EF |
| IRDIG28690 | 6 | 24 | 1.03 | 7.02 | CD | 10.92 | 6.15 | EF |
| 10 mM CAPS pH 11 | 18 | 0 | 3.57 | 4.05 | D | 0.00 | 3.55 | F |
| 20 mM NaCitrate pH 3.5 | 18 | 0 | 5.64 | 4.05 | D | 0.00 | 3.55 | F |

TABLE 7

Mean percent practical mortality and mean percent growth inhibition of WCR when exposed to combinations of IRDIG27642 homologs with IRDIG27501 insecticidal proteins

| | | | % Practical mortality | | | % Growth inhibition | | |
|---|---|---|---|---|---|---|---|---|
| Sample name | Conc. (ug/cm2) | Rep | Mean | Std Error | Tukey HSD (P > 0.05)[a] | Mean | Std Error | Tukey HSD (P > 0.05)[a] |
| Cry34/35Ab1 | 50 + 50 | 18 | 82.8 | 4.4 | A | 98.7 | 2.9 | A |
| IRDIG27501 + IRDIG28686 | 84 + 42 | 4 | 93.7 | 9.3 | A | 100.0 | 6.1 | AB |
| IRDIG27501/ + IRDIG28682 | 84 + 42 | 4 | 93.4 | 9.3 | A | 99.8 | 6.1 | AB |
| IRDIG27501 + IRDIG28688 | 84 + 42 | 4 | 93.5 | 9.3 | A | 98.9 | 6.1 | AB |
| IRDIG27501 + IRDIG28684 | 84 + 23 | 6 | 80.2 | 7.6 | A | 96.0 | 5.0 | AB |
| IRDIG27501 + IRDIG28674 | 84 + 25 | 4 | 48.7 | 9.3 | ABC | 93.6 | 6.1 | AB |
| IRDIG27501 + IRDIG28692 | 84 + 42 | 4 | 61.0 | 9.3 | AB | 92.9 | 6.1 | AB |
| IRDIG27501 + IRDIG28672 | 84 + 22 | 4 | 54.2 | 9.3 | ABC | 86.3 | 6.1 | ABC |
| IRDIG27501 + IRDIG28680 | 84 + 42 | 4 | 27.7 | 9.3 | BCD | 84.7 | 6.1 | ABC |
| IRDIG27501 + IRDIG27642 | 84 + 42 | 10 | 39.9 | 5.9 | BC | 75.6 | 3.9 | BCD |
| IRDIG27501 + IRDIG28676 | 84 + 42 | 4 | 16.7 | 9.3 | BCD | 59.8 | 6.1 | CDE |
| IRDIG27501 + IRDIG28690 | 84 + 24 | 6 | 12.8 | 7.6 | CD | 53.9 | 5.0 | DE |
| IRDIG27501 + IRDIG28694 | 84 + 42 | 4 | 12.4 | 9.3 | CD | 47.7 | 6.1 | E |
| IRDIG27501 | 84 | 14 | 4.2 | 5.0 | D | 15.1 | 3.3 | F |

TABLE 7-continued

Mean percent practical mortality and mean percent growth inhibition of WCR when exposed to combinations of IRDIG27642 homologs with IRDIG27501 insecticidal proteins

| Sample name | Conc. (ug/cm2) | Rep | % Practical mortality | | | % Growth inhibition | | |
|---|---|---|---|---|---|---|---|---|
| | | | Mean | Std Error | Tukey HSD (P > 0.05)[a] | Mean | Std Error | Tukey HSD (P > 0.05)[a] |
| 10 mM CAPS pH 11 | 0 | 18 | 3.6 | 4.4 | D | 0.0 | 2.9 | F |
| 20 mM NaCitrate pH 3.5 | 0 | 18 | 5.6 | 4.4 | D | 0.0 | 2.9 | F |

[a] Letters designate statistical levels. Levels not connected by same letter are significantly different according to ANOVA and mean separations with Tukey HSD (p > 0.05).

TABLE 8

Potentiation effect of IRDIG27501 on homologs of IRDIG27642 against the % practical mortality of WCR

| IRDIG | Homologs of IRDIG27642 | Conc. of IRDIG27501 | Conc. of IRDIG27642 homologs | % Practical mortality | | | | t-test analysis of % Practical mortality [a] | | |
|---|---|---|---|---|---|---|---|---|---|---|
| | | | | IRDIG27501 alone or IRDIG27642 homologs alone | | Mixture of IRDIG27642 homologs and IRDIG27501 | | # of fold difference of mixture to single | T-test status | T-test Pr value |
| | | | | Mean | Std Error | Mean | Std Error | | | |
| 27501 | None | 84 | 0 | 4.2 | 1.4 | NA | NA | NA | NA | NA |
| 27501 | 27642 | 84 | 42 | 9.5 | 9.3 | 39.9 | 8.3 | 4.2 | * | 0.0269 |
| 27501 | 28672 | 84 | 22 | 3.1 | 8.1 | 54.2 | 8.1 | 17.3 | * | 0.0043 |
| 27501 | 28674 | 84 | 25 | 11.8 | 6.7 | 48.7 | 6.7 | 4.1 | * | 0.0080 |
| 27501 | 28680 | 84 | 42 | 21.1 | 14.1 | 27.7 | 14.1 | 1.3 | ns | 0.7534 |
| 27501 | 28682 | 84 | 42 | 26.8 | 8.7 | 93.4 | 8.7 | 3.5 | * | 0.0016 |
| 27501 | 28684 | 84 | 23 | 35.8 | 7.4 | 80.2 | 7.4 | 2.2 | * | 0.0017 |
| 27501 | 28686 | 84 | 42 | 50.3 | 7.2 | 93.7 | 8.8 | 1.9 | * | 0.0051 |
| 27501 | 28688 | 84 | 42 | 49.7 | 8.6 | 93.5 | 10.5 | 1.9 | * | 0.0122 |
| 27501 | 28690 | 84 | 24 | 1.0 | 3.5 | 12.8 | 3.5 | 12.4 | * | 0.0395 |
| 27501 | 28692 | 84 | 42 | 9.6 | 8.5 | 61.0 | 8.5 | 6.4 | * | 0.0053 |
| 27501 | 28676 | 84 | 42 | 5.4 | 4.1 | 16.7 | 4.1 | 3.1 | * | 0.0943 |
| 27501 | 28694 | 84 | 42 | 4.9 | 4.6 | 12.4 | 4.6 | 2.5 | ns | 0.2912 |

[a] Means of IRDIG27501 and homologs of IRDIG27642 alone, and compared to mixtures of both IRDIG27501 and homologs of IRDIG27642 within a row are not significantly (ns) different according to t-test (Pr > 0.1).
* denotes a significant response with a similar statistical analysis.

TABLE 9

Potentiation effect of IRDIG27501 on homologs of IRDIG27642 against the % growth inhibition of WCR

| IRDIG | Homologs of IRDIG27642 | Conc. of IRDIG27501 | Conc. of IRDIG27642 homologs | % growth inhibition | | | | t-test analysis of % growth inhibition [a] | | |
|---|---|---|---|---|---|---|---|---|---|---|
| | | | | IRDIG27501 alone or IRDIG27642 homologs alone | | Mixture of IRDIG27642 homologs and IRDIG27501 | | # of fold difference of mixture to single | T-test status | T-test Pr value |
| | | | | Mean | Std Error | Mean | Std Error | | | |
| 27501 | None | 84 | 0 | 15.1 | 4.0 | NA | NA | NA | NA | NA |
| 27501 | 27642 | 84 | 42 | 30.6 | 7.8 | 75.6 | 7.0 | 2.5 | * | 0.0006 |
| 27501 | 28672 | 84 | 22 | 34.2 | 6.0 | 86.3 | 6.0 | 2.5 | * | 0.0009 |
| 27501 | 28674 | 84 | 25 | 61.4 | 6.5 | 93.6 | 6.5 | 1.5 | * | 0.0127 |
| 27501 | 28680 | 84 | 42 | 56.5 | 11.3 | 84.7 | 11.3 | 1.5 | ns | 0.1289 |
| 27501 | 28682 | 84 | 42 | 69.5 | 5.0 | 99.8 | 5.0 | 1.4 | * | 0.0054 |
| 27501 | 28684 | 84 | 23 | 79.2 | 4.6 | 96.0 | 4.6 | 1.2 | * | 0.0278 |

TABLE 9-continued

Potentiation effect of IRDIG27501 on homologs of IRDIG27642 against the % growth inhibition of WCR

| | | | | % growth inhibition | | | | | |
|---|---|---|---|---|---|---|---|---|---|
| | | | | IRDIG27501 alone or IRDIG27642 homologs alone | | Mixture of IRDIG27642 homologs and IRDIG27501 | | t-test analysis of % growth inhibition [a] | |
| IRDIG | Homologs of IRDIG27642 | Conc. of IRDIG27501 | Conc. of IRDIG27642 homologs | Mean | Std Error | Mean | Std Error | # of fold difference of mixture to single | T-test status | T-test Pr value |
|---|---|---|---|---|---|---|---|---|---|---|
| 27501 | 28686 | 84 | 42 | 79.1 | 4.1 | 100.0 | 5.0 | 1.3 | * | 0.0121 |
| 27501 | 28688 | 84 | 42 | 69.3 | 9.7 | 98.9 | 11.8 | 1.4 | * | 0.0885 |
| 27501 | 28690 | 84 | 24 | 10.9 | 10.0 | 53.9 | 10.0 | 4.9 | * | 0.0127 |
| 27501 | 28692 | 84 | 42 | 24.4 | 10.1 | 92.9 | 10.1 | 3.8 | * | 0.0030 |
| 27501 | 28676 | 84 | 42 | 24.4 | 7.5 | 59.8 | 7.5 | 2.4 | * | 0.0154 |
| 27501 | 28694 | 84 | 42 | 16.3 | 11.5 | 47.7 | 11.5 | 2.9 | ns | 0.1028 |

[a] Means of IRDIG27501 and homologs of IRDIG27642 alone, and compared to mixtures of both IRDIG27501 and homologs of IRDIG27642 within a row are not significantly (ns) different according to t-test (Pr > 0.1).
* denotes a significant response with a similar statistical analysis.

IRDIG27642 and IRDIG28686 were tested in a range of concentrations from 2.6 to 168 $\mu g/cm^2$ and the resultant WCR activity provided sufficient data for dose response analyses (Tables 10 and 11). There was a significant difference in percent practical mortality of IRDIG28686 at doses of 21, 42, 84, and 168 $\mu g/cm^2$ relative to the negative control. Significant growth inhibition was determined for IRDIG27642 at doses of 10.5, 42, 84, 168 $\mu g/cm^2$ and for IRDIG28686 at 21, 42, 84, and 168 $\mu g/cm^2$.

TABLE 10

Dose response of insecticidal proteins IRDIG27642 and IRDIG28686 against WCR in a 48 well bioassay format

| | | | % Practical mortality | | | % Growth inhibition | | |
|---|---|---|---|---|---|---|---|---|
| Sample name | Conc. (ug/cm2) | Rep | Mean | Std Error | Tukey HSD (P > 0.05) [a] | Mean | Std Error | Tukey HSD (P > 0.05) [a] |
| 10 mM CAPS buffer pH 11 | 0 | 8 | 2.5 | 3.1 | E | 2.2 | 6.0 | FG |
| 20 mM Sodium citrate buffer pH 3.5 | 0 | 8 | 6.9 | 3.1 | DE | 0.0 | 6.0 | G |
| Cry34/35Ab1 | 100 | 8 | 98.3 | 3.1 | A | 99.8 | 6.0 | A |
| IRDIG27642 | 2.625 | 4 | 0.0 | 4.4 | E | 9.6 | 8.4 | EFG |
| IRDIG27642 | 5.25 | 4 | 7.2 | 4.4 | DE | 31.2 | 8.4 | CDEFG |
| IRDIG27642 | 10.5 | 4 | 10.1 | 4.4 | DE | 40.3 | 8.4 | CDE |
| IRDIG27642 | 21 | 4 | 7.5 | 4.4 | DE | 38.3 | 8.4 | CDEF |
| IRDIG27642 | 42 | 4 | 9.2 | 4.4 | DE | 53.0 | 8.4 | BCD |
| IRDIG27642 | 84 | 4 | 7.6 | 4.4 | DE | 41.2 | 8.4 | CDE |
| IRDIG27642 | 168 | 4 | 21.8 | 4.4 | CDE | 57.6 | 8.4 | BCD |
| IRDIG28686 | 2.625 | 2 | 3.2 | 6.2 | DE | 4.9 | 11.9 | DEFG |
| IRDIG28686 | 5.25 | 4 | 10.1 | 4.4 | DE | 24.9 | 8.4 | CDEFG |
| IRDIG28686 | 10.5 | 4 | 17.2 | 4.4 | DE | 34.0 | 8.4 | CDEFG |
| IRDIG28686 | 21 | 4 | 25.4 | 4.4 | CD | 50.8 | 8.4 | BCDE |
| IRDIG28686 | 42 | 4 | 42.8 | 4.4 | BC | 65.5 | 8.4 | ABC |
| IRDIG28686 | 84 | 4 | 48.9 | 4.4 | B | 61.6 | 8.4 | BC |
| IRDIG28686 | 168 | 4 | 65.3 | 4.4 | B | 86.2 | 8.4 | AB |

[a] Means followed by the same letter within each column are not significantly different according to Tukey HSD (p > 0.05).

TABLE 11

LC$_{50}$ and GI$_{50}$ of IRDIG27642 and IRDIG28686 insecticidal
IRDIG proteins in 48-well bioassay format

| Protein | LC$_{50}$, µg/cm$^2$ (95% CI*) | GI$_{50}$, µg/cm$^2$ (95% CI*) |
|---|---|---|
| IRDIG28686 | 78.4 (58.0-116.6) | 22.6 (11.4-44.7) |
| IRDIG27642 | >168 | 74.2 (25.2-218.1) |

*CI = Confidence interval

IRDIG27642 and IRDIG28686 were tested in a range of concentrations from 2.625 to 168 µg/cm$^2$ in combinations with IRDIG27501 respectively. For the combinations, each concentration of these 2 proteins was mixed with 126 µg/cm$^2$ of IRDIG27501 and the resultant WCR activity provided sufficient data for dose response analyses (Tables 12, 13 and 14). There was a significant difference in percent practical mortality of IRDIG28686 at doses of 10.5, 21, 42, 84, and 168 µg/cm$^2$. Significant growth inhibition was determined for IRDIG27642 and IRDIG28686 at all doses of 2.625, 5.25, 10.5, 42, 84, 168 µg/cm$^2$.

Table 12, 13 and 14 shows the dose response of insecticidal proteins against WCR in a 48 well bioassay.

TABLE 12

Insecticidal activity from different concentrations of
IRDIG27642 in mixture with 126 µg/cm$^2$ of IRDIG27501

| | | | % Practical Mortality | | | % Growth Inhibition | | |
|---|---|---|---|---|---|---|---|---|
| Sample name | Conc. (µg/cm$^2$) | Rep | Mean | Std Error | Tukey HSD (Pr > 0.05) | Mean | Std Error | Tukey HSD (Pr > 0.05) |
| 10 mM CAPS, pH 11 | 0 | 4 | 5 | 7.6 | B | 0.0 | 10.5 | D |
| 20 mm NaCitrate, pH 3.5 | 0 | 4 | 11.5 | 7.6 | B | 0.0 | 10.5 | D |
| IRDIG27501 | 126 | 4 | 6.3 | 7.6 | B | 26.4 | 10.5 | CD |
| Cry34/Cry35Ab1 | 100 | 4 | 98.4 | 7.6 | A | 100.0 | 10.5 | A |
| IRDIG27501 + IRDIG27642 | 126 + 2.625 | 4 | 14.5 | 7.6 | B | 41.8 | 10.5 | BCD |
| IRDIG27501 + IRDIG27642 | 126 + 5.25 | 4 | 19.9 | 7.6 | B | 57.4 | 10.5 | ABC |
| IRDIG27501 + IRDIG27642 | 126 + 10.5 | 4 | 16.2 | 7.6 | B | 52.2 | 10.5 | ABC |
| IRDIG27501 + IRDIG27642 | 126 + 21 | 4 | 32.4 | 7.6 | B | 76.3 | 10.5 | ABC |
| IRDIG27501 + IRDIG27642 | 126 + 42 | 4 | 19.8 | 7.6 | B | 58.6 | 10.5 | ABC |
| IRDIG27501 + IRDIG27642 | 126 + 84 | 4 | 31.6 | 7.6 | B | 78.9 | 10.5 | AB |
| IRDIG27501 + IRDIG27642 | 126 + 168 | 4 | 28.9 | 7.6 | B | 74.3 | 10.5 | ABC |

Means followed by the same letter within each column are not significantly different according to Tukey HSD (Pr > 0.05).

TABLE 13

Insecticidal activity from different concentrations of
IRDIG28686 in mixture with 126 µg/cm2 of IRDIG27501

| | | | % Practical Mortality | | | % Growth Inhibition | | |
|---|---|---|---|---|---|---|---|---|
| Sample name | Conc. (µg/cm$^2$) | Rep | Mean | Std Error | Tukey HSD (Pr > 0.05) | Mean | Std Error | Tukey HSD (Pr > 0.05) |
| 10 mM CAPS pH 11 | 0 | 4 | 0 | 9.8 | D | 4.4 | 7.0 | C |
| 20 mM NaCitrate pH 3.5 | 0 | 4 | 2.4 | 9.8 | D | 0.0 | 7.0 | C |
| Cry34/35Ab1 | 100 | 4 | 98.1 | 9.8 | A | 99.6 | 7.0 | A |
| IRDIG27501 | 126 | 6 | 35.3 | 8.0 | CD | 42.3 | 5.7 | B |
| IRDIG27501 + IRDIG28686 | 126 + 2.625 | 2 | 26 | 13.9 | BCD | 77.9 | 10.0 | AB |
| IRDIG27501 + IRDIG28686 | 126 + 5.25 | 4 | 32.6 | 9.8 | CD | 71.9 | 7.0 | AB |
| IRDIG27501 + IRDIG28686 | 126 + 10.5 | 4 | 55.8 | 9.8 | ABC | 80.7 | 7.0 | A |
| IRDIG27501 + IRDIG28686 | 126 + 21 | 4 | 68.5 | 9.8 | ABC | 92.5 | 7.0 | A |
| IRDIG27501 + IRDIG28686 | 126 + 42 | 4 | 83.6 | 9.8 | AB | 97.3 | 7.0 | A |
| IRDIG27501 + IRDIG28686 | 126 + 84 | 4 | 85.4 | 9.8 | A | 96.7 | 7.0 | A |

TABLE 13-continued

Insecticidal activity from different concentrations of
IRDIG28686 in mixture with 126 μg/cm2 of IRDIG27501

| | | | % Practical Mortality | | | % Growth Inhibition | | |
|---|---|---|---|---|---|---|---|---|
| Sample name | Conc. (μg/cm²) | Rep | Mean | Std Error | Tukey HSD (Pr > 0.05) | Mean | Std Error | Tukey HSD (Pr > 0.05) |
| IRDIG27501 + IRDIG28686 | 126 + 168 | 4 | 87 | 9.8 | A | 98.3 | 7.0 | A |

Means followed by the same letter within each column are not significantly different according to Tukey HSD (Pr > 0.05).

TABLE 14

$LC_{50}$ and $GI_{50}$ of insecticidal proteins IRDIG27642 or IRDIG28686
in combinations with IRDIG27501 in 48-well bioassay

| Protein mixture with IRDIG27501[a] | $LC_{50}$, μg/cm² (95% CI[b]) | $GI_{50}$, μg/cm² (95% CI[b]) |
|---|---|---|
| IRDIG27642 | >168 (not available) | 4.1 (1.0-16.1) |
| IRDIG28686 | 8.7 (5.7-12.2) | 2.3 (1.3-4.0) |

[a]126 μg/cm² of IRDIG27501 was tested in mixture with each concentration of IRDIG27642 or IRDIG28686. Tested concentrations of IRDIG27642 or IRDIG28686 were between 2.625 to 168 μg/cm².
[b]CI = Confidence interval Addition of IRDIG27501 at 126 μg/cm² for combination with IRDIG28686 and IRDIG27642 provided 9-fold or 18-fold increase in potency of IRDIG28686 or IRDIG27642 respectively, when compared with the $LC_{50}$ and $GI_{50}$ values of these proteins tested alone in Table 11.

Example 7

Insecticidal Activity of Proteins on Resistant WCR

The insecticidal proteins were bioassayed with larvae generated from a selected and a non-selected Cry3Bb WCR strain, as well as a non-diapausing WCR control line. The non-diapausing WCR control eggs (Crop Characteristics Inc., Farmington, Minn.), Cry3Bb selected WCR eggs (Meihls et al., 2008 and 2012) and Cry3Bb non-selected WCR eggs are processed similarly as described above in preparation for a 48-well bioassay format. The Cry3Bb non-selected eggs are an unexposed lab population, originating from Brookings, S. Dak.

Treatments included 223 (total estimation) crystals/spores mixtures of DBt12172_00709 B.t. culture containing both 181 μg/cm² IRDIG27501.1 and 42 μg/cm² IRDIG27642.1. 4Q7, a B.t. host, was included as a negative control of DBt12172_00709. Positive and negative controls were 100 μg/cm² Cry34/35Ab1 and 20 mM sodium citrate, pH3.5 buffer respectively. 300 μg/cm² of truncated Cry3Aa was included to provide an indication of the resistance level of the Cry3Bb selected and non-selected WCR. 10 mM CAPS pH 10.5 buffer was included as a buffer negative control of the truncated Cry3Aa.

The results (Table 15) indicate that the binary IRDIG27501/27642 proteins provided 33.1% practical mortality and 71.8% growth inhibition on Cry3Bb-selected WCR neonates. The WCR larval sensitivity was not significantly different against this binary protein, comparing the Cry3Bb selected and non-selected strains, as well as the non-diapause WCR control strain (percent practical mortality and growth inhibition at 9-33% and 66-72% respectively). These data suggest that the binary proteins IRDIG27501/27642 has a different mode of action than Cry3Bb protein. The non-selected Cry3Bb strain is a little less susceptible to mCry3Aa and this observation concur with results presented in Zukoff et al. 2015.

TABLE 15

Sensitivity of non-diapause WCR control strain, Cry3Bb-selected and non-selected WCR strains against
the Crystal/spore mixture of DBt12172 B.t. culture containing IRDIG27501.1 and IRDIG27642.1

| | | | % Practical Mortality | | | % Growth Inhibition | | |
|---|---|---|---|---|---|---|---|---|
| Treatment | Concentration (μg/cm²) | Insect Strain | Mean | Tukey HSD (Pr > 0.5) * | Std Err | Mean | Tukey HSD (Pr > 0.5) * | Std Err |
| 20 mM Sodium Citrate. pH 3.5 | 0 | Cry3Bb non-selected WCR | 0 | F | 0 | 0 | B | 0 |
| | | Cry3Bb selected WCR | 3.4 | EF | 1.9 | 0 | B | 0 |
| | | Non diapause WCR control | 0 | F | 0 | 0 | B | 0 |
| Cry34/35Ab1 | 100 | Cry3Bb non-selected WCR | 46.7 | BC | 8.0 | 89.9 | A | 1.8 |
| | | Cry3Bb selected WCR | 71.5 | AB | 15.5 | 94.0 | A | 2.1 |
| | | Non diapause WCR control | 94.2 | A | 5.8 | 99.6 | A | 0.5 |
| 10 mM CAPS buffer pH 10.5 | 0 | Cry3Bb non-selected WCR | 0 | F | 0 | 0 | B | 0 |
| | | Cry3Bb selected WCR | 0 | F | 0 | 0 | B | 0 |
| | | Non diapause WCR control | 0 | F | 0 | 0 | B | 0 |

TABLE 15-continued

Sensitivity of non-diapause WCR control strain, Cry3Bb-selected and non-selected WCR strains against the Crystal/spore mixture of DBt12172 B.t. culture containing IRDIG27501.1 and IRDIG27642.1

|  |  |  | % Practical Mortality | | % Growth Inhibition | |
|---|---|---|---|---|---|---|
| Treatment | Concentration ($\mu g/cm^2$) | Insect Strain | Tukey HSD Mean (Pr > 0.5) * | Std Err | Tukey HSD Mean (Pr > 0.5) * | Std Err |
| DIG-409 (Truncated Cry3Aa) | 300 | Cry3Bb non-selected WCR | 3.1 EF | 3.1 | −32.0 B | 15.8 |
| | | Cry3Bb selected WCR | 11.0 DEF | 7.3 | −18.2 B | 22.8 |
| | | Non diapause WCR control | 41.4 BCD | 10.2 | 65.1 A | 6.9 |
| 4Q7 | 0 | Cry3Bb non-selected WCR | 0 F | 0 | 0 B | 0 |
| | | Cry3Bb selected WCR | 0 F | 0 | 0 B | 0 |
| | | Non diapause WCR control | 0 F | 0 | 0 B | 0 |
| DBt12172 (IRDIG27501.1 + IRDIG27642.1) | Estimated at 181 + 42 = 223 | Cry3Bb non-selected WCR | 9.0 DEF | 4.9 | 67.3 A | 3.3 |
| | | Cry3Bb selected WCR | 33.1 CDE | 10.8 | 71.8 A | 4.0 |
| | | Non diapause WCR control | 16.0 CDEF | 7.4 | 66.5 A | 3.2 |

* Means follow by a same letter within a column are not significantly different according to ANOVA and Tukey HSD (Pr > 0.05)

Percent practical mortality (dead plus moribund insects) and growth inhibition are calculated. Control mortality should not exceed 20%. Bioassays are conducted under completely randomized design and replicated 3-4 times, with 16 *D. virgifera virgifera* larvae per replicate. Percent practical mortality and growth inhibition are analyzed with a one-way analysis of variance (ANOVA) and mean separations by using the Tukey-Kramer HSD test (P>0.05).

Example 8

Protein Processing by WCR Midgut Fluid and Corn Root Juice

Midgut fluid collection. Approximately 150 third instar western corn rootworm (WCR) larvae were ordered from Crop Characteristics. The insects were shipped with corn roots. Under a light microscope, using a scalpel, both the posterior and anterior ends of the larvae were removed. Using forceps, the gut was pulled out and stored in buffer (0.15 M NaCl filtered and sterile buffer containing 8.5% sucrose) and kept on ice.

Procedure for Protein Digestion by WCR Midgut Fluid.

Western corn rootworm (WCR) active protein stability was analyzed in the presence of 12 μg WCR gut juice to determine potential cleavage (activation or inactivation) sites. Proteins expressed and purified from *Pseudomonas* were incubated with WCR gut juice or extract for 20 hr at 30° C. WCR concentrations and pH of 7.5 (50 mM Tris pH 7.5, 0.15 M KCl, 0.015 M $CaCl_2$ final concentration from 10× stock) were chosen based on protease activity testing.

Reactions were stopped with the addition of proteinase inhibitors. Thirty μl of reaction was then mixed 10 μl of LDS buffer (10 mM TCEP) and loaded onto a 4-12% PAGE gel using MES running buffer. Results indicate a significant amount of processing of WCR actives by WCR and maize root extract (MRE). Identical gels were blotted to allow identification of cleavage motifs by Edman N-terminal sequencing and intact MS analysis. The core protein was then expressed in *E. coli* for WCR activity test and other characterizations.

Procedure for Protein Digestion by Corn Root Juice 100 ug/$cm^2$ of insecticidal IRDIG27642 core proteins expressed and purified from recombinant *E. coli* are tested alone and in combination with IRDIG27501 against the WCR following the bioassay method of 48-well format, described in Example 5, Insecticidal activity of proteins.

Example 9

*Agrobacterium* Transformation

Standard cloning methods were used in the construction of binary plant transformation and expression plasmid. Restriction endonucleases and T4 DNA Ligase were obtained from NEB. Plasmid preparations were performed using the NucleoSpin® Plasmid Preparation kit or the NucleoBond® AX Xtra Midi kit (both from Macherey-Nagel), following the instructions of the manufacturers. DNA fragments were purified using the QIAquick PCR Purification Kit or the QIAEX II Gel Extraction Kit (both from Qiagen) after gel isolation.

DNA comprising a nucleotide sequence that encodes an insecticidal protein was synthesized by a commercial vendor (e.g., DNA2.0, Menlo Park, Calif.) and was supplied as cloned fragments in plasmid vectors. Other DNA sequences encoding other insecticidal proteins were obtained by standard molecular biology manipulation of constructs containing appropriate nucleotide sequences.

Full-length or modified coding sequences (CDS) for insecticidal proteins were subcloned into a plant expression plasmid at appropriate sites. The resulting plant expression cassettes containing the appropriate coding region under the control of plant expression elements (e.g., plant expressible promoters, 3' terminal transcription termination and polyadenylate addition determinants, and the like) were subcloned into a binary vector plasmid, utilizing, for example, Gateway® technology or standard restriction enzyme fragment cloning procedures. LR Clonase™ (Invitrogen) for example, may be used to recombine the full-length and modified gene plant expression cassettes into a binary plant transformation plasmid if the Gateway® technology is utilized. The binary plant transformation vector included a bacterial selectable marker gene that confers resistance to the antibiotic spectinomycin when the plasmid is present in *E. coli* and *Agrobacterium* cells. The binary vector plasmid also included a plant-expressible selectable marker gene that is functional in the desired host plants, namely, the aminoglycoside phosphotransferase gene of transposon Tn5 (aphII) which encodes resistance to the antibiotics kanamycin, neomycin and G418.

Electro-competent cells of *Agrobacterium tumefaciens* strain Z707S (a streptomycin-resistant derivative of Z707) were prepared and transformed using electroporation (Weigel and Glazebrook, 2002). After electroporation, 1 mL of YEP broth (gm/L: yeast extract, 10; peptone, 10; NaCl, 5) was added to the cuvette and the cell-YEP suspension was transferred to a 15 mL culture tube for incubation at 28° C. in a water bath with constant agitation for 4 hours. The cells were plated on YEP plus agar (25 gm/L) with spectinomycin (200 μg/mL) and streptomycin (250 μg/mL) and the plates were incubated for 2-4 days at 28° C. Well separated single colonies were selected and streaked onto fresh YEP+agar plates with spectinomycin and streptomycin, and incubated at 28° C. for 1-3 days.

The presence of the insecticidal toxin gene insert in the binary plant transformation vector was performed by PCR analysis using vector-specific primers with template plasmid DNA prepared from selected *Agrobacterium* colonies. The cell pellet from a 4 mL aliquot of a 15 mL overnight culture grown in YEP with spectinomycin and streptomycin as before was extracted using Qiagen Spin Mini Preps, performed per manufacturer's instructions. Plasmid DNA from the binary vector used in the *Agrobacterium* electroporation transformation was included as a control. The PCR reaction was completed using Taq DNA polymerase from Invitrogen per manufacturer's instructions at 0.5× concentrations. PCR reactions were carried out in a MJ Research Peltier Thermal Cycler programmed with the following conditions: Step 1) 94° C. for 3 minutes; Step 2) 94° C. for 45 seconds; Step 3) 55° C. for 30 seconds; Step 4) 72° C. for 1 minute per kb of expected product length; Step 5) 29 times to Step 2; Step 6) 72° C. for 10 minutes. The reaction was maintained at 4° C. after cycling. The amplification products were analyzed by agarose gel electrophoresis (e.g., 0.7% to 1% agarose, w/v) and visualized by ethidium bromide staining. A colony was selected whose PCR product was identical to the plasmid control.

Another binary plant transformation vector containing the insecticidal toxin gene insert was performed by restriction digest fingerprint mapping of plasmid DNA prepared from candidate *Agrobacterium* isolates by standard molecular biology methods well known to those skilled in the art of *Agrobacterium* manipulation.

The foregoing discloses nucleic acid constructs comprising a polynucleotide that encodes an insecticidal toxin polypeptide in accordance with the invention.

Example 10

Production of Insecticidal Toxins in Dicot Plants

*Arabidopsis* Transformation.

*Arabidopsis thaliana* Col-01 is transformed using the floral dip method (Weigel and Glazebrook, 2002). The selected *Agrobacterium* colony is used to inoculate 1 mL to 15 mL cultures of YEP broth containing appropriate antibiotics for selection. The culture is incubated overnight at 28° C. with constant agitation at 220 rpm. Each culture is used to inoculate two 500 mL cultures of YEP broth containing appropriate antibiotics for selection and the new cultures are incubated overnight at 28° C. with constant agitation. The cells are pelleted at approximately 8700×g for 10 minutes at room temperature, and the resulting supernatant is discarded. The cell pellet is gently resuspended in 500 mL of infiltration media containing: ½× Murashige and Skoog salts (Sigma-Aldrich)/Gamborg's B5 vitamins (Gold BioTechnology, St. Louis, Mo.), 10% (w/v) sucrose, 0.044 μM benzylaminopurine (10 μL/liter of 1 mg/mL stock in DMSO) and 300 μL/liter Silwet L-77. Plants approximately 1 month old are dipped into the media for 15 seconds, with care taken to assure submergence of the newest inflorescence. The plants are then laid on their sides and covered (transparent or opaque) for 24 hours, washed with water, and placed upright. The plants are grown at 22° C., with a 16-hour light/8-hour dark photoperiod. Approximately 4 weeks after dipping, the seeds are harvested.

*Arabidopsis* Growth and Selection.

Freshly harvested T1 seed is allowed to dry for at least 7 days at room temperature in the presence of desiccant. Seed is suspended in a 0.1% agar/water (Sigma-Aldrich) solution and then stratified at 4° C. for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) is covered with fine vermiculite, sub-irrigated with Hoagland's solution until wet, then allowed to drain for 24 hours. Stratified seed is sown onto the vermiculite and covered with humidity domes (KORD Products, Bramalea, Ontario, Canada) for 7 days. Seeds are germinated and plants are grown in a Conviron™ growth chamber (Models CMP4030 or CMP3244; Controlled Environments Limited, Winnipeg, Manitoba, Canada) under long day conditions (16 hours light/8 hours dark) at a light intensity of 120-150 $\mu mol/m^2$ sec under constant temperature (22° C.) and humidity (40-50%). Plants are initially watered with Hoagland's solution and subsequently with deionized water to keep the soil moist but not wet.

The domes are removed 5-6 days post sowing and plants are sprayed with a chemical selection agent to kill plants germinated from nontransformed seeds. For example, if the plant expressible selectable marker gene provided by the binary plant transformation vector is a bar gene, transformed plants may be selected by spraying with a 1000× solution of Finale (5.78% glufosinate ammonium, Farnam Companies Inc., Phoenix, Ariz.). Two subsequent sprays are performed at 5-7 day intervals. Survivors (plants actively growing) are identified 7-10 days after the final spraying and transplanted into pots prepared with Sunshine Mix LP5. Transplanted plants are covered with a humidity dome for 3-4 days and placed in a Conviron™ growth chamber under the above-mentioned growth conditions.

Those skilled in the art of dicot plant transformation will understand that other methods of selection of transformed plants are available when other plant expressible selectable marker genes (e.g., herbicide tolerance genes) are used.

Insect Bioassays of Transgenic *Arabidopsis*.

Transgenic *Arabidopsis* lines expressing insecticidal toxin proteins are demonstrated to be active against sensitive insect species in artificial diet overlay assays. Protein extracted from transgenic and non-transgenic *Arabidopsis* lines is quantified by appropriate methods and sample volumes are adjusted to normalize protein concentration. Bioassays are conducted on artificial diet as described above.

Non-transgenic *Arabidopsis* and/or buffer and water are included in assays as background check treatments.

The foregoing provides methods for making and using transgenic plants comprising insecticidal toxin polypeptides according to the invention.

Example 11

Production of Insecticidal Proteins in Monocot Plants

*Agrobacterium*-Mediated Transformation of Maize.

Transgenic maize cells, tissues, and plants that produce one or more insecticidal proteins through expression of a chimeric gene stably-integrated into the plant genome are produced following *Agrobacterium*-mediated transformation. Maize transformation methods employing binary transformation vectors are known in the art, as described, for example, in U.S. Pat. No. 8,304,604, which is herein incorporated by reference in its entirety. Transformed tissues are selected by their ability to grow on Haloxyfop-containing medium and are screened for protein production, as appropriate. Portions of such transformed tissue cultures are presented to insect larvae for bioassay, essentially as described in EXAMPLE 5.

*Agrobacterium* Culture Initiation.

Glycerol stocks of the project vectors in the host *Agrobacterium tumefaciens* strain DAt13192 (RecA minus ternary strain) are obtained from the DAS Recombinant Culture Collection (RCC). *Agrobacterium* cultures are streaked from glycerol stocks onto AB minimal medium and incubated at 20° C. in the dark for 3 days. *Agrobacterium* cultures are then streaked onto a plate of YEP medium and incubated at 20° C. in the dark for 1 day.

On the day of an experiment, a mixture of Inoculation medium and acetosyringone is prepared in a volume appropriate to the number of constructs in the experiment. Inoculation medium is pipetted into a sterile, disposable, 250 ml flask. A 1 M stock solution of acetosyringone in 100% dimethyl sulfoxide is added to the flask containing inoculation medium in a volume appropriate to make a final acetosyringone concentration of 200 μM.

For each construct, 1-2 loops of *Agrobacterium* from the YEP plate are suspended in 15 mL of the inoculation medium/acetosyringone mixture inside a sterile, disposable, 50 mL centrifuge tube and the optical density of the solution at 600 nm (O.D.$_{600}$) is measured in a spectrophotometer. The suspension is then diluted down to 0.25-0.35 O.D.$_{600}$ using additional Inoculation medium/acetosyringone mixture. The tube of *Agrobacterium* suspension is then placed horizontally on a platform shaker set at about 75 rpm at room temperature for between 1 and 4 hours before use.

Ear Sterilization and Embryo Isolation.

Ears from *Zea mays* cultivar B104 are produced in greenhouse facilities and harvested 10-12 days post pollination. Harvested ears are de-husked and surface-sterilized by immersion in a 20% solution of commercial bleach (Ultra Clorox® Germicidal Bleach, 6.15% sodium hypochlorite) and two drops of soap, for 20 minutes, followed by three rinses in sterile, deionized water inside a laminar flow hood. Immature zygotic embryos (1.8-2.2 mm long) are aseptically excised from each ear and distributed into one or more micro-centrifuge tubes containing 2.0 mL of *Agrobacterium* suspension into which 2 μl of 10% Break-Thru® S233 surfactant has been added.

*Agrobacterium* Co-Cultivation.

Upon completion of the embryo isolation activity the tube of embryos is closed and placed on a rocker platform for 5 minutes. The contents of the tube are then poured out onto a plate of co-cultivation medium and the liquid *Agrobacterium* suspension is removed with a sterile, disposable, transfer pipette and the embryos are oriented with the scutellum facing up using a microscope. The plate is then closed, sealed with 3M Micropore tape, and placed in an incubator at 25° C. with 24 hours/day light at approximately 60 μmol m$^{-2}$ s$^{-1}$ photosynthetically active radiation (PAR).

Callus Selection and Regeneration of Transgenic Events.

Following the co-cultivation period, embryos are transferred to Resting medium. No more than 36 embryos are moved to each plate. The plates are incubated at 27° C. with 24 hours/day light at approximately 50 μmol m$^{-2}$ s$^{-1}$ PAR for 7-10 days. Callused embryos are then transferred onto Selection I medium. No more than 18 callused embryos are moved to each plate of Selection I. The plates are incubated at 27° C. with 24 hours/day light at approximately 50 μmol m$^{-2}$ s$^{-1}$ PAR for 7 days. Callused embryos are then transferred to Selection II medium. No more than 12 callused embryos are moved to each plate of Selection II. The plates are incubated at 27° C. with 24 hours/day light at approximately 50 μmol m$^{-2}$ s$^{-1}$ PAR for 14 days.

At this stage resistant calli are moved to Pre-Regeneration medium. No more than 9 calli are moved to each plate of Pre-Regeneration. The plates are held at 27° C. with 24 hours/day light at approximately 50 μmol m$^{-2}$ s$^{-1}$ PAR for 7 days. Regenerating calli are then transferred to Regeneration medium in Phytatrays™ (Sigma-Aldrich). and incubated at 28° C. with 16 hours light/8 hours dark per day at approximately 150 μmol m$^{-2}$ s$^{-1}$ PAR for 7-14 days or until shoots develop. No more than 5 calli are placed in each Phytatray™. Small shoots with primary roots are then isolated and transferred to Shoot/Root medium. Rooted plantlets about 6 cm or taller are transplanted into soil and moved out to a growth chamber for hardening off.

Transformed plant shoots selected by their ability to grow on medium containing Haloxyfop are transplanted from Phytatrays™ to small pots filled with growing medium (ProMix BX; Premier Tech Horticulture), covered with cups or HUMI-DOMES (Arco Plastics), and then hardened-off in a Conviron growth chamber (27° C. day/24° C. night, 16-hour photoperiod, 50-70% RH, 200 μmol m$^{-2}$s$^{-1}$ PAR). In some instances, putative transgenic plantlets are analyzed for transgene relative copy number by quantitative real-time PCR assays using primers designed to detect the herbicide tolerance gene integrated into the maize genome. Further, RNA qPCR assays are used to detect the presence of the linker sequence in expressed dsRNAs of putative transformants. Selected transformed plantlets are then moved into a greenhouse for further growth and testing.

Transfer and Establishment of T$_0$ Plants in the Greenhouse for Bioassay and Seed Production.

Plants are transplanted from Phytatrays™ to small pots (T. O. Plastics, 3.5" SVD, 700022C) filled with growing media (Premier Tech Horticulture, ProMix BX, 0581 P) and covered with Humidomes to acclimate the plants. They are placed in a Conviron growth chamber (28° C./24° C., 16-hour photoperiod, 50-70% RH, 200 μmol m$^{-2}$ s$^{-1}$ PAR) until they reach the V3-V4 stage. This aids in acclimating the plants to soil and harsher temperatures. Plants are then moved to the greenhouse (Light Exposure Type: Photo or Assimilation; High Light Limit: 1200 μmol m$^{-2}$ s$^{-1}$ PAR; 16-hour day length; 27° C. day/24° C. night) and transplanted from the small pots to TINUS™ 350-4 Rootrainers®

(Spencer-Lemaire Industries, Acheson, Alberta, Canada) prior to insect bioassay, at one plant per event per Rootrainer®. About 30 events are tested per construct. Approximately four days after transplanting to Rootrainers®, the V3-V4 stage plants are infested for bioassay, with about ready to hatch 150 western corn rootworm eggs (Crop Characteristics LLC, Farmington, Minn.) per plant. The bioassay is conducted for 2 weeks in the greenhouse and then, each event is graded following a modified method recommended by Oleson et al. (2005).

| ROOT DAMAGE RATING (modified from Oleson et al, 2005) | |
|---|---|
| 0.00 | No damage |
| 0.01 | Only a few minor feedings |
| 0.02 | Feeding scars evident - very light tunneling or channeling & no roots eaten off to within 4 cm of stalk (a root eaten to within 4 cm of the stalk is considered a "pruned root") |
| 0.05 | Severe scarring or when only the tips of several roots are injured on the entire root system |
| 0.10 | One root pruned |
| 0.25 | 2-3 roots pruned or ¼ of roots pruned |
| 0.50 | 4-5 roots pruned, considerable feeding damage on the outer portion of the root system; ½ of node pruned |
| 0.75 | 6+ roots pruned, but with extensive feeding on outer portion of the root system; ¾ of node pruned |
| 1.00 | At least one full node of roots pruned |

The inbred B104 and 7SH382 negative controls consistently provide 0.5 to 1.0 root ratings (high damage). $T_0$ events that provide 0.5 unit of root rating or less are saved and transplanted into 5 gallon pots for seed productions.

Plants of the $T_1$ generation are obtained by pollinating the silks of $T_0$ transgenic plants with pollen collected from plants of non-transgenic inbred line B104 or other appropriate pollen donors, and planting the resultant seeds. Reciprocal crosses are performed when possible. Selective $T_1$ events are tested for root protection against the western corn rootworm following the procedures used in $T_0$ event insect bioassay.

The foregoing provides methods for making and regenerating transgenic plants comprising insecticidal toxin polypeptides according to the invention.

Leaf Sampling for Western Blot Analyses.

Extraction Method. The plants are sampled at the V-3 to V-5 stage. Two 6 mm diameter leaf samples are stored in a 96 well cluster tube rack at −80° C. until the day of analysis. Two Daisy™ steel BB's and 300 µl of extraction buffer (PBS solution containing 0.05% of Tween 20 and 5 ul/ml of Sigma protease inhibitors, catalog number 9599) is added to each tube. The samples are milled in a Kelco bead mill for 3 minutes, on maximum setting. Samples are centrifuged at 3,000×g for 5 minutes; 100 µl of the supernatant is transferred to an empty sample tube. Another 100 µl of extraction buffer is added to the plant sample and bead milled 3 additional minutes, centrifuged and 100 µl of this extract is combined with the first 100 µl. The combined supernatants are mixed and analyzed the same day as the extraction.

Western Blot (Qualitative Methods):

Conventional electrophoresis and blotting methods are used with Invitrogen™ devices and basic reagents. A Dow AgroSciences rabbit anti-IRDIG27642 antibody is the primary antibody for the detection of IRDIG27642 in leaf tissue. All proteins are detected with a CY-3 fluorescence detection system.

Example 12

Bioassay of Transgenic Maize

Bioactivity of the insecticidal toxins produced in plant cells is demonstrated by conventional bioassay methods (see, for example Huang et al., 2006). In one assay of efficacy, various plant tissues or tissue pieces derived from a plant producing an insecticidal toxin are fed to target insects in a controlled feeding environment. In another bioactivity assay, protein extracts are prepared from various plant tissues derived from the plant producing the insecticidal toxin and the extracted proteins are incorporated into artificial diet bioassays. The results of each feeding assay are compared to similarly conducted bioassays that employ appropriate control tissues from host plants that do not produce an insecticidal toxin, or to other control samples.

Example 13

Transgenic *Glycine max* Comprising an Insecticidal Protein

Ten to 20 transgenic $T_0$ *Glycine max* plants harboring expression vectors for nucleic acids comprising an insecticidal protein are generated by *Agrobacterium*-mediated transformation. Mature soybean (*Glycine max*) seeds are sterilized overnight with chlorine gas for sixteen hours. Following sterilization with chlorine gas, the seeds are placed in an open container in a Laminar™ flow hood to dispel the chlorine gas. Next, the sterilized seeds are imbibed with sterile $H_2O$ for sixteen hours in the dark using a black box at 24° C.

Preparation of split-seed soybeans. The split soybean seed comprising a portion of an embryonic axis protocol required preparation of soybean seed material which is cut longitudinally, using a #10 blade affixed to a scalpel, along the hilum of the seed to separate and remove the seed coat, and to split the seed into two cotyledon sections. Careful attention is made to partially remove the embryonic axis, wherein about ½-⅓ of the embryo axis remains attached to the nodal end of the cotyledon.

Inoculation. The split soybean seeds comprising a partial portion of the embryonic axis are then immersed for about 30 minutes in a solution of *Agrobacterium tumefaciens* (e.g., strain EHA 101 or EHA 105) containing binary plasmid comprising an insecticidal protein. The *Agrobacterium tumefaciens* solution is diluted to a final concentration of $\lambda$=0.6 $OD_{650}$ before immersing the cotyledons comprising the embryo axis.

Co-cultivation. Following inoculation, the split soybean seed is allowed to co-cultivate with the *Agrobacterium tumefaciens* strain for 5 days on co-cultivation medium (Wang, Kan. *Agrobacterium Protocols*. 2. 1. New Jersey: Humana Press, 2006. Print.) in a Petri dish covered with a piece of filter paper.

Shoot induction. After 5 days of co-cultivation, the split soybean seeds are washed in liquid Shoot Induction (SI) media consisting of B5 salts, B5 vitamins, 28 mg/L Ferrous, 38 mg/L $Na_2EDTA$, 30 g/L sucrose, 0.6 g/L MES, 1.11 mg/L BAP, 100 mg/L TIMENTIN™, 200 mg/L cefotaxime, and 50 mg/L vancomycin (pH 5.7). The split soybean seeds are then cultured on Shoot Induction I (SI I) medium consisting of B5 salts, B5 vitamins, 7 g/L Noble agar, 28 mg/L Ferrous, 38 mg/L $Na_2EDTA$, 30 g/L sucrose, 0.6 g/L MES, 1.11 mg/L BAP, 50 mg/L TIMENTIN™, 200 mg/L cefotaxime, 50 mg/L vancomycin (pH 5.7), with the flat side of the cotyledon facing up and the nodal end of the cotyledon imbedded into the medium. After 2 weeks of culture, the explants from the transformed split soybean seed are transferred to the Shoot Induction II (SI II) medium containing SI I medium supplemented with 6 mg/L glufosinate (Liberty®).

Shoot elongation. After 2 weeks of culture on SI II medium, the cotyledons are removed from the explants and a flush shoot pad containing the embryonic axis are excised by making a cut at the base of the cotyledon. The isolated shoot pad from the cotyledon is transferred to Shoot Elongation (SE) medium. The SE medium consists of MS salts, 28 mg/L Ferrous, 38 mg/L Na$_2$EDTA, 30 g/L sucrose and 0.6 g/L MES, 50 mg/L asparagine, 100 mg/L L-pyroglutamic acid, 0.1 mg/L IAA, 0.5 mg/L GA3, 1 mg/L zeatin riboside, 50 mg/L TIMENTIN™, 200 mg/L cefotaxime, 50 mg/L vancomycin, 6 mg/L glufosinate, 7 g/L Noble agar, (pH 5.7). The cultures are transferred to fresh SE medium every 2 weeks. The cultures are grown in a Conviron™ growth chamber at 24° C. with an 18 h photoperiod at a light intensity of 80-90 µmol/m$^2$ sec.

Rooting. Elongated shoots which developed from the cotyledon shoot pad are isolated by cutting the elongated shoot at the base of the cotyledon shoot pad, and dipping the elongated shoot in 1 mg/L IBA (Indole 3-butyric acid) for 1-3 minutes to promote rooting. Next, the elongated shoots are transferred to rooting medium (MS salts, B5 vitamins, 28 mg/L Ferrous, 38 mg/L Na$_2$EDTA, 20 g/L sucrose and 0.59 g/L MES, 50 mg/L asparagine, 100 mg/L L-pyroglutamic acid 7 g/L Noble agar, pH 5.6) in phyta trays.

Cultivation. Following culture in a Conviron™ growth chamber at 24° C., 18 h photoperiod, for 1-2 weeks, the shoots which have developed roots are transferred to a soil mix in a covered sundae cup and placed in a Conviron™ growth chamber (models CMP4030 and CMP3244, Controlled Environments Limited, Winnipeg, Manitoba, Canada) under long day conditions (16 hours light/8 hours dark) at a light intensity of 120-150 µmol/m$^2$ sec under constant temperature (22° C.) and humidity (40-50%) for acclimatization of plantlets. The rooted plantlets are acclimated in sundae cups for several weeks before they are transferred to the greenhouse for further acclimatization and establishment of robust transgenic soybean plants.

Development and morphological characteristics of transgenic lines are compared with nontransformed plants. Plant root, shoot, foliage and reproduction characteristics are compared. There are no observable difference in root length and growth patterns of transgenic and nontransformed plants. Plant shoot characteristics such as height, leaf numbers and sizes, time of flowering, floral size and appearance are similar. In general, there are no observable morphological differences between transgenic lines and those without expression of IRDIG proteins when cultured in vitro and in soil in the glasshouse.

The foregoing provides methods for making and selecting transgenic dicot plants (soybeans) comprising insecticidal toxin polypeptides according to the invention.

Example 14

Transformation of Additional Crop Species

Cotton is transformed with insecticidal proteins (with or without a chloroplast transit peptide) to provide control of insects by utilizing a method known to those of skill in the art, for example, substantially the same techniques previously described in EXAMPLE 14 of U.S. Pat. No. 7,838,733, or Example 12 of PCT International Patent Publication No. WO 2007/053482.

BIBLIOGRAPHY

Beltz, G. A., Jacobs, K. A., Eickbush, T. H., Cherbas, P. T., Kafatos, F. C. (1983) Isolation of multigene families and determination of homologies by filter hybridization methods. In Wu, R., Grossman, L., Moldave, K. (eds.) Methods of Enzymology, Vol. 100 Academic Press, New York pp. 266-285.

Crickmore, N., Zeigler, D.R., Feitelson, J., Schnepf, E., Van Rie,J., Lereclus, D., Baum, J., and Dean, D. H. (1998), "Revision of the Nomenclature for the *Bacillus thuringiensis* Pesticidal Crystal Proteins," Microbiology and Molecular Biology Reviews 62: 807-813.

Huang, F., Rogers, L. B., Rhett, G. H. (2006) Comparative susceptibility of European corn borer, southwestern corn borer, and sugarcane borer (Lepidoptera: Crambidae) to Cry1Ab protein in a commercial *Bacillus thuringiensis* corn hybrid. J. Econ. Entomol. 99:194-202.

Meihls L N. Hiadon M L. Siegfried B P. Miller N J. Sappinaton T W. Ellersieck M R. Spencer T A. Hibbard B E. 2008. Increased survival of western corn rootworm on transgenic corn within three generations of on-plant greenhouse selection. Proc Natl Acad Sci USA. 105(49): 19177-82.

Meihls L N. Hiadon M L. Ellersieck M R. Tabashnik B E. Hibbard B E. 2012. Greenhouse-selected resistance to Cry3Bb1-producing corn in three western corn rootworm populations. PLoSOne. 2012; 7(12):e51055.

Oleson, J. D., Park, Y. L., Nowatzki, T. M., Tollefson, J. J. (2005). Node-injury scale to evaluate root injury by corn rootworms (Coleoptera: Chrysomelidae). J. Econ. Entomol. 98: 1-8.

Sambrook, J., Fritsch, E. F., Maniatis, T. (1989) *Molecular Cloning: A Laboratory Manual* (2nd ed., Cold Spring Harbor Laboratory Press, Plainview, N.Y.)

Tijssen, P. (1993) Laboratory Techniques in Biochemistry and Molecular Biology Hybridization with Nucleic Acid Probes, Part I, Chapter 2. P. C. van der Vliet (ed.), (Elsevier, N.Y.)

Wang, Kan. *Agrobacterium Protocols*. 2. 1. New Jersey: Humana Press, 2006. Print Weigel, D., Glazebrook, J. (eds.) (2002) *Arabidopsis*: A Laboratory Manual. Cold Spring Harbor Press, Cold Spring Harbor, N.Y., 354 pages.

The invention claimed is:

1. A method for controlling a coleopteran pest which comprises exposing the gut of said coleopteran pest to an effective combination of a potentiator protein and a toxin protein, wherein the potentiator protein comprises a functional amino acid sequence comprising a polypeptide having at least 95% sequence identity to SEQ ID NO:2.

2. The method of claim 1 wherein the toxin protein comprises any one of the toxin proteins selected from the group consisting of SEQ ID NOs: 4, 6, 8, 10, 12, 14, 16, 18, 20, 22, 24, 26, 71, 74, 76, 82, 86, 88, 91, 93, 95, 97, 99, 101, 103, and 105.

3. The method of claim 1 wherein the toxin protein is selected from the group consisting of SEQ ID NOs: 4, 6, 8, 10, 12, 14, 16, 18, 20, 22, 24, 26, 71, 74, 76, 82, 86, 88, 91, 93, 95, 97, 99, 101, 103, and 105.

4. The method of claim 1 wherein the coleopteran pest is western corn rootworm (WCR, *Diabrotica virgifera virgifera* LeConte).

5. The method of claim 2 wherein the coleopteran pest is western corn rootworm (WCR, *Diabrotica virgifera virgifera* LeConte).

6. The method of claim 3 wherein the coleopteran pest is western corn rootworm (WCR, *Diabrotica virgifera virgifera* LeConte).

* * * * *

SEQUENCE LISTING

```
<160> NUMBER OF SEQ ID NOS: 105

<210> SEQ ID NO 1
<211> LENGTH: 357
<212> TYPE: DNA
<213> ORGANISM: Bacillus thuringiensis
```

<400> SEQUENCE: 1

```
atggctaatt gtaatactga aaaagattat gatggttatt atgaattacc agaacctggt    60
gcaagattag gaagttgtgt tggattatat acaggattag acttatgtta tagcgttgat   120
gccgcgaatt tatctgttgc tatagatatt aaagtgtttg gtgtaagagt ggagcatggt   180
gaaattggta taggtaagcc attcactact actgttggtg taggaccagc aacagcaaag   240
attacaattt ctgtagttaa agaaggaaat aaacattgtt taaatattca gtataatgtt   300
cacttacctt tccttggaaa tgtagcacat ggaaataaag atgtagtttg tttttaa     357
```

<210> SEQ ID NO 2
<211> LENGTH: 118
<212> TYPE: PRT
<213> ORGANISM: Bacillus thuringiensis

<400> SEQUENCE: 2

```
Met Ala Asn Cys Asn Thr Glu Lys Asp Tyr Asp Gly Tyr Tyr Glu Leu
1               5                   10                  15
Pro Glu Pro Gly Ala Arg Leu Gly Ser Cys Val Gly Leu Tyr Thr Gly
            20                  25                  30
Leu Asp Leu Cys Tyr Ser Val Asp Ala Ala Asn Leu Ser Val Ala Ile
        35                  40                  45
Asp Ile Lys Val Phe Gly Val Arg Val Glu His Gly Glu Ile Gly Ile
    50                  55                  60
Gly Lys Pro Phe Thr Thr Thr Val Gly Val Gly Pro Ala Thr Ala Lys
65                  70                  75                  80
Ile Thr Ile Ser Val Val Lys Glu Gly Asn Lys His Cys Leu Asn Ile
                85                  90                  95
Gln Tyr Asn Val His Leu Pro Phe Leu Gly Asn Val Ala His Gly Asn
            100                 105                 110
Lys Asp Val Val Cys Phe
        115
```

<210> SEQ ID NO 3
<211> LENGTH: 555
<212> TYPE: DNA
<213> ORGANISM: Bacillus thuringiensis

<400> SEQUENCE: 3

```
atgaataatc atttattaga tttactttca aaagtccaaa ctaatttatt cgtcctaaaa    60
gaacacaaaa atattctttc agaatttcta gatttattaa atatagattc atcagataaa   120
tctttaattc aaaatcattt tcaaattttt agaaatactt tgttgaatat agaaaatcat   180
atggattccc taaaaaatga atatcagta ataaatccag ctgtttttgc aacagttagt   240
ggatctatta aaataaacaa atcaactat acatttgctg aagttaagta tagtgaaaat   300
gatgcaagtg aaaacctaa agaggaatt gaatttaaac ctggcggaaa tcgatatgta   360
atatctccta atccacattt gaataatcaa tacaacaata gtgacaacg acaattttat   420
agtgctttag cattaaatat tagctacaga ggtgatgatg aacattggga aaaaaataat   480
tggccaacaa aaactcaaga tcgtattact gcacttggcc aaaaatatac tttaacatat   540
gatggtaaag cttaa                                                   555
```

<210> SEQ ID NO 4
<211> LENGTH: 184
<212> TYPE: PRT
<213> ORGANISM: Bacillus thuringiensis

<400> SEQUENCE: 4

Met Asn Asn His Leu Leu Asp Leu Leu Ser Lys Val Gln Thr Asn Leu
1               5                   10                  15

Phe Val Leu Lys Glu His Lys Asn Ile Leu Ser Glu Phe Leu Asp Leu
                20                  25                  30

Leu Asn Ile Asp Ser Ser Asp Lys Ser Leu Ile Gln Asn His Phe Gln
            35                  40                  45

Ile Phe Arg Asn Thr Leu Leu Asn Ile Glu Asn His Met Asp Ser Leu
        50                  55                  60

Lys Asn Glu Ile Ser Val Ile Asn Pro Ala Val Phe Ala Thr Val Ser
65                  70                  75                  80

Gly Ser Ile Lys Ile Asn Lys Ile Asn Tyr Thr Phe Ala Glu Val Lys
                85                  90                  95

Tyr Ser Glu Asn Asp Ala Ser Gly Lys Pro Lys Arg Gly Ile Glu Phe
                100                 105                 110

Lys Pro Gly Gly Asn Arg Tyr Val Ile Ser Pro Asn Pro His Leu Asn
            115                 120                 125

Asn Gln Tyr Asn Asn Ser Gly Gln Arg Gln Phe Tyr Ser Ala Leu Ala
130                 135                 140

Leu Asn Ile Ser Tyr Arg Gly Asp Asp Glu His Trp Glu Lys Asn Asn
145                 150                 155                 160

Trp Pro Thr Lys Thr Gln Asp Arg Ile Thr Ala Leu Gly Gln Lys Tyr
                165                 170                 175

Thr Leu Thr Tyr Asp Gly Lys Ala
            180

<210> SEQ ID NO 5
<211> LENGTH: 555
<212> TYPE: DNA
<213> ORGANISM: Bacillus thuringiensis

<400> SEQUENCE: 5
atgaataacc agttattaga tttactgtca aaaactcaaa ctaatttatt tgttctaaaa      60
gaacagaaaa atacttttc tgaatttatc gattattaa aattagattc atcagatcga      120
tctttactcc aaaatatat ccatattttt gaaatagct tattcaatat tgaaaaccat      180
attgatactt taaaaatga attgtcctta ttggatccag ctattttgc aacagttagt      240
ggatctattc aaataaacaa ggttaaatat acatttgctg aagttcagta cagtggaaat      300
gatgaaagtg aaaacctaa agaggaatt gaattaaat ccggtggaaa tcgatatgta      360
atctctccta atccacattt aaataataga tataacaatg gtggacaacg agatttttat      420
aatgctttag cattaaaagt tagcgatata ggtgatgatg aaaaatggga aaaaaatgaa      480
tggccaacaa aaaatctaac acatcttagt gcgcttggtc aaaaatatga tttacattat      540
gatggcagag cttaa                                                      555

<210> SEQ ID NO 6
<211> LENGTH: 184
<212> TYPE: PRT
<213> ORGANISM: Bacillus thuringiensis

<400> SEQUENCE: 6

Met Asn Asn Gln Leu Leu Asp Leu Leu Ser Lys Thr Gln Thr Asn Leu
1               5                   10                  15

Phe Val Leu Lys Glu Gln Lys Asn Thr Phe Ser Glu Phe Ile Asp Leu

```
            20                  25                  30
Leu Lys Leu Asp Ser Ser Asp Arg Ser Leu Gln Lys Tyr Ile His
         35                  40                  45

Ile Phe Glu Asn Ser Leu Phe Asn Ile Glu Asn His Ile Asp Thr Leu
 50                  55                  60

Lys Asn Glu Leu Ser Leu Leu Asp Pro Ala Ile Phe Ala Thr Val Ser
 65                  70                  75                  80

Gly Ser Ile Gln Ile Asn Lys Val Lys Tyr Thr Phe Ala Glu Val Gln
             85                  90                  95

Tyr Ser Gly Asn Asp Glu Ser Gly Lys Pro Lys Arg Gly Ile Glu Phe
            100                 105                 110

Lys Ser Gly Gly Asn Arg Tyr Val Ile Ser Pro Asn Pro His Leu Asn
            115                 120                 125

Asn Arg Tyr Asn Asn Gly Gly Gln Arg Asp Phe Tyr Asn Ala Leu Ala
        130                 135                 140

Leu Lys Val Ser Asp Ile Gly Asp Asp Glu Lys Trp Glu Lys Asn Glu
145                 150                 155                 160

Trp Pro Thr Lys Asn Leu Thr His Leu Ser Ala Leu Gly Gln Lys Tyr
                165                 170                 175

Asp Leu His Tyr Asp Gly Arg Ala
            180

<210> SEQ ID NO 7
<211> LENGTH: 555
<212> TYPE: DNA
<213> ORGANISM: Bacillus thuringiensis

<400> SEQUENCE: 7
atggataatc atttttaga tttaatctca aaagttaaaa ctaatttatt tgttctaaaa      60
aaacaaaaaa atactctttc agaatttcta gatttattaa atgtagattt atcagatcaa     120 tcttaattc aaaatatct ccatattttt gaaaacagtc tattcaatat agaaaatcat      180
gttgatattc ttaaaaatga actatcaaca ttagatccag ctattttgat agcagttagt     240
ggatctatcc aataaataa tgtaaaatat acatttgctg aagttcagta cagtggaaat      300
gatgacagtg gaaaacctaa agaggaatc gaatttaaat caggaggaaa ccgatacgta      360
atatctccta atccacattt aaataatcga tataacggtg gtggacaacg agatttttat     420
aatgctttag cattaaaagt tagcgatatc ggtgatgatg aacattggga aaaaaacaac     480
tggccaacaa agaatttaac gcgtcttagt gcacttggtc aaaaatatga tttacattat     540
gatggtagag cttaa                                                      555

<210> SEQ ID NO 8
<211> LENGTH: 184
<212> TYPE: PRT
<213> ORGANISM: Bacillus thuringiensis

<400> SEQUENCE: 8

Met Asp Asn His Phe Leu Asp Leu Ile Ser Lys Val Lys Thr Asn Leu
 1               5                  10                  15

Phe Val Leu Lys Lys Gln Lys Asn Thr Leu Ser Glu Phe Leu Asp Leu
             20                  25                  30

Leu Asn Val Asp Leu Ser Asp Gln Ser Leu Ile Gln Lys Tyr Leu His
         35                  40                  45

Ile Phe Glu Asn Ser Leu Phe Asn Ile Glu Asn His Val Asp Ile Leu
 50                  55                  60
```

Lys Asn Glu Leu Ser Thr Leu Asp Pro Ala Ile Leu Ile Ala Val Ser
65                  70                  75                  80

Gly Ser Ile Pro Ile Asn Asn Val Lys Tyr Thr Phe Ala Glu Val Gln
                85                  90                  95

Tyr Ser Gly Asn Asp Asp Ser Gly Lys Pro Lys Arg Gly Ile Glu Phe
            100                 105                 110

Lys Ser Gly Gly Asn Arg Tyr Val Ile Ser Pro Asn Pro His Leu Asn
        115                 120                 125

Asn Arg Tyr Asn Gly Gly Gln Arg Asp Phe Tyr Asn Ala Leu Ala
    130                 135                 140

Leu Lys Val Ser Asp Ile Gly Asp Asp Glu His Trp Glu Lys Asn Asn
145                 150                 155                 160

Trp Pro Thr Lys Asn Leu Thr Arg Leu Ser Ala Leu Gly Gln Lys Tyr
                165                 170                 175

Asp Leu His Tyr Asp Gly Arg Ala
            180

<210> SEQ ID NO 9
<211> LENGTH: 624
<212> TYPE: DNA
<213> ORGANISM: Bacillus thuringiensis

<400> SEQUENCE: 9
atgtctttct tgaactgttt ccctttaaaa tatcttatgt tggatgctcc tcactctatt      60 ttgaaaagt ttagcttact ttcaaaaatt caaactaatt tatttgtttt aaaagaacaa     120
aaaaatactt tttcagaatt tctaaattta ttaaatatag attcatcaga ccaatctcta     180
attcaaaaat atcttcaagt ttttgaaaac agcctattta atatagagaa tcatgttgat     240
gttcttaaaa atgaaatatc agtattagat ccagatattt ttgcaacagt tagtgggtct     300
attacaataa ataatgtcaa atatacattt gctgaagttc aatacagtgg aaatgatgaa     360
agtggacgtc ctaaaagagg aattgaattt aaaccagggg gaaatcgata cgtaatatct     420
cctaatccac atttgaataa tcaatataac agcaatggac aacgacagtt ttatagtgct     480
ttagcatatg gtatacaaac caaatctata acgatggaa atactggaca ctcttgggag      540
aaaagcaatt ggccaacaat aaatcaagat cgtataaatg cacttggggt aagatatact     600
ttgaaatatg atggtagagc ttag                                           624

<210> SEQ ID NO 10
<211> LENGTH: 207
<212> TYPE: PRT
<213> ORGANISM: Bacillus thuringiensis

<400> SEQUENCE: 10

Met Ser Phe Leu Asn Cys Phe Pro Leu Lys Tyr Leu Met Leu Asp Ala
1               5                   10                  15

Pro His Ser Ile Leu Lys Lys Phe Ser Leu Leu Ser Lys Ile Gln Thr
            20                  25                  30

Asn Leu Phe Val Leu Lys Glu Gln Lys Asn Thr Phe Ser Glu Phe Leu
        35                  40                  45

Asn Leu Leu Asn Ile Asp Ser Ser Asp Gln Ser Leu Ile Gln Lys Tyr
    50                  55                  60

Leu Gln Val Phe Glu Asn Ser Leu Phe Asn Ile Glu Asn His Val Asp
65                  70                  75                  80

Val Leu Lys Asn Glu Ile Ser Val Leu Asp Pro Asp Ile Phe Ala Thr

```
                85                  90                  95
Val Ser Gly Ser Ile Thr Ile Asn Asn Val Lys Tyr Thr Phe Ala Glu
            100                 105                 110

Val Gln Tyr Ser Gly Asn Asp Glu Ser Gly Arg Pro Lys Arg Gly Ile
            115                 120                 125

Glu Phe Lys Pro Gly Gly Asn Arg Tyr Val Ile Ser Pro Asn Pro His
            130                 135                 140

Leu Asn Asn Gln Tyr Asn Ser Asn Gly Gln Arg Gln Phe Tyr Ser Ala
145                 150                 155                 160

Leu Ala Tyr Gly Ile Gln Thr Lys Ser Ile Asn Asp Gly Asn Thr Gly
                165                 170                 175

His Ser Trp Glu Lys Ser Asn Trp Pro Thr Ile Asn Gln Asp Arg Ile
                180                 185                 190

Asn Ala Leu Gly Val Arg Tyr Thr Leu Lys Tyr Asp Gly Arg Ala
                195                 200                 205

<210> SEQ ID NO 11
<211> LENGTH: 333
<212> TYPE: DNA
<213> ORGANISM: Bacillus thuringiensis

<400> SEQUENCE: 11
atggcaacag ttagcggaaa aataataata aatactatta aatatacatt cgcagaagtt      60
caatatagtg gaaatgatga agtggtagac cctaaaagag ggattgagtt taaaccagga     120
ggaaatcgat atattatttc tcctaatcca catttaaata taaatataa tacttcaaat     180 ggtccaatac aattttataa tgctttagca ttaaatctta gttataaagg agatgatgaa     240
cagtgggtaa aagggaattg gccaaaaaca atctaagtg gtcttaattc gcttggacaa     300
aaatatattt taaaatatga cagtagtaat taa                                  333

<210> SEQ ID NO 12
<211> LENGTH: 110
<212> TYPE: PRT
<213> ORGANISM: Bacillus thuringiensis

<400> SEQUENCE: 12

Met Ala Thr Val Ser Gly Lys Ile Ile Asn Thr Ile Lys Tyr Thr
1               5                  10                  15

Phe Ala Glu Val Gln Tyr Ser Gly Asn Asp Glu Ser Gly Arg Pro Lys
                20                  25                  30

Arg Gly Ile Glu Phe Lys Pro Gly Gly Asn Arg Tyr Ile Ile Ser Pro
            35                  40                  45

Asn Pro His Leu Asn Asn Lys Tyr Asn Thr Ser Asn Gly Pro Ile Gln
50                  55                  60

Phe Tyr Asn Ala Leu Ala Leu Asn Leu Ser Tyr Lys Gly Asp Asp Glu
65                  70                  75                  80

Gln Trp Val Lys Gly Asn Trp Pro Lys Thr Asn Leu Ser Gly Leu Asn
                85                  90                  95

Ser Leu Gly Gln Lys Tyr Ile Leu Lys Tyr Asp Ser Ser Asn
            100                 105                 110

<210> SEQ ID NO 13
<211> LENGTH: 564
<212> TYPE: DNA
<213> ORGANISM: Bacillus thuringiensis

<400> SEQUENCE: 13
```

```
atgaataata cattattgga attactttca aaaataaaaa aagaattctt tggtttgaat    60
catcaaaaaa gaacgttaga tgaatttatt aatctattag atatagatcc atctgatcgt   120
gaattattaa aacgccattt gtatcttttt gataatagta tagagcatat tatgaattat   180
atacattctc ttaaccaaga aatcttagta ttagatccca ctattttgc agcagtatct    240 ggaacgatta ttatcaataa taaaaattat acatttgtag aagtgcaata tagccaaagt   300
gatcaatatg gaccaaaaag aggaattaaa tttacaggtg gaggaaatga atatttaatt   360
gatcccaatc cacatgaaaa tggacaatat caaaaaaacg ccagacaatt ttatagtgct   420
ttagcatatg gtatacaagg gaagtctata acagatggac aaaatgggca tccttgggta   480
caaaataatt ggcccacagg caatcaagat cggattaatg cactaggaga agatataca    540 ttacaataca aggtagagc ttaa                                          564
```

<210> SEQ ID NO 14
<211> LENGTH: 187
<212> TYPE: PRT
<213> ORGANISM: Bacillus thuringiensis

<400> SEQUENCE: 14

```
Met Asn Asn Thr Leu Leu Glu Leu Leu Ser Lys Ile Lys Lys Glu Phe
1               5                   10                  15

Phe Gly Leu Asn His Gln Lys Arg Thr Leu Asp Glu Phe Ile Asn Leu
            20                  25                  30

Leu Asp Ile Asp Pro Ser Asp Arg Glu Leu Leu Lys Arg His Leu Tyr
        35                  40                  45

Leu Phe Asp Asn Ser Ile Glu His Ile Met Asn Tyr Ile His Ser Leu
    50                  55                  60

Asn Gln Glu Ile Leu Val Leu Asp Pro Thr Ile Phe Ala Ala Val Ser
65                  70                  75                  80

Gly Thr Ile Ile Ile Asn Asn Lys Asn Tyr Thr Phe Val Glu Val Gln
                85                  90                  95

Tyr Ser Gln Ser Asp Gln Tyr Gly Pro Lys Arg Gly Ile Lys Phe Thr
            100                 105                 110

Gly Gly Gly Asn Glu Tyr Leu Ile Asp Pro Asn Pro His Glu Asn Gly
        115                 120                 125

Gln Tyr Gln Lys Asn Ala Arg Gln Phe Tyr Ser Ala Leu Ala Tyr Gly
    130                 135                 140

Ile Gln Gly Lys Ser Ile Thr Asp Gly Gln Asn Gly His Pro Trp Val
145                 150                 155                 160

Gln Asn Asn Trp Pro Thr Gly Asn Gln Asp Arg Ile Asn Ala Leu Gly
                165                 170                 175

Glu Arg Tyr Thr Leu Gln Tyr Lys Gly Arg Ala
            180                 185
```

<210> SEQ ID NO 15
<211> LENGTH: 564
<212> TYPE: DNA
<213> ORGANISM: Bacillus thuringiensis

<400> SEQUENCE: 15

```
atgaataata cattattgga attactttca aaaataaaaa aagaattctt tggtttgaat    60
catcaaaaaa gaacattaga tgaatttatt aatctattag atatagaccc atctgatcgt   120
gaattattaa aacgccattt gtatcttttt gataatagta tagaacatat tatgaattat   180
```

```
atacattctc ttaaccaaga atcttagta ttagatccca ctattttgc agcagtatct     240 ggaacgatta ttatcaataa taaaaattat acatttgtag aagtgcaata tagccaaagt   300
gatcaatatg gaccaaaaag agggattaaa tttacaggtg gaggaaatga atatttaatt   360
gatcccaatc cacatgaaaa tggacaatat caaaaaaacg ccagacaatt ttatagtgct   420
ttagcatatg gtatacaagg gaagtctata acagatggac aaaatgggca tccttgggta   480
ccaaataatt ggcccacagg caatcaagat cggattaatg cactaggaga aagatataca   540
ttacaataca aaggtagagc ttaa                                          564
```

<210> SEQ ID NO 16
<211> LENGTH: 187
<212> TYPE: PRT
<213> ORGANISM: Bacillus thuringiensis

<400> SEQUENCE: 16

```
Met Asn Asn Thr Leu Leu Glu Leu Leu Ser Lys Ile Lys Lys Glu Phe
1               5                   10                  15

Phe Gly Leu Asn His Gln Lys Arg Thr Leu Asp Glu Phe Ile Asn Leu
                20                  25                  30

Leu Asp Ile Asp Pro Ser Asp Arg Glu Leu Leu Lys Arg His Leu Tyr
            35                  40                  45

Leu Phe Asp Asn Ser Ile Glu His Ile Met Asn Tyr Ile His Ser Leu
        50                  55                  60

Asn Gln Glu Ile Leu Val Leu Asp Pro Thr Ile Phe Ala Ala Val Ser
65                  70                  75                  80

Gly Thr Ile Ile Ile Asn Asn Lys Asn Tyr Thr Phe Val Glu Val Gln
                85                  90                  95

Tyr Ser Gln Ser Asp Gln Tyr Gly Pro Lys Arg Gly Ile Lys Phe Thr
                100                 105                 110

Gly Gly Gly Asn Glu Tyr Leu Ile Asp Pro Asn Pro His Glu Asn Gly
            115                 120                 125

Gln Tyr Gln Lys Asn Ala Arg Gln Phe Tyr Ser Ala Leu Ala Tyr Gly
        130                 135                 140

Ile Gln Gly Lys Ser Ile Thr Asp Gly Gln Asn Gly His Pro Trp Val
145                 150                 155                 160

Pro Asn Asn Trp Pro Thr Gly Asn Gln Asp Arg Ile Asn Ala Leu Gly
                165                 170                 175

Glu Arg Tyr Thr Leu Gln Tyr Lys Gly Arg Ala
                180                 185
```

<210> SEQ ID NO 17
<211> LENGTH: 564
<212> TYPE: DNA
<213> ORGANISM: Bacillus thuringiensis

<400> SEQUENCE: 17

```
atgaataaca cattattgga attactttca aaaataaaaa aagaattctt tggtttgaat    60
catcaaaaaa gaacgttaga tgaatttatt aatctattag atatagaccc atctgatcgt   120
gaattattaa aacgccattt gtatcttttt gataatagta tagaacatat tatgaattat   180
atacattctc ttaaccaaga atcttagta ttagatccca ctattttgc agcagtatct    240 ggaacgatta ttatcaataa taaaaattat acctttgtag aagtacaata tagccaaagt   300
gatcaatatg gaccaaaaag agggattaaa tttacaggtg gaggaaatga atatttaatt   360
gatcccaatc cacatgaaaa tggacaatat caaaaaaacg ctagacaatt ttatagtgct   420
```

```
ttagcatatg gtatacaagg gaagtctata acagatggac aaaatgggca tccttgggta    480
caaaataatt ggcccacagt caatcaagat cggattaatg cactaggaga agatataca    540 ttacaataca aaggtagggc ttaa                                          564
```

<210> SEQ ID NO 18
<211> LENGTH: 187
<212> TYPE: PRT
<213> ORGANISM: Bacillus thuringiensis

<400> SEQUENCE: 18

```
Met Asn Asn Thr Leu Leu Glu Leu Leu Ser Lys Ile Lys Lys Glu Phe
1               5                   10                  15

Phe Gly Leu Asn His Gln Lys Arg Thr Leu Asp Glu Phe Ile Asn Leu
            20                  25                  30

Leu Asp Ile Asp Pro Ser Asp Arg Glu Leu Leu Lys Arg His Leu Tyr
        35                  40                  45

Leu Phe Asp Asn Ser Ile Glu His Ile Met Asn Tyr Ile His Ser Leu
    50                  55                  60

Asn Gln Glu Ile Leu Val Leu Asp Pro Thr Ile Phe Ala Ala Val Ser
65                  70                  75                  80

Gly Thr Ile Ile Ile Asn Asn Lys Asn Tyr Thr Phe Val Glu Val Gln
                85                  90                  95

Tyr Ser Gln Ser Asp Gln Tyr Gly Pro Lys Arg Gly Ile Lys Phe Thr
            100                 105                 110

Gly Gly Gly Asn Glu Tyr Leu Ile Asp Pro Asn Pro His Glu Asn Gly
        115                 120                 125

Gln Tyr Gln Lys Asn Ala Arg Gln Phe Tyr Ser Ala Leu Ala Tyr Gly
    130                 135                 140

Ile Gln Gly Lys Ser Ile Thr Asp Gly Gln Asn Gly His Pro Trp Val
145                 150                 155                 160

Gln Asn Asn Trp Pro Thr Val Asn Gln Asp Arg Ile Asn Ala Leu Gly
                165                 170                 175

Glu Arg Tyr Thr Leu Gln Tyr Lys Gly Arg Ala
            180                 185
```

<210> SEQ ID NO 19
<211> LENGTH: 570
<212> TYPE: DNA
<213> ORGANISM: Bacillus thuringiensis

<400> SEQUENCE: 19

```
atgtatatga ataatacatt attggaatta ctttcaaaaa taaaaaaga attctttggt     60 ttgaatcatc aaaaagaac gttagatgaa tttattaatc tattagatat agatccatct    120
gatcgtgaat tattaaaacg ccatttgtat cttttggata atagtataga acatattatg    180
aattatatac attctcttaa ccaagaaatc ttagtattag atcccactat ttttgcagca    240
gtatctggaa cgattattat caataataaa aattatacat tgtagaagt gcaatatagc     300 caaagtgatc aatatggacc aaaaagaggg attaaattta caggtggagg aaatgaatat    360
ttaattgatc ccaatccaca tgaaaatgga caatatcaaa aaacgccag acaattttat    420 agtgctttag catatggtat acaagggaag tctataacag atggacaaaa tgggcatcct    480
tgggtacaaa ataattggcc cacaggcaat caagatcgga ttaatgcact aggagaaaga    540
tatacattac aatacaaagg tagagcttaa                                    570
```

<210> SEQ ID NO 20
<211> LENGTH: 189
<212> TYPE: PRT
<213> ORGANISM: Bacillus thuringiensis

<400> SEQUENCE: 20

```
Met Tyr Met Asn Asn Thr Leu Leu Glu Leu Leu Ser Lys Ile Lys Lys
1               5                   10                  15

Glu Phe Phe Gly Leu Asn His Gln Lys Arg Thr Leu Asp Glu Phe Ile
            20                  25                  30

Asn Leu Leu Asp Ile Asp Pro Ser Asp Arg Glu Leu Leu Lys Arg His
        35                  40                  45

Leu Tyr Leu Leu Asp Asn Ser Ile Glu His Ile Met Asn Tyr Ile His
    50                  55                  60

Ser Leu Asn Gln Glu Ile Leu Val Leu Asp Pro Thr Ile Phe Ala Ala
65                  70                  75                  80

Val Ser Gly Thr Ile Ile Ile Asn Asn Lys Asn Tyr Thr Phe Val Glu
                85                  90                  95

Val Gln Tyr Ser Gln Ser Asp Gln Tyr Gly Pro Lys Arg Gly Ile Lys
            100                 105                 110

Phe Thr Gly Gly Gly Asn Glu Tyr Leu Ile Asp Pro Asn Pro His Glu
        115                 120                 125

Asn Gly Gln Tyr Gln Lys Asn Ala Arg Gln Phe Tyr Ser Ala Leu Ala
    130                 135                 140

Tyr Gly Ile Gln Gly Lys Ser Ile Thr Asp Gly Gln Asn Gly His Pro
145                 150                 155                 160

Trp Val Gln Asn Asn Trp Pro Thr Gly Asn Gln Asp Arg Ile Asn Ala
                165                 170                 175

Leu Gly Glu Arg Tyr Thr Leu Gln Tyr Lys Gly Arg Ala
            180                 185
```

<210> SEQ ID NO 21
<211> LENGTH: 570
<212> TYPE: DNA
<213> ORGANISM: Bacillus thuringiensis

<400> SEQUENCE: 21

```
atgtatatga ataatacatt attggaatta ctttcaaaaa taaaaaaga  attctttggt    60
ttgaatcatc aaaaaagaac gttagatgaa tttattaatc tattagatat agatccatct   120
gatcgtgaat tattaaaacg ccatttgtat cttttggata atagtataga acatattatg   180
aattatatac attctcttaa ccaagaaatc ttagtattag atcccactat ttttgcagca   240
gtatctggaa cgattattat caataataaa aattatacat tgtagaagt  gcaatatagc   300
caaagtgatc catatggact gaaaagaggg attaaattta caggtggagg aaatgaatat   360
gtaattgcgc ctaatccaga tgaaaatgga aaatacaaaa aaatacgag  acaattttat   420
aatgatttag catatggtat acaagggaag tctataacag atggacaaaa tgggcatcct   480
tgggtacaaa ataattggcc tacaggcaat caagatcgga ttaatgcact aggagaaaga   540
tatacattac aatacaaagg tagagcttaa                                    570
```

<210> SEQ ID NO 22
<211> LENGTH: 189
<212> TYPE: PRT
<213> ORGANISM: Bacillus thuringiensis

<400> SEQUENCE: 22

Met Tyr Met Asn Asn Thr Leu Leu Glu Leu Leu Ser Lys Ile Lys Lys
1               5                   10                  15

Glu Phe Phe Gly Leu Asn His Gln Lys Arg Thr Leu Asp Glu Phe Ile
            20                  25                  30

Asn Leu Leu Asp Ile Asp Pro Ser Asp Arg Glu Leu Leu Lys Arg His
            35                  40                  45

Leu Tyr Leu Leu Asp Asn Ser Ile Glu His Ile Met Asn Tyr Ile His
    50                  55                  60

Ser Leu Asn Gln Glu Ile Leu Val Leu Asp Pro Thr Ile Phe Ala Ala
65              70                  75                  80

Val Ser Gly Thr Ile Ile Asn Asn Lys Asn Tyr Thr Phe Val Glu
                85                  90                  95

Val Gln Tyr Ser Gln Ser Asp Pro Tyr Gly Leu Lys Arg Gly Ile Lys
            100                 105                 110

Phe Thr Gly Gly Gly Asn Glu Tyr Val Ile Ala Pro Asn Pro Asp Glu
            115                 120                 125

Asn Gly Lys Tyr Lys Lys Asn Thr Arg Gln Phe Tyr Asn Asp Leu Ala
            130                 135                 140

Tyr Gly Ile Gln Gly Lys Ser Ile Thr Asp Gly Gln Asn Gly His Pro
145                 150                 155                 160

Trp Val Gln Asn Asn Trp Pro Thr Gly Asn Gln Asp Arg Ile Asn Ala
                165                 170                 175

Leu Gly Glu Arg Tyr Thr Leu Gln Tyr Lys Gly Arg Ala
            180                 185

<210> SEQ ID NO 23
<211> LENGTH: 579
<212> TYPE: DNA
<213> ORGANISM: Bacillus thuringiensis

<400> SEQUENCE: 23
atggataatc atttattagg gttactttca aaaatccaaa acaatgtttt tgttctaaaa      60
gaacaaaaac gcagtgtttc agaattttta aatctattag atatagattc atctaatcaa     120 ttttaattc aacaatattt tcaaatgttt gaacacagct tatttaatat cgagaattat      180
gttgattctc ttacagatga aatatcaata ttaaaccctt ctagtttcat agcagttagt     240
ggaaatatat atgtaggtag acaacaagat aggtactcat tgtagaaat tcagtatact     300 cagaatgata gttcgggaag acctaaaaga ggaatcacat ttacatcagg agcaattaag    360
tatgatatat cccctaatcc tcatttaagt aaagcatata ataataacgg acaacgagat    420
ttttataata gcttagcatt aaaagttcgt gattacgcca cagatcataa ttgggttaga    480
ggtggttggg attattctca gaattaact tttaatttaa gtggatttag tggtagtgaa     540
ggtagtagat acaccttgac acctgtagct aaaacttaa                           579

<210> SEQ ID NO 24
<211> LENGTH: 192
<212> TYPE: PRT
<213> ORGANISM: Bacillus thuringiensis

<400> SEQUENCE: 24

Met Asp Asn His Leu Leu Gly Leu Leu Ser Lys Ile Gln Asn Asn Val
1               5                   10                  15

Phe Val Leu Lys Glu Gln Lys Arg Ser Val Ser Glu Phe Leu Asn Leu
            20                  25                  30

Leu Asp Ile Asp Ser Ser Asn Gln Phe Leu Ile Gln Gln Tyr Phe Gln
            35                  40                  45

Met Phe Glu His Ser Leu Phe Asn Ile Glu Asn Tyr Val Asp Ser Leu
 50                  55                  60

Thr Asp Glu Ile Ser Ile Leu Asn Pro Ser Ser Phe Ile Ala Val Ser
 65                  70                  75                  80

Gly Asn Ile Tyr Val Gly Arg Gln Gln Asp Arg Tyr Ser Phe Val Glu
                 85                  90                  95

Ile Gln Tyr Thr Gln Asn Asp Ser Ser Gly Arg Pro Lys Arg Gly Ile
            100                 105                 110

Thr Phe Thr Ser Gly Ala Ile Lys Tyr Asp Ile Ser Pro Asn Pro His
            115                 120                 125

Leu Ser Lys Ala Tyr Asn Asn Asn Gly Gln Arg Asp Phe Tyr Asn Ser
130                 135                 140

Leu Ala Leu Lys Val Arg Asp Tyr Ala Thr Asp His Asn Trp Val Arg
145                 150                 155                 160

Gly Gly Trp Asp Tyr Ser Gln Lys Leu Thr Phe Asn Leu Ser Gly Phe
                165                 170                 175

Ser Gly Ser Glu Gly Ser Arg Tyr Thr Leu Thr Pro Val Ala Lys Thr
            180                 185                 190

<210> SEQ ID NO 25
<211> LENGTH: 366
<212> TYPE: DNA
<213> ORGANISM: Bacillus thuringiensis

<400> SEQUENCE: 25
atgaaaaaag gatttcttgc cgtatcattg tccctgtttt tggccattgc tttaatcgtg      60
tttcctttct ccggcactaa tgtagatgct aaagggtaa gtggctcaat cacgatcaac     120
aaagaaacat ataaatatat cgaagaatct ttcggaaaaa atcgagggat tacattcaac     180
ccaggtcaac atacgtacaa aataactccg aatcctcacg acaatcccaa atacaacaaa     240
aaacaagagc agttctatga ggaaatcgca aaaggcgtta aaactcttgt agaaaaatca     300
ggctggaaag atactctcag caacattaca gctctgggtg aaacctatac attagctcca     360
cgttaa                                                                 366

<210> SEQ ID NO 26
<211> LENGTH: 121
<212> TYPE: PRT
<213> ORGANISM: Bacillus thuringiensis

<400> SEQUENCE: 26

Met Lys Lys Gly Phe Leu Ala Val Ser Leu Ser Leu Phe Leu Ala Ile
 1               5                  10                  15

Ala Leu Ile Val Phe Pro Phe Ser Gly Thr Asn Val Asp Ala Lys Gly
            20                  25                  30

Val Ser Gly Ser Ile Thr Ile Asn Lys Glu Thr Lys Tyr Ile Glu
            35                  40                  45

Glu Ser Phe Gly Lys Asn Arg Gly Ile Thr Phe Asn Pro Gly Gln His
 50                  55                  60

Thr Tyr Lys Ile Thr Pro Asn Pro His Asp Asn Pro Lys Tyr Asn Lys
 65                  70                  75                  80

Lys Gln Glu Gln Phe Tyr Glu Glu Ile Ala Lys Gly Val Lys Thr Leu
                 85                  90                  95

Val Glu Lys Ser Gly Trp Lys Asp Thr Leu Ser Asn Ile Thr Ala Leu

```
            100                 105                 110
Gly Glu Thr Tyr Thr Leu Ala Pro Arg
        115                 120
```

<210> SEQ ID NO 27
<211> LENGTH: 32
<212> TYPE: DNA
<213> ORGANISM: Artificial Sequence
<220> FEATURE:
<223> OTHER INFORMATION: synthesized primer oligonucleotide

<400> SEQUENCE: 27
ggatccgtcg tagtaccagt atgaccaagt tg                                   32

<210> SEQ ID NO 28
<211> LENGTH: 43
<212> TYPE: DNA
<213> ORGANISM: Artificial Sequence
<220> FEATURE:
<223> OTHER INFORMATION: synthesized primer oligonucleotide

<400> SEQUENCE: 28
ccgcggggta ccccaaaata atatctttct tgaattgttt ctc                       43

<210> SEQ ID NO 29
<211> LENGTH: 41
<212> TYPE: DNA
<213> ORGANISM: Artificial Sequence
<220> FEATURE:
<223> OTHER INFORMATION: synthesized primer oligonucleotide

<400> SEQUENCE: 29
ggatccagga gtaaaaacac atatgaataa tcatttatta g                         41

<210> SEQ ID NO 30
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 30
ggtaccttat taagctttac catcatatgt taaagtatat ttttggcc                  48

<210> SEQ ID NO 31
<211> LENGTH: 41
<212> TYPE: DNA
<213> ORGANISM: Artificial Sequence
<220> FEATURE:
<223> OTHER INFORMATION: synthesized primer oligonucleotide

<400> SEQUENCE: 31
actagtagga gtaaaaacac atatgaataa tcatttatta g                         41

<210> SEQ ID NO 32
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 32
ctcgagttat taagctttac catcatatgt taaagtatat ttttggcc                  48

<210> SEQ ID NO 33

-continued

```
<211> LENGTH: 32
<212> TYPE: DNA
<213> ORGANISM: Artificial Sequence
<220> FEATURE:
<223> OTHER INFORMATION: synthesized primer oligonucleotide

<400> SEQUENCE: 33
ccgcgggtcg tagtaccagt atgaccaagt tg                                32

<210> SEQ ID NO 34
<211> LENGTH: 37
<212> TYPE: DNA
<213> ORGANISM: Artificial Sequence
<220> FEATURE:
<223> OTHER INFORMATION: synthesized primer oligonucleotide

<400> SEQUENCE: 34
ggtaccccaa aataatatct ttcttgaatt gtttctc                           37

<210> SEQ ID NO 35
<211> LENGTH: 28
<212> TYPE: DNA
<213> ORGANISM: Artificial Sequence
<220> FEATURE:
<223> OTHER INFORMATION: synthesized primer oligonucleotide

<400> SEQUENCE: 35
ggatccagca ccagaaccct ccaaatac                                     28

<210> SEQ ID NO 36
<211> LENGTH: 39
<212> TYPE: DNA
<213> ORGANISM: Artificial Sequence
<220> FEATURE:
<223> OTHER INFORMATION: synthesized primer oligonucleotide

<400> SEQUENCE: 36
ccgcggccgt cttttctgga gatagtttga gttactatc                         39

<210> SEQ ID NO 37
<211> LENGTH: 28
<212> TYPE: DNA
<213> ORGANISM: Artificial Sequence
<220> FEATURE:
<223> OTHER INFORMATION: synthesized primer oligonucleotide

<400> SEQUENCE: 37
ccgcggagca ccagaaccct ccaaatac                                     28

<210> SEQ ID NO 38
<211> LENGTH: 39
<212> TYPE: DNA
<213> ORGANISM: Artificial Sequence
<220> FEATURE:
<223> OTHER INFORMATION: synthesized primer oligonucleotide

<400> SEQUENCE: 38
ggtaccccgt cttttctgga gatagtttga gttactatc                         39

<210> SEQ ID NO 39
<211> LENGTH: 47
<212> TYPE: DNA
<213> ORGANISM: Artificial Sequence
<220> FEATURE:
<223> OTHER INFORMATION: synthesized primer oligonucleotide

<400> SEQUENCE: 39
```

```
gtgtactagt atgaataacc agtttattaga tttactgtca aaaactc        47
```

<210> SEQ ID NO 40
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 40

```
tctcctcgag ttaagctctg ccatcataat gtaaatcata tttttgac        48
```

<210> SEQ ID NO 41
<211> LENGTH: 44
<212> TYPE: DNA
<213> ORGANISM: Artificial Sequence
<220> FEATURE:
<223> OTHER INFORMATION: synthesized primer oligonucleotide

<400> SEQUENCE: 41

```
gtgtactagt atggataatc attttttaga tttaatctca aaag             44
```

<210> SEQ ID NO 42
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 42

```
tctcctcgag ttaagctcta ccatcataat gtaaatcata tttttgac        48
```

<210> SEQ ID NO 43
<211> LENGTH: 44
<212> TYPE: DNA
<213> ORGANISM: Artificial Sequence
<220> FEATURE:
<223> OTHER INFORMATION: synthesized primer oligonucleotide

<400> SEQUENCE: 43

```
gtgtactagt atgtctttct tgaactgttt ccctttaaaa tatc             44
```

<210> SEQ ID NO 44
<211> LENGTH: 46
<212> TYPE: DNA
<213> ORGANISM: Artificial Sequence
<220> FEATURE:
<223> OTHER INFORMATION: synthesized primer oligonucleotide

<400> SEQUENCE: 44

```
tctcctcgag ctaagctcta ccatcatatt tcaaagtata tcttac          46
```

<210> SEQ ID NO 45
<211> LENGTH: 45
<212> TYPE: DNA
<213> ORGANISM: Artificial Sequence
<220> FEATURE:
<223> OTHER INFORMATION: synthesized primer oligonucleotide

<400> SEQUENCE: 45

```
gtgtactagt atggcaacag ttagcggaaa ataataata aatac            45
```

<210> SEQ ID NO 46
<211> LENGTH: 53
<212> TYPE: DNA

```
<213> ORGANISM: Artificial Sequence
<220> FEATURE:
<223> OTHER INFORMATION: synthesized primer oligonucleotide

<400> SEQUENCE: 46
tctcctcgag ttaattacta ctgtcatatt ttaaaatata ttttgtcca agc            53

<210> SEQ ID NO 47
<211> LENGTH: 63
<212> TYPE: DNA
<213> ORGANISM: Artificial Sequence
<220> FEATURE:
<223> OTHER INFORMATION: synthesized primer oligonucleotide

<400> SEQUENCE: 47
gtgtactagt atgaataata cattattgga attactttca aaaataaaaa aagaattctt   60
tgg                                                                 63

<210> SEQ ID NO 48
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 48
tctcctcgag ttaagctcta cctttgtatt gtaatgtata tctttctc                48

<210> SEQ ID NO 49
<211> LENGTH: 63
<212> TYPE: DNA
<213> ORGANISM: Artificial Sequence
<220> FEATURE:
<223> OTHER INFORMATION: synthesized primer oligonucleotide

<400> SEQUENCE: 49
gtgtactagt atgaataata cattattgga attactttca aaaataaaaa aagaattctt   60
tgg                                                                 63

<210> SEQ ID NO 50
<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 50
tctcctcgag ttaagctcta cctttgtatt gtaatgtata tctttctcc               49

<210> SEQ ID NO 51
<211> LENGTH: 63
<212> TYPE: DNA
<213> ORGANISM: Artificial Sequence
<220> FEATURE:
<223> OTHER INFORMATION: synthesized primer oligonucleotide

<400> SEQUENCE: 51
gtgtactagt atgaataaca cattattgga attactttca aaaataaaaa aagaattctt   60
tgg                                                                 63

<210> SEQ ID NO 52
<211> LENGTH: 49
<212> TYPE: DNA
<213> ORGANISM: Artificial Sequence
```

```
<220> FEATURE:
<223> OTHER INFORMATION: synthesized primer oligonucleotide

<400> SEQUENCE: 52
tctcctcgag ttaagcccta cctttgtatt gtaatgtata tctttctcc                49

<210> SEQ ID NO 53
<211> LENGTH: 69
<212> TYPE: DNA
<213> ORGANISM: Artificial Sequence
<220> FEATURE:
<223> OTHER INFORMATION: synthesized primer oligonucleotide

<400> SEQUENCE: 53
gtgtactagt atgtatatga ataatacatt attggaatta ctttcaaaaa taaaaaaga    60 attctttgg                                                            69

<210> SEQ ID NO 54
<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 54
tctcctcgag ttaagctcta cctttgtatt gtaatgtata tctttctcc                49

<210> SEQ ID NO 55
<211> LENGTH: 59
<212> TYPE: DNA
<213> ORGANISM: Artificial Sequence
<220> FEATURE:
<223> OTHER INFORMATION: synthesized primer oligonucleotide

<400> SEQUENCE: 55
gtgtactagt atgtatatga ataatacatt attggaatta ctttcaaaaa taaaaaag      59

<210> SEQ ID NO 56
<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 56
tctcctcgag ttaagctcta cctttgtatt gtaatgtata tctttctcc                49

<210> SEQ ID NO 57
<211> LENGTH: 47
<212> TYPE: DNA
<213> ORGANISM: Artificial Sequence
<220> FEATURE:
<223> OTHER INFORMATION: synthesized primer oligonucleotide

<400> SEQUENCE: 57
gtgtactagt atggataatc atttattagg gttactttca aaaatcc                  47

<210> SEQ ID NO 58
<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 58
```
tctcctcgag ttaagttta gctacaggtg tcaaggtgta tctactacc      49

<210> SEQ ID NO 59
<211> LENGTH: 40
<212> TYPE: DNA
<213> ORGANISM: Artificial Sequence
<220> FEATURE:
<223> OTHER INFORMATION: synthesized primer oligonucleotide

<400> SEQUENCE: 59
gtgtactagt atgaaaaaag gatttcttgc cgtatcattg      40

<210> SEQ ID NO 60
<211> LENGTH: 39
<212> TYPE: DNA
<213> ORGANISM: Artificial Sequence
<220> FEATURE:
<223> OTHER INFORMATION: synthesized primer oligonucleotide

<400> SEQUENCE: 60
tctcctcgag ttaacgtgga gctaatgtat aggtttcac      39

<210> SEQ ID NO 61
<211> LENGTH: 357
<212> TYPE: DNA
<213> ORGANISM: Artificial Sequence
<220> FEATURE:
<223> OTHER INFORMATION: Maize optimized

<400> SEQUENCE: 61
atggctaact gcaacaccga aaggactac gacggctact acgagctgcc ggagcctggt      60
gcgaggctgg ggagctgcgt gggcctgtac accggactgg acctgtgcta cagcgtggac     120
gcagccaacc tgagcgtggc catcgacatt aaagtgttcg gcgtgagggt ggagcacggc     180
gagatcggca tcggcaagcc gttcaccacc accgtgggcg tgggaccagc caccgcgaag     240
atcacgatct cagtggtgaa ggagggcaat aaacactgcc tgaatatcca gtacaacgtc     300
cacctgccgt tcctgggcaa cgtggctcac ggcaataaag acgtggtgtg cttctga       357

<210> SEQ ID NO 62
<211> LENGTH: 357
<212> TYPE: DNA
<213> ORGANISM: Artificial Sequence
<220> FEATURE:
<223> OTHER INFORMATION: Maize optimized

<400> SEQUENCE: 62
atggctaact gcaacaccga aaggactac gacggctact acgagctgcc ggagcctggt      60
gcgaggctgg ggagctgcgt gggcctgtac accggactgg acctgtgcta cagcgtggac     120
gcagccaacc tgagcgtggc catcgacatc aaggtgttcg gcgtgagggt ggagcacggc     180
gagatcggca tcggcaagcc gttcaccacc accgtgggcg tgggaccagc caccgcgaag     240
atcacgatct cagtggtgaa ggagggcaac aagcactgcc tgaatatcca gtacaacgtc     300
cacctgccgt tcctgggcaa cgtggctcac ggcaacaagg acgtggtgtg cttctga       357

<210> SEQ ID NO 63
<211> LENGTH: 118
<212> TYPE: PRT
<213> ORGANISM: Artificial Sequence
<220> FEATURE:
<223> OTHER INFORMATION: translated from synthesized maize optimized
      coding region

<400> SEQUENCE: 63

Met Ala Asn Cys Asn Thr Glu Lys Asp Tyr Asp Gly Tyr Tyr Glu Leu
1               5                   10                  15

Pro Glu Pro Gly Ala Arg Leu Gly Ser Cys Val Gly Leu Tyr Thr Gly
            20                  25                  30

Leu Asp Leu Cys Tyr Ser Val Asp Ala Ala Asn Leu Ser Val Ala Ile
        35                  40                  45

Asp Ile Lys Val Phe Gly Val Arg Val Glu His Gly Glu Ile Gly Ile
    50                  55                  60

Gly Lys Pro Phe Thr Thr Thr Val Gly Val Gly Pro Ala Thr Ala Lys
65              70                  75                  80

Ile Thr Ile Ser Val Val Lys Glu Gly Asn Lys His Cys Leu Asn Ile
                85                  90                  95

Gln Tyr Asn Val His Leu Pro Phe Leu Gly Asn Val Ala His Gly Asn
            100                 105                 110

Lys Asp Val Val Cys Phe
            115

<210> SEQ ID NO 64
<211> LENGTH: 570
<212> TYPE: DNA
<213> ORGANISM: Artificial Sequence
<220> FEATURE:
<223> OTHER INFORMATION: Maize optimized

<400> SEQUENCE: 64
atgttggctc gccaaggagg atcactgaga gcctctcagt gtaacgctgg cctcgcgaga      60
cgcgtggagg tgggagcgtt ggttgttccg agacccataa gcgtcaacga cgtggttccc     120
catgtctatt cggctcctct gagcgtcgcg aggaggtcgt gctccaagtc atccatccgc     180
tcgactcgca gacttcagac aaccgtctgc tccatggcta actgcaacac cgagaaggac     240
tacgacggct actacgagct gccggagcct ggtgcgaggc tggggagctg cgtgggcctg     300
tacaccggac tggacctgtg ctacagcgtg gacgcagcca acctgagcgt ggccatcgac     360
atcaaggtgt tcggcgtgag ggtggagcac ggcgagatcg gcatcggcaa gccgttcacc     420
accaccgtgg gcgtgggacc agccaccgcg aagatcacga tctcagtggt gaaggagggc     480
aacaagcact gcctgaatat ccagtacaac gtccacctgc cgttcctggg caacgtggct     540
cacggcaaca aggacgtggt gtgcttctga                                      570

<210> SEQ ID NO 65
<211> LENGTH: 570
<212> TYPE: DNA
<213> ORGANISM: Artificial Sequence
<220> FEATURE:
<223> OTHER INFORMATION: Maize optimized

<400> SEQUENCE: 65
atgttggctc gccaaggagg atcactgaga gcctctcagt gtaacgctgg cctcgcgaga      60
cgcgtggagg tgggagcgtt ggttgttccg agacccataa gcgtcaacga cgtggttccc     120
catgtctatt cggctcctct gagcgtcgcg aggaggtcgt gctccaagtc atccatccgc     180
tcgactcgca gacttcagac aaccgtctgc tccatggcta actgcaacac cgagaaggac     240
tacgacggct actacgagct gccggagcct ggtgcgaggc tggggagctg cgtgggcctg     300
tacaccggac tggacctgtg ctacagcgtg gacgcagcca acctgagcgt ggccatcgac     360
attaaagtgt tcggcgtgag ggtggagcac ggcgagatcg gcatcggcaa gccgttcacc     420

```
accaccgtgg gcgtgggacc agccaccgcg aagatcacga tctcagtggt gaaggagggc      480
aataaacact gcctgaatat ccagtacaac gtccacctgc cgttcctggg caacgtggct      540
cacggcaata agacgtggt gtgcttctga                                         570
```

```
<210> SEQ ID NO 66
<211> LENGTH: 189
<212> TYPE: PRT
<213> ORGANISM: Artificial Sequence
<220> FEATURE:
<223> OTHER INFORMATION: translated from synthesized maize optimized
      coding region

<400> SEQUENCE: 66
```

Met Leu Ala Arg Gln Gly Gly Ser Leu Arg Ala Ser Gln Cys Asn Ala
1               5                   10                  15

Gly Leu Ala Arg Arg Val Glu Val Gly Ala Leu Val Val Pro Arg Pro
            20                  25                  30

Ile Ser Val Asn Asp Val Val Pro His Val Tyr Ser Ala Pro Leu Ser
        35                  40                  45

Val Ala Arg Arg Ser Cys Ser Lys Ser Ser Ile Arg Ser Thr Arg Arg
    50                  55                  60

Leu Gln Thr Thr Val Cys Ser Met Ala Asn Cys Asn Thr Glu Lys Asp
65                  70                  75                  80

Tyr Asp Gly Tyr Tyr Glu Leu Pro Glu Pro Gly Ala Arg Leu Gly Ser
                85                  90                  95

Cys Val Gly Leu Tyr Thr Gly Leu Asp Leu Cys Tyr Ser Val Asp Ala
            100                 105                 110

Ala Asn Leu Ser Val Ala Ile Asp Ile Lys Val Phe Gly Val Arg Val
        115                 120                 125

Glu His Gly Glu Ile Gly Ile Gly Lys Pro Phe Thr Thr Thr Val Gly
    130                 135                 140

Val Gly Pro Ala Thr Ala Lys Ile Thr Ile Ser Val Val Lys Glu Gly
145                 150                 155                 160

Asn Lys His Cys Leu Asn Ile Gln Tyr Asn Val His Leu Pro Phe Leu
                165                 170                 175

Gly Asn Val Ala His Gly Asn Lys Asp Val Val Cys Phe
            180                 185

```
<210> SEQ ID NO 67
<211> LENGTH: 555
<212> TYPE: DNA
<213> ORGANISM: Artificial Sequence
<220> FEATURE:
<223> OTHER INFORMATION: Maize optimized

<400> SEQUENCE: 67
```

```
atggctcaat ctagcagaat ctgccacggt gtgcagaacc catgtgtgat catttccaat      60
ctctccaaat ccaaccagaa caaatctcct ttctcagtca gcctcaagac tcaccagcag     120
cagcgtcgtg cttaccagat atctagctgg ggattgaaga agtcaaacaa cgggtccgtg     180
attcgtccgg ttaaggcaat ggctaactgc aacaccgaga aggactacga cggctactac     240
gagctgccgg agcctggtgc gaggctgggg agctgcgtgg gcctgtacac cggactggac     300
ctgtgctaca gcgtggacgc agccaacctg agcgtggcca tcgacattaa agtgttcggc     360
gtgagggtgg agcacggcga gatcggcatc ggcaagccgt tcaccaccac cgtgggcgtg     420
ggaccagcca ccgcgaagat cacgatctca gtggtgaagg agggcaataa acactgcctg     480
```

```
aatatccagt acaacgtcca cctgccgttc ctgggcaacg tggctcacgg caataaagac    540
gtggtgtgct tctga                                                     555

<210> SEQ ID NO 68
<211> LENGTH: 184
<212> TYPE: PRT
<213> ORGANISM: Artificial Sequence
<220> FEATURE:
<223> OTHER INFORMATION: translated from synthesized maize optimized
      coding region

<400> SEQUENCE: 68

Met Ala Gln Ser Ser Arg Ile Cys His Gly Val Gln Asn Pro Cys Val
1               5                   10                  15

Ile Ile Ser Asn Leu Ser Lys Ser Asn Gln Asn Lys Ser Pro Phe Ser
            20                  25                  30

Val Ser Leu Lys Thr His Gln Gln Gln Arg Arg Ala Tyr Gln Ile Ser
        35                  40                  45

Ser Trp Gly Leu Lys Lys Ser Asn Asn Gly Ser Val Ile Arg Pro Val
    50                  55                  60

Lys Ala Met Ala Asn Cys Asn Thr Glu Lys Asp Tyr Asp Gly Tyr Tyr
65                  70                  75                  80

Glu Leu Pro Glu Pro Gly Ala Arg Leu Gly Ser Cys Val Gly Leu Tyr
                85                  90                  95

Thr Gly Leu Asp Leu Cys Tyr Ser Val Asp Ala Ala Asn Leu Ser Val
            100                 105                 110

Ala Ile Asp Ile Lys Val Phe Gly Val Arg Val Glu His Gly Glu Ile
        115                 120                 125

Gly Ile Gly Lys Pro Phe Thr Thr Thr Val Gly Val Gly Pro Ala Thr
    130                 135                 140

Ala Lys Ile Thr Ile Ser Val Val Lys Glu Gly Asn Lys His Cys Leu
145                 150                 155                 160

Asn Ile Gln Tyr Asn Val His Leu Pro Phe Leu Gly Asn Val Ala His
                165                 170                 175

Gly Asn Lys Asp Val Val Cys Phe
            180

<210> SEQ ID NO 69
<211> LENGTH: 555
<212> TYPE: DNA
<213> ORGANISM: Artificial Sequence
<220> FEATURE:
<223> OTHER INFORMATION: Maize optimized

<400> SEQUENCE: 69
atgaataatc acctgcttga cctgctgtcc aaggtgcaga ccaacctgtt cgtgctgaag     60
gagcacaaaa atatcctgag cgagttcctg gacctattaa atatcgactc ctccgacaag    120
agcctgatcc agaaccactt tcagatattc cggaacaccc tgctgaacat cgagaaccac    180
atggactccc tgaagaatga aatttccgta ataaacccag cggtgttcgc gaccgtgagc    240
ggcagcatta aaataaacaa aatcaactat acattcgccg aggtgaagta cagcgagaac    300
gacgcctccg gcaagcctaa gaggggcatc gagttcaaac cgggtggcaa cagatacgtg    360
atcagcccga acccgcacct gaataatcaa tacaacaact ccggacagag gcagttctac    420
tccgcactgg cattaaacat ctcatacaga ggcgacgacg agcactggga gaaaaataat    480
tggccgacca gacccaagat aggatcacc gcgctgggcc aaaaatatac cctgacctac    540
```

```
gacggcaagg cctga                                              555
```

<210> SEQ ID NO 70
<211> LENGTH: 555
<212> TYPE: DNA
<213> ORGANISM: Artificial Sequence
<220> FEATURE:
<223> OTHER INFORMATION: Maize optimized

<400> SEQUENCE: 70

```
atgaacaacc acctgcttga cctgctgtcc aaggtgcaga ccaacctgtt cgtgctgaag    60
gagcacaaga acatcctgag cgagttcctg gacctgctga atatcgactc ctccgacaag   120
agcctgatcc agaaccactt tcagatattc cggaacaccc tgctgaacat cgagaaccac   180
atggactccc tgaagaacga gatttccgtg atcaacccag cggtgttcgc gaccgtgagc   240
ggcagcatca agatcaacaa gatcaactac accttcgccg aggtgaagta cagcgagaac   300
gacgcctccg gcaagcctaa gaggggcatc gagttcaaac cgggtggcaa cagatacgtg   360
atcagcccga acccgcacct gaacaaccag tacaacaact ccggacagag gcagttctac   420
tccgcactgg cgctgaacat ctcatacaga ggcgacgacg agcactggga gaagaacaac   480
tggccgacca agacccaaga taggatcacc gcgctgggcc agaagtacac cctgacctac   540
gacggcaagg cctga                                                   555
```

<210> SEQ ID NO 71
<211> LENGTH: 184
<212> TYPE: PRT
<213> ORGANISM: Artificial Sequence
<220> FEATURE:
<223> OTHER INFORMATION: translated from synthesized maize optimized
       coding region

<400> SEQUENCE: 71

```
Met Asn Asn His Leu Leu Asp Leu Leu Ser Lys Val Gln Thr Asn Leu
 1               5                  10                  15

Phe Val Leu Lys Glu His Lys Asn Ile Leu Ser Glu Phe Leu Asp Leu
            20                  25                  30

Leu Asn Ile Asp Ser Ser Asp Lys Ser Leu Ile Gln Asn His Phe Gln
        35                  40                  45

Ile Phe Arg Asn Thr Leu Leu Asn Ile Glu Asn His Met Asp Ser Leu
    50                  55                  60

Lys Asn Glu Ile Ser Val Ile Asn Pro Ala Val Phe Ala Thr Val Ser
65                  70                  75                  80

Gly Ser Ile Lys Ile Asn Lys Ile Asn Tyr Thr Phe Ala Glu Val Lys
                85                  90                  95

Tyr Ser Glu Asn Asp Ala Ser Gly Lys Pro Lys Arg Gly Ile Glu Phe
            100                 105                 110

Lys Pro Gly Gly Asn Arg Tyr Val Ile Ser Pro Asn Pro His Leu Asn
        115                 120                 125

Asn Gln Tyr Asn Asn Ser Gly Gln Arg Gln Phe Tyr Ser Ala Leu Ala
    130                 135                 140

Leu Asn Ile Ser Tyr Arg Gly Asp Asp Glu His Trp Glu Lys Asn Asn
145                 150                 155                 160

Trp Pro Thr Lys Thr Gln Asp Arg Ile Thr Ala Leu Gly Gln Lys Tyr
                165                 170                 175

Thr Leu Thr Tyr Asp Gly Lys Ala
            180
```

<210> SEQ ID NO 72
<211> LENGTH: 753
<212> TYPE: DNA
<213> ORGANISM: Artificial Sequence
<220> FEATURE:
<223> OTHER INFORMATION: Maize optimized

<400> SEQUENCE: 72

```
atggctcaat ctagcagaat ctgccacggt gtgcagaacc catgtgtgat catttccaat      60
ctctccaaat ccaaccagaa caaatctcct ttctcagtca gcctcaagac tcaccagcag     120
cagcgtcgtg cttaccagat atctagctgg ggattgaaga agtcaaacaa cgggtccgtg     180
attcgtccgg ttaaggcaat gaacaaccac ctgcttgacc tgctgtccaa ggtgcagacc     240
aacctgttcg tgctgaagga gcacaagaac atcctgagcg agttcctgga cctgctgaat     300
atcgactcct ccgacaagag cctgatccag aaccactttc agatattccg gaacaccctg     360
ctgaacatcg agaaccacat ggactccctg aagaacgaga tttccgtgat caacccagcg     420
gtgttcgcga ccgtgagcgg cagcatcaag atcaacaaga tcaactacac cttcgccgag     480
gtgaagtaca gcgagaacga cgcctccggc aagcctaaga ggggcatcga gttcaaaccg     540
ggtggcaaca gatacgtgat cagcccgaac ccgcacctga caaccagta caacaactcc     600
ggacagaggc agttctactc cgcactggcg ctgaacatct catacagagg cgacgacgag     660
cactgggaga agaacaactg gccgaccaag acccaagata ggatcaccgc gctgggccag     720
aagtacaccc tgacctacga cggcaaggcc tga                                 753
```

<210> SEQ ID NO 73
<211> LENGTH: 753
<212> TYPE: DNA
<213> ORGANISM: Artificial Sequence
<220> FEATURE:
<223> OTHER INFORMATION: Maize optimized

<400> SEQUENCE: 73

```
atggctcaat ctagcagaat ctgccacggt gtgcagaacc catgtgtgat catttccaat      60
ctctccaaat ccaaccagaa caaatctcct ttctcagtca gcctcaagac tcaccagcag     120
cagcgtcgtg cttaccagat atctagctgg ggattgaaga agtcaaacaa cgggtccgtg     180
attcgtccgg ttaaggcaat gaataatcac ctgcttgacc tgctgtccaa ggtgcagacc     240
aacctgttcg tgctgaagga gcacaaaaat atcctgagcg agttcctgga cctattaaat     300
atcgactcct ccgacaagag cctgatccag aaccactttc agatattccg gaacaccctg     360
ctgaacatcg agaaccacat ggactccctg aagaatgaaa tttccgtaat aaacccagcg     420
gtgttcgcga ccgtgagcgg cagcattaaa ataaacaaaa tcaactatac attcgccgag     480
gtgaagtaca gcgagaacga cgcctccggc aagcctaaga ggggcatcga gttcaaaccg     540
ggtggcaaca gatacgtgat cagcccgaac ccgcacctga ataatcaata caacaactcc     600
ggacagaggc agttctactc cgcactggca ttaaacatct catacagagg cgacgacgag     660
cactgggaga aaaataattg gccgaccaag acccaagata ggatcaccgc gctgggccaa     720
aaatataccc tgacctacga cggcaaggcc tga                                 753
```

<210> SEQ ID NO 74
<211> LENGTH: 250
<212> TYPE: PRT
<213> ORGANISM: Artificial Sequence
<220> FEATURE:

<223> OTHER INFORMATION: translated from synthesized maize optimized coding region

<400> SEQUENCE: 74

```
Met Ala Gln Ser Ser Arg Ile Cys His Gly Val Gln Asn Pro Cys Val
1               5                   10                  15
Ile Ile Ser Asn Leu Ser Lys Ser Asn Gln Asn Lys Ser Pro Phe Ser
            20                  25                  30
Val Ser Leu Lys Thr His Gln Gln Arg Arg Ala Tyr Gln Ile Ser
        35                  40                  45
Ser Trp Gly Leu Lys Lys Ser Asn Asn Gly Ser Val Ile Arg Pro Val
    50                  55                  60
Lys Ala Met Asn Asn His Leu Leu Asp Leu Leu Ser Lys Val Gln Thr
65                  70                  75                  80
Asn Leu Phe Val Leu Lys Glu His Lys Asn Ile Leu Ser Glu Phe Leu
                85                  90                  95
Asp Leu Leu Asn Ile Asp Ser Ser Asp Lys Ser Leu Ile Gln Asn His
            100                 105                 110
Phe Gln Ile Phe Arg Asn Thr Leu Leu Asn Ile Glu Asn His Met Asp
        115                 120                 125
Ser Leu Lys Asn Glu Ile Ser Val Ile Asn Pro Ala Val Phe Ala Thr
    130                 135                 140
Val Ser Gly Ser Ile Lys Ile Asn Lys Ile Asn Tyr Thr Phe Ala Glu
145                 150                 155                 160
Val Lys Tyr Ser Glu Asn Asp Ala Ser Gly Lys Pro Lys Arg Gly Ile
                165                 170                 175
Glu Phe Lys Pro Gly Gly Asn Arg Tyr Val Ile Ser Pro Asn Pro His
            180                 185                 190
Leu Asn Asn Gln Tyr Asn Asn Ser Gly Gln Arg Gln Phe Tyr Ser Ala
        195                 200                 205
Leu Ala Leu Asn Ile Ser Tyr Arg Gly Asp Asp Glu His Trp Glu Lys
    210                 215                 220
Asn Asn Trp Pro Thr Lys Thr Gln Asp Arg Ile Thr Ala Leu Gly Gln
225                 230                 235                 240
Lys Tyr Thr Leu Thr Tyr Asp Gly Lys Ala
                245                 250
```

<210> SEQ ID NO 75
<211> LENGTH: 768
<212> TYPE: DNA
<213> ORGANISM: Artificial Sequence
<220> FEATURE:
<223> OTHER INFORMATION: Maize optimized

<400> SEQUENCE: 75

```
atgttggctc gccaaggagg atcactgaga gcctctcagt gtaacgctgg cctcgcgaga     60
cgcgtggagg tgggagcgtt ggttgttccg agacccataa gcgtcaacga cgtggttccc    120
catgtctatt cggctcctct gagcgtcgcg aggaggtcgt gctccaagtc atccatccgc    180
tcgactcgca gacttcagac aaccgtctgc tccatgaata atcacctgct tgacctgctg    240
tccaaggtgc agaccaacct gttcgtgctg aaggagcaca aaaatatcct gagcgagttc    300
ctggacctat taaatatcga ctcctccgac aagagcctga tccagaacca ctttcagata    360
ttccggaaca ccctgctgaa catcgagaac cacatggact ccctgaagaa tgaaatttcc    420
gtaataaaacc cagcggtgtt cgcgaccgtg agcggcagca ttaaaataaa caaaatcaac    480
```

```
tatacattcg ccgaggtgaa gtacagcgag aacgacgcct ccggcaagcc taagaggggc    540
atcgagttca aaccgggtgg caacagatac gtgatcagcc cgaacccgca cctgaataat    600
caatacaaca actccggaca gaggcagttc tactccgcac tggcattaaa catctcatac    660
agaggcgacg acgagcactg ggagaaaaat aattggccga ccaagaccca agataggatc    720
accgcgctgg gccaaaaata taccctgacc tacgacggca aggcctga                 768
```

```
<210> SEQ ID NO 76
<211> LENGTH: 255
<212> TYPE: PRT
<213> ORGANISM: Artificial Sequence
<220> FEATURE:
<223> OTHER INFORMATION: translated from synthesized maize optimized
      coding region

<400> SEQUENCE: 76
```

Met Leu Ala Arg Gln Gly Gly Ser Leu Arg Ala Ser Gln Cys Asn Ala
1               5                   10                  15

Gly Leu Ala Arg Arg Val Glu Val Gly Ala Leu Val Val Pro Arg Pro
            20                  25                  30

Ile Ser Val Asn Asp Val Val Pro His Val Tyr Ser Ala Pro Leu Ser
        35                  40                  45

Val Ala Arg Arg Ser Cys Ser Lys Ser Ser Ile Arg Ser Thr Arg Arg
    50                  55                  60

Leu Gln Thr Thr Val Cys Ser Met Asn Asn His Leu Leu Asp Leu Leu
65                  70                  75                  80

Ser Lys Val Gln Thr Asn Leu Phe Val Leu Lys Glu His Lys Asn Ile
                85                  90                  95

Leu Ser Glu Phe Leu Asp Leu Leu Asn Ile Asp Ser Ser Asp Lys Ser
            100                 105                 110

Leu Ile Gln Asn His Phe Gln Ile Phe Arg Asn Thr Leu Leu Asn Ile
        115                 120                 125

Glu Asn His Met Asp Ser Leu Lys Asn Glu Ile Ser Val Ile Asn Pro
    130                 135                 140

Ala Val Phe Ala Thr Val Ser Gly Ser Ile Lys Ile Asn Lys Ile Asn
145                 150                 155                 160

Tyr Thr Phe Ala Glu Val Lys Tyr Ser Glu Asn Asp Ala Ser Gly Lys
                165                 170                 175

Pro Lys Arg Gly Ile Glu Phe Lys Pro Gly Gly Asn Arg Tyr Val Ile
            180                 185                 190

Ser Pro Asn Pro His Leu Asn Asn Gln Tyr Asn Asn Ser Gly Gln Arg
        195                 200                 205

Gln Phe Tyr Ser Ala Leu Ala Leu Asn Ile Ser Tyr Arg Gly Asp Asp
    210                 215                 220

Glu His Trp Glu Lys Asn Asn Trp Pro Thr Lys Thr Gln Asp Arg Ile
225                 230                 235                 240

Thr Ala Leu Gly Gln Lys Tyr Thr Leu Thr Tyr Asp Gly Lys Ala
                245                 250                 255

```
<210> SEQ ID NO 77
<211> LENGTH: 981
<212> TYPE: DNA
<213> ORGANISM: Artificial Sequence
<220> FEATURE:
<223> OTHER INFORMATION: IRDIG27501.2 and IRDIG27642.2 fused with a 2A
      sequence

<400> SEQUENCE: 77
```

-continued

```
atggctaact gcaacaccga aaggactac gacggctact acgagctgcc ggagcctggt      60
gcgaggctgg ggagctgcgt gggcctgtac accggactgg acctgtgcta cagcgtggac    120
gcagccaacc tgagcgtggc catcgacatt aaagtgttcg gcgtgagggt ggagcacggc    180
gagatcggca tcggcaagcc gttcaccacc accgtgggcg tgggaccagc caccgcgaag    240
atcacgatct cagtggtgaa ggagggcaat aaacactgcc tgaatatcca gtacaacgtc    300
cacctgccgt tcctgggcaa cgtggctcac ggcaataaag acgtggtgtg cttcagatct    360
ggcggcggag agggcagagg aagtcttcta acatgcggtg acgtggagga gaatcccggc    420
cctaggatga taatcacct gcttgacctg ctgtccaagg tgcagaccaa cctgttcgtg     480
ctgaaggagc acaaaaatat cctgagcgag ttcctggacc tattaaatat cgactcctcc    540
gacaagagcc tgatccagaa ccactttcag atattccgga cacccctgct gaacatcgag    600
aaccacatgg actccctgaa gaatgaaatt ccgtaataa acccagcggt gttcgcgacc     660
gtgagcggca gcattaaaat aaacaaaatc aactatacat tcgccgaggt gaagtacagc    720
gagaacgacg cctccggcaa gcctaagagg ggcatcgagt tcaaaccggg tggcaacaga    780
tacgtgatca gcccgaaccc gcacctgaat aatcaataca caactccgg acagaggcag     840
ttctactccg cactggcatt aaacatctca tacagaggcg acgacgagca ctgggagaaa    900
aataattggc cgaccaagac ccaagatagg atcaccgcgc tgggccaaaa atataccctg    960
acctacgacg gcaaggcctg a                                              981
```

<210> SEQ ID NO 78
<211> LENGTH: 326
<212> TYPE: PRT
<213> ORGANISM: Artificial Sequence
<220> FEATURE:
<223> OTHER INFORMATION: translated from synthesized fused coding region

<400> SEQUENCE: 78

Met Ala Asn Cys Asn Thr Glu Lys Asp Tyr Asp Gly Tyr Tyr Glu Leu
1               5                   10                  15

Pro Glu Pro Gly Ala Arg Leu Gly Ser Cys Val Gly Leu Tyr Thr Gly
            20                  25                  30

Leu Asp Leu Cys Tyr Ser Val Asp Ala Ala Asn Leu Ser Val Ala Ile
        35                  40                  45

Asp Ile Lys Val Phe Gly Val Arg Val Glu His Gly Glu Ile Gly Ile
    50                  55                  60

Gly Lys Pro Phe Thr Thr Thr Val Gly Val Gly Pro Ala Thr Ala Lys
65                  70                  75                  80

Ile Thr Ile Ser Val Val Lys Glu Gly Asn Lys His Cys Leu Asn Ile
                85                  90                  95

Gln Tyr Asn Val His Leu Pro Phe Leu Gly Asn Val Ala His Gly Asn
            100                 105                 110

Lys Asp Val Val Cys Phe Arg Ser Gly Gly Gly Glu Gly Arg Gly Ser
        115                 120                 125

Leu Leu Thr Cys Gly Asp Val Glu Glu Asn Pro Gly Pro Arg Met Asn
    130                 135                 140

Asn His Leu Leu Asp Leu Leu Ser Lys Val Gln Thr Asn Leu Phe Val
145                 150                 155                 160

Leu Lys Glu His Lys Asn Ile Leu Ser Glu Phe Leu Asp Leu Leu Asn
                165                 170                 175

Ile Asp Ser Ser Asp Lys Ser Leu Ile Gln Asn His Phe Gln Ile Phe

```
                180             185             190
Arg Asn Thr Leu Leu Asn Ile Glu Asn His Met Asp Ser Leu Lys Asn
                    195             200             205
Glu Ile Ser Val Ile Asn Pro Ala Val Phe Ala Thr Val Ser Gly Ser
        210             215             220
Ile Lys Ile Asn Lys Ile Asn Tyr Thr Phe Ala Glu Val Lys Tyr Ser
225             230             235             240
Glu Asn Asp Ala Ser Gly Lys Pro Lys Arg Gly Ile Glu Phe Lys Pro
                    245             250             255
Gly Gly Asn Arg Tyr Val Ile Ser Pro Asn Pro His Leu Asn Asn Gln
            260             265             270
Tyr Asn Asn Ser Gly Gln Arg Gln Phe Tyr Ser Ala Leu Ala Leu Asn
        275             280             285
Ile Ser Tyr Arg Gly Asp Asp Glu His Trp Glu Lys Asn Asn Trp Pro
            290             295             300
Thr Lys Thr Gln Asp Arg Ile Thr Ala Leu Gly Gln Lys Tyr Thr Leu
305             310             315             320
Thr Tyr Asp Gly Lys Ala
                325

<210> SEQ ID NO 79
<211> LENGTH: 981
<212> TYPE: DNA
<213> ORGANISM: Artificial Sequence
<220> FEATURE:
<223> OTHER INFORMATION: IRDIG27642.2 and IRDIG27501.2 fused with a 2A
      sequence

<400> SEQUENCE: 79
atgaataatc acctgcttga cctgctgtcc aaggtgcaga ccaacctgtt cgtgctgaag     60
gagcacaaaa atatcctgag cgagttcctg gacctattaa atatcgactc ctccgacaag    120
agcctgatcc agaaccactt tcagatattc cggaacaccc tgctgaacat cgagaaccac    180
atggactccc tgaagaatga atttccgta ataaacccag cggtgttcgc gaccgtgagc     240
ggcagcatta aaataaacaa aatcaactat acattcgccg aggtgaagta cagcgagaac    300
gacgcctccg gcaagcctaa gaggggcatc gagttcaaac cgggtggcaa cagatacgtg    360
atcagcccga acccgcacct gaataatcaa tacaacaact ccggacagag gcagttctac    420
tccgcactgg cattaaacat ctcatacaga ggcgacgacg agcactggga gaaaaataat    480
tggccgacca agacccaaga taggatcacc gcgctgggcc aaaaatatac cctgacctac    540
gacggcaagg ccagatctgg cggcggagag ggcagaggaa gtcttctaac atgcggtgac    600
gtggaggaga tcccggccc taggatggct aactgcaaca ccgagaagga ctacgacggc    660
tactacgagc tgccggagcc tggtgcgagg ctggggagct gcgtgggcct gtacaccgga    720
ctggacctgt gctacagcgt ggacgcagcc aacctgagcg tggccatcga cattaaagtg    780
ttcggcgtga gggtggagca cggcgagatc ggcatcggca gccgttcac caccaccgtg    840
ggcgtgggac cagccaccgc gaagatcacg atctcagtgg tgaaggaggg caataaacac    900
tgcctgaata tccagtacaa cgtccacctg ccgttcctgg caacgtggc tcacggcaat    960
aaagacgtgg tgtgcttctg a                                              981

<210> SEQ ID NO 80
<211> LENGTH: 326
<212> TYPE: PRT
<213> ORGANISM: Artificial Sequence
```

<220> FEATURE:
<223> OTHER INFORMATION: translated from synthesized fused coding region

<400> SEQUENCE: 80

```
Met Asn Asn His Leu Leu Asp Leu Leu Ser Lys Val Gln Thr Asn Leu
1               5                   10                  15

Phe Val Leu Lys Glu His Lys Asn Ile Leu Ser Glu Phe Leu Asp Leu
            20                  25                  30

Leu Asn Ile Asp Ser Ser Asp Lys Ser Leu Ile Gln Asn His Phe Gln
        35                  40                  45

Ile Phe Arg Asn Thr Leu Leu Asn Ile Glu Asn His Met Asp Ser Leu
50                  55                  60

Lys Asn Glu Ile Ser Val Ile Asn Pro Ala Val Phe Ala Thr Val Ser
65                  70                  75                  80

Gly Ser Ile Lys Ile Asn Lys Ile Asn Tyr Thr Phe Ala Glu Val Lys
                85                  90                  95

Tyr Ser Glu Asn Asp Ala Ser Gly Lys Pro Lys Arg Gly Ile Glu Phe
            100                 105                 110

Lys Pro Gly Gly Asn Arg Tyr Val Ile Ser Pro Asn Pro His Leu Asn
        115                 120                 125

Asn Gln Tyr Asn Asn Ser Gly Gln Arg Gln Phe Tyr Ser Ala Leu Ala
130                 135                 140

Leu Asn Ile Ser Tyr Arg Gly Asp Asp Glu His Trp Glu Lys Asn Asn
145                 150                 155                 160

Trp Pro Thr Lys Thr Gln Asp Arg Ile Thr Ala Leu Gly Gln Lys Tyr
                165                 170                 175

Thr Leu Thr Tyr Asp Gly Lys Ala Arg Ser Gly Gly Glu Gly Arg
            180                 185                 190

Gly Ser Leu Leu Thr Cys Gly Asp Val Glu Glu Asn Pro Gly Pro Arg
        195                 200                 205

Met Ala Asn Cys Asn Thr Glu Lys Asp Tyr Asp Gly Tyr Tyr Glu Leu
210                 215                 220

Pro Glu Pro Gly Ala Arg Leu Gly Ser Cys Val Gly Leu Tyr Thr Gly
225                 230                 235                 240

Leu Asp Leu Cys Tyr Ser Val Asp Ala Ala Asn Leu Ser Val Ala Ile
                245                 250                 255

Asp Ile Lys Val Phe Gly Val Arg Val Glu His Gly Glu Ile Gly Ile
            260                 265                 270

Gly Lys Pro Phe Thr Thr Thr Val Gly Val Gly Pro Ala Thr Ala Lys
        275                 280                 285

Ile Thr Ile Ser Val Val Lys Glu Gly Asn Lys His Cys Leu Asn Ile
290                 295                 300

Gln Tyr Asn Val His Leu Pro Phe Leu Gly Asn Val Ala His Gly Asn
305                 310                 315                 320

Lys Asp Val Val Cys Phe
                325
```

<210> SEQ ID NO 81
<211> LENGTH: 324
<212> TYPE: DNA
<213> ORGANISM: Bacillus thuringiensis

<400> SEQUENCE: 81
acagttagtg gatctattaa aataaacaaa atcaactata catttgctga agttaagtat    60
agtgaaaatg atgcaagtgg aaaacctaaa agaggaattg aatttaaacc tggcggaaat   120
cgatatgtaa tatctcctaa tccacatttg aataatcaat acaacaatag tggacaacga      180
caattttata gtgctttagc attaaatatt agctacagag gtgatgatga acattgggaa      240
aaaaataatt ggccaacaaa aactcaagat cgtattactg cacttggcca aaaatatact      300
ttaacatatg atggtaaagc ttaa                                             324

<210> SEQ ID NO 82
<211> LENGTH: 107
<212> TYPE: PRT
<213> ORGANISM: Bacillus thuringiensis

<400> SEQUENCE: 82

Thr Val Ser Gly Ser Ile Lys Ile Asn Lys Ile Asn Tyr Thr Phe Ala
1               5                   10                  15

Glu Val Lys Tyr Ser Glu Asn Asp Ala Ser Gly Lys Pro Lys Arg Gly
            20                  25                  30

Ile Glu Phe Lys Pro Gly Gly Asn Arg Tyr Val Ile Ser Pro Asn Pro
        35                  40                  45

His Leu Asn Asn Gln Tyr Asn Asn Ser Gly Gln Arg Gln Phe Tyr Ser
    50                  55                  60

Ala Leu Ala Leu Asn Ile Ser Tyr Arg Gly Asp Asp Glu His Trp Glu
65                  70                  75                  80

Lys Asn Asn Trp Pro Thr Lys Thr Gln Asp Arg Ile Thr Ala Leu Gly
                85                  90                  95

Gln Lys Tyr Thr Leu Thr Tyr Asp Gly Lys Ala
            100                 105

<210> SEQ ID NO 83
<211> LENGTH: 297
<212> TYPE: DNA
<213> ORGANISM: Bacillus thuringiensis

<400> SEQUENCE: 83
gcaagattag gaagttgtgt tggattatat acaggattag acttatgtta tagcgttgat       60
gccgcgaatt tatctgttgc tatagatatt aaagtgtttg gtgtaagagt ggagcatggt      120
gaaattggta taggtaagcc attcactact actgttggtg taggaccagc aacagcaaag      180
attacaattt ctgtagttaa agaaggaaat aaacattgtt taaatattca gtataatgtt      240
cacttacctt tccttggaaa tgtagcacat ggaaataaag atgtagtttg tttttaa         297

<210> SEQ ID NO 84
<211> LENGTH: 98
<212> TYPE: PRT
<213> ORGANISM: Bacillus thuringiensis

<400> SEQUENCE: 84

Ala Arg Leu Gly Ser Cys Val Gly Leu Tyr Thr Gly Leu Asp Leu Cys
1               5                   10                  15

Tyr Ser Val Asp Ala Ala Asn Leu Ser Val Ala Ile Asp Ile Lys Val
            20                  25                  30

Phe Gly Val Arg Val Glu His Gly Glu Ile Gly Ile Gly Lys Pro Phe
        35                  40                  45

Thr Thr Thr Val Gly Val Gly Pro Ala Thr Ala Lys Ile Thr Ile Ser
    50                  55                  60

Val Val Lys Glu Gly Asn Lys His Cys Leu Asn Ile Gln Tyr Asn Val
65                  70                  75                  80

His Leu Pro Phe Leu Gly Asn Val Ala His Gly Asn Lys Asp Val Val
            85                  90                  95

Cys Phe

<210> SEQ ID NO 85
<211> LENGTH: 324
<212> TYPE: DNA
<213> ORGANISM: Bacillus thuringiensis

<400> SEQUENCE: 85
gcagttagtg gatctatccc aataaataat gtaaaatata catttgctga agttcagtac      60
agtggaaatg atgacagtgg aaaacctaaa agaggaatcg aatttaaatc aggaggaaac     120
cgatacgtaa tatctcctaa tccacattta aataatcgat ataacggtgg tggacaacga     180
gatttttata tgctttagc attaaaagtt agcgatatcg gtgatgatga acattgggaa      240
aaaaacaact ggccaacaaa gaatttaacg cgtcttagtg cacttggtca aaaatatgat     300
ttacattatg atggtagagc ttaa                                            324

<210> SEQ ID NO 86
<211> LENGTH: 107
<212> TYPE: PRT
<213> ORGANISM: Bacillus thuringiensis

<400> SEQUENCE: 86

Ala Val Ser Gly Ser Ile Pro Ile Asn Asn Val Lys Tyr Thr Phe Ala
1               5                   10                  15

Glu Val Gln Tyr Ser Gly Asn Asp Asp Ser Gly Lys Pro Lys Arg Gly
            20                  25                  30

Ile Glu Phe Lys Ser Gly Gly Asn Arg Tyr Val Ile Ser Pro Asn Pro
        35                  40                  45

His Leu Asn Asn Arg Tyr Asn Gly Gly Gln Arg Asp Phe Tyr Asn
    50                  55                  60

Ala Leu Ala Leu Lys Val Ser Asp Ile Gly Asp Asp Glu His Trp Glu
65                  70                  75                  80

Lys Asn Asn Trp Pro Thr Lys Asn Leu Thr Arg Leu Ser Ala Leu Gly
                85                  90                  95

Gln Lys Tyr Asp Leu His Tyr Asp Gly Arg Ala
            100                 105

<210> SEQ ID NO 87
<211> LENGTH: 327
<212> TYPE: DNA
<213> ORGANISM: Bacillus thuringiensis

<400> SEQUENCE: 87
acagttagcg gaaaaataat aataaatact attaaatata cattcgcaga agttcaatat      60
agtggaaatg atgaaagtgg tagacctaaa agagggattg agtttaaacc aggaggaaat     120
cgatatatta tttctcctaa tccacattta aataataaat ataatacttc aaatggtcca     180
atacaatttt ataatgcttt agcattaaat cttagttata aaggagatga tgaacagtgg     240
gtaaagggga attggccaaa aacaaatcta agtggtctta attcgcttgg acaaaaatat     300
attttaaaat atgacagtag taattaa                                         327

<210> SEQ ID NO 88
<211> LENGTH: 108
<212> TYPE: PRT
<213> ORGANISM: Bacillus thuringiensis

<400> SEQUENCE: 88

Thr Val Ser Gly Lys Ile Ile Ile Asn Thr Ile Lys Tyr Thr Phe Ala
1               5                   10                  15

Glu Val Gln Tyr Ser Gly Asn Asp Glu Ser Gly Arg Pro Lys Arg Gly
            20                  25                  30

Ile Glu Phe Lys Pro Gly Gly Asn Arg Tyr Ile Ile Ser Pro Asn Pro
        35                  40                  45

His Leu Asn Asn Lys Tyr Asn Thr Ser Asn Gly Pro Ile Gln Phe Tyr
    50                  55                  60

Asn Ala Leu Ala Leu Asn Leu Ser Tyr Lys Gly Asp Asp Glu Gln Trp
65                  70                  75                  80

Val Lys Gly Asn Trp Pro Lys Thr Asn Leu Ser Gly Leu Asn Ser Leu
                85                  90                  95

Gly Gln Lys Tyr Ile Leu Lys Tyr Asp Ser Ser Asn
            100                 105

<210> SEQ ID NO 89
<211> LENGTH: 333
<212> TYPE: DNA
<213> ORGANISM: Bacillus thuringiensis

<400> SEQUENCE: 89
gcagtatctg gaacgattat tatcaataat aaaaattata catttgtaga agtgcaatat      60
agccaaagtg atcaatatgg accaaaaaga ggaattaaat ttacaggtgg aggaaatgaa     120
tatttaattg atcccaatcc acatgaaaat ggacaatatc aaaaaaacgc cagacaattt     180
tatagtgctt tagcatatgg tatacaaggg aagtctataa cagatggaca aaatgggcat     240
ccttgggtac aaaataattg gcccacaggc aatcaagatc ggattaatgc actaggagaa     300
agatatacat tacaatacaa aggtagagct taa                                  333

<210> SEQ ID NO 90
<211> LENGTH: 333
<212> TYPE: DNA
<213> ORGANISM: Bacillus thuringiensis

<400> SEQUENCE: 90
gcagtatctg gaacgattat tatcaataat aaaaattata catttgtaga agtgcaatat      60
agccaaagtg atcaatatgg accaaaaaga gggattaaat ttacaggtgg aggaaatgaa     120
tatttaattg atcccaatcc acatgaaaat ggacaatatc aaaaaaacgc cagacaattt     180
tatagtgctt tagcatatgg tatacaaggg aagtctataa cagatggaca aaatgggcat     240
ccttgggtac aaaataattg gcccacaggc aatcaagatc ggattaatgc actaggagaa     300
agatatacat tacaatacaa aggtagagct taa                                  333

<210> SEQ ID NO 91
<211> LENGTH: 110
<212> TYPE: PRT
<213> ORGANISM: Bacillus thuringiensis

<400> SEQUENCE: 91

Ala Val Ser Gly Thr Ile Ile Ile Asn Asn Lys Asn Tyr Thr Phe Val
1               5                   10                  15

Glu Val Gln Tyr Ser Gln Ser Asp Gln Tyr Gly Pro Lys Arg Gly Ile
            20                  25                  30

Lys Phe Thr Gly Gly Gly Asn Glu Tyr Leu Ile Asp Pro Asn Pro His

```
                 35                  40                  45

Glu Asn Gly Gln Tyr Gln Lys Asn Ala Arg Gln Phe Tyr Ser Ala Leu
             50                  55                  60

Ala Tyr Gly Ile Gln Gly Lys Ser Ile Thr Asp Gly Gln Asn Gly His
 65                  70                  75                  80

Pro Trp Val Gln Asn Asn Trp Pro Thr Gly Asn Gln Asp Arg Ile Asn
                 85                  90                  95

Ala Leu Gly Glu Arg Tyr Thr Leu Gln Tyr Lys Gly Arg Ala
            100                 105                 110

<210> SEQ ID NO 92
<211> LENGTH: 333
<212> TYPE: DNA
<213> ORGANISM: Bacillus thuringiensis

<400> SEQUENCE: 92
gcagtatctg gaacgattat tatcaataat aaaaattata catttgtaga agtgcaatat      60
agccaaagtg atcaatatgg accaaaaaga gggattaaat ttacaggtgg aggaaatgaa     120
tatttaattg atcccaatcc acatgaaaat ggacaatatc aaaaaaacgc cagacaattt     180
tatagtgctt tagcatatgg tatacaaggg aagtctataa cagatggaca aaatgggcat     240
ccttgggtac aaataattg gcccacaggc aatcaagatc ggattaatgc actaggagaa     300
agatatacat tacaatacaa aggtagagct taa                                 333

<210> SEQ ID NO 93
<211> LENGTH: 110
<212> TYPE: PRT
<213> ORGANISM: Bacillus thuringiensis

<400> SEQUENCE: 93

Ala Val Ser Gly Thr Ile Ile Ile Asn Asn Lys Asn Tyr Thr Phe Val
  1               5                  10                  15

Glu Val Gln Tyr Ser Gln Ser Asp Gln Tyr Gly Pro Lys Arg Gly Ile
             20                  25                  30

Lys Phe Thr Gly Gly Gly Asn Glu Tyr Leu Ile Asp Pro Asn Pro His
         35                  40                  45

Glu Asn Gly Gln Tyr Gln Lys Asn Ala Arg Gln Phe Tyr Ser Ala Leu
             50                  55                  60

Ala Tyr Gly Ile Gln Gly Lys Ser Ile Thr Asp Gly Gln Asn Gly His
 65                  70                  75                  80

Pro Trp Val Pro Asn Asn Trp Pro Thr Gly Asn Gln Asp Arg Ile Asn
                 85                  90                  95

Ala Leu Gly Glu Arg Tyr Thr Leu Gln Tyr Lys Gly Arg Ala
            100                 105                 110

<210> SEQ ID NO 94
<211> LENGTH: 333
<212> TYPE: DNA
<213> ORGANISM: Bacillus thuringiensis

<400> SEQUENCE: 94
gcagtatctg gaacgattat tatcaataat aaaaattata cctttgtaga agtacaatat      60
agccaaagtg atcaatatgg accaaaaaga gggattaaat ttacaggtgg aggaaatgaa     120
tatttaattg atcccaatcc acatgaaaat ggacaatatc aaaaaaacgc tagacaattt     180
tatagtgctt tagcatatgg tatacaaggg aagtctataa cagatggaca aaatgggcat     240
```

```
cctttgggtac aaaataattg gcccacagtc aatcaagatc ggattaatgc actaggagaa      300
agatatacat tacaatacaa aggtagggct taa                                    333
```

<210> SEQ ID NO 95
<211> LENGTH: 110
<212> TYPE: PRT
<213> ORGANISM: Bacillus thuringiensis

<400> SEQUENCE: 95

```
Ala Val Ser Gly Thr Ile Ile Asn Asn Lys Asn Tyr Thr Phe Val
1               5                   10                  15

Glu Val Gln Tyr Ser Gln Ser Asp Gln Tyr Gly Pro Lys Arg Gly Ile
            20                  25                  30

Lys Phe Thr Gly Gly Gly Asn Glu Tyr Leu Ile Asp Pro Asn Pro His
        35                  40                  45

Glu Asn Gly Gln Tyr Gln Lys Asn Ala Arg Gln Phe Tyr Ser Ala Leu
    50                  55                  60

Ala Tyr Gly Ile Gln Gly Lys Ser Ile Thr Asp Gly Gln Asn Gly His
65                  70                  75                  80

Pro Trp Val Gln Asn Asn Trp Pro Thr Val Asn Gln Asp Arg Ile Asn
                85                  90                  95

Ala Leu Gly Glu Arg Tyr Thr Leu Gln Tyr Lys Gly Arg Ala
            100                 105                 110
```

<210> SEQ ID NO 96
<211> LENGTH: 324
<212> TYPE: DNA
<213> ORGANISM: Bacillus thuringiensis

<400> SEQUENCE: 96

```
gcaacagtta gtggatctat tcaaataaac aaggttaaat atacatttgc tgaagttcag       60
tacagtggaa atgatgaaag tggaaaacct aaaagaggaa ttgaatttaa atccggtgga      120
aatcgatatg taatctctcc taatccacat ttaaataata gatataacaa tggtggacaa      180 cgagatttt ataatgcttt agcattaaaa gttagcgata taggtgatga tgaaaaatgg      240 gaaaaaatg aatggccaac aaaaaatcta acacatctta gtgcgcttgg tcaaaaatat      300
gatttacatt atgatggcag agct                                            324
```

<210> SEQ ID NO 97
<211> LENGTH: 108
<212> TYPE: PRT
<213> ORGANISM: Bacillus thuringiensis

<400> SEQUENCE: 97

```
Ala Thr Val Ser Gly Ser Ile Gln Ile Asn Lys Val Lys Tyr Thr Phe
1               5                   10                  15

Ala Glu Val Gln Tyr Ser Gly Asn Asp Glu Ser Gly Lys Pro Lys Arg
            20                  25                  30

Gly Ile Glu Phe Lys Ser Gly Gly Asn Arg Tyr Val Ile Ser Pro Asn
        35                  40                  45

Pro His Leu Asn Asn Arg Tyr Asn Asn Gly Gly Gln Arg Asp Phe Tyr
    50                  55                  60

Asn Ala Leu Ala Leu Lys Val Ser Asp Ile Gly Asp Asp Glu Lys Trp
65                  70                  75                  80

Glu Lys Asn Glu Trp Pro Thr Lys Asn Leu Thr His Leu Ser Ala Leu
                85                  90                  95
```

Gly Gln Lys Tyr Asp Leu His Tyr Asp Gly Arg Ala
            100                 105

<210> SEQ ID NO 98
<211> LENGTH: 342
<212> TYPE: DNA
<213> ORGANISM: Bacillus thuringiensis

<400> SEQUENCE: 98
gcaacagtta gtgggtctat tacaataaat aatgtcaaat atacatttgc tgaagttcaa    60
tacagtggaa atgatgaaag tggacgtcct aaaagaggaa ttgaatttaa accagggga   120 aatcgatacg taatatctcc taatccacat ttgaataatc aatataacag caatggacaa   180
cgacagtttt atagtgcttt agcatatggt atacaaacca atctataaa cgatggaaat    240 actggacact cttgggagaa aagcaattgg ccaacaataa atcaagatcg tataaatgca   300
cttggggtaa gatatacttt gaaatatgat ggtagagctt ag                     342

<210> SEQ ID NO 99
<211> LENGTH: 113
<212> TYPE: PRT
<213> ORGANISM: Bacillus thuringiensis

<400> SEQUENCE: 99

Ala Thr Val Ser Gly Ser Ile Thr Ile Asn Asn Val Lys Tyr Thr Phe
1               5                   10                  15

Ala Glu Val Gln Tyr Ser Gly Asn Asp Glu Ser Gly Arg Pro Lys Arg
            20                  25                  30

Gly Ile Glu Phe Lys Pro Gly Gly Asn Arg Tyr Val Ile Ser Pro Asn
        35                  40                  45

Pro His Leu Asn Asn Gln Tyr Asn Ser Asn Gly Gln Arg Gln Phe Tyr
    50                  55                  60

Ser Ala Leu Ala Tyr Gly Ile Gln Thr Lys Ser Ile Asn Asp Gly Asn
65                  70                  75                  80

Thr Gly His Ser Trp Glu Lys Ser Asn Trp Pro Thr Ile Asn Gln Asp
                85                  90                  95

Arg Ile Asn Ala Leu Gly Val Arg Tyr Thr Leu Lys Tyr Asp Gly Arg
            100                 105                 110

Ala

<210> SEQ ID NO 100
<211> LENGTH: 333
<212> TYPE: DNA
<213> ORGANISM: Bacillus thuringiensis

<400> SEQUENCE: 100
gcagtatctg gaacgattat tatcaataat aaaaattata catttgtaga agtgcaatat    60
agccaaagtg atccatatgg actgaaaaga gggattaaat ttacaggtgg aggaaatgaa   120
tatgtaattg cgcctaatcc agatgaaaat ggaaaataca aaaaaaatac gagacaattt   180
tataatgatt tagcatatgg tatacaaggg aagtctataa cagatggaca aaatgggcat   240
ccttgggtac aaaataattg gcctacaggc aatcaagatc ggattaatgc actaggagaa   300
agatatacat tacaatacaa aggtagagct taa                                333

<210> SEQ ID NO 101
<211> LENGTH: 110
<212> TYPE: PRT
<213> ORGANISM: Bacillus thuringiensis

<400> SEQUENCE: 101

Ala Val Ser Gly Thr Ile Ile Ile Asn Asn Lys Asn Tyr Thr Phe Val
1               5                   10                  15

Glu Val Gln Tyr Ser Gln Ser Asp Pro Tyr Gly Leu Lys Arg Gly Ile
            20                  25                  30

Lys Phe Thr Gly Gly Gly Asn Glu Tyr Val Ile Ala Pro Asn Pro Asp
        35                  40                  45

Glu Asn Gly Lys Tyr Lys Asn Thr Arg Gln Phe Tyr Asn Asp Leu
    50                  55                  60

Ala Tyr Gly Ile Gln Gly Lys Ser Ile Thr Asp Gly Gln Asn Gly His
65              70                  75                  80

Pro Trp Val Gln Asn Asn Trp Pro Thr Gly Asn Gln Asp Arg Ile Asn
                85                  90                  95

Ala Leu Gly Glu Arg Tyr Thr Leu Gln Tyr Lys Gly Arg Ala
            100                 105                 110

<210> SEQ ID NO 102
<211> LENGTH: 348
<212> TYPE: DNA
<213> ORGANISM: Bacillus thuringiensis

<400> SEQUENCE: 102
gcagttagtg gaaatatata tgtaggtaga caacaagata ggtactcatt tgtagaaatt      60
cagtatactc agaatgatag ttcgggaaga cctaaaagag gaatcacatt tacatcagga    120
gcaattaagt atgatatatc ccctaatcct catttaagta agcatataa taataacgga     180 caacgagatt ttataatag cttagcatta aaagttcgtg attacgccac agatcataat    240
tgggttagag gtggttggga ttattctcag aaattaactt ttaatttaag tggatttagt    300
ggtagtgaag gtagtagata caccttgaca cctgtagcta aaacttaa                 348

<210> SEQ ID NO 103
<211> LENGTH: 115
<212> TYPE: PRT
<213> ORGANISM: Bacillus thuringiensis

<400> SEQUENCE: 103

Ala Val Ser Gly Asn Ile Tyr Val Gly Arg Gln Gln Asp Arg Tyr Ser
1               5                   10                  15

Phe Val Glu Ile Gln Tyr Thr Gln Asn Asp Ser Ser Gly Arg Pro Lys
            20                  25                  30

Arg Gly Ile Thr Phe Thr Ser Gly Ala Ile Lys Tyr Asp Ile Ser Pro
        35                  40                  45

Asn Pro His Leu Ser Lys Ala Tyr Asn Asn Gly Gln Arg Asp Phe
    50                  55                  60

Tyr Asn Ser Leu Ala Leu Lys Val Arg Asp Tyr Ala Thr Asp His Asn
65              70                  75                  80

Trp Val Arg Gly Gly Trp Asp Tyr Ser Gln Lys Leu Thr Phe Asn Leu
                85                  90                  95

Ser Gly Phe Ser Gly Ser Glu Gly Ser Arg Tyr Thr Leu Thr Pro Val
            100                 105                 110

Ala Lys Thr
        115

<210> SEQ ID NO 104
<211> LENGTH: 273

```
<212> TYPE: DNA
<213> ORGANISM: Bacillus thuringiensis

<400> SEQUENCE: 104
ggggtaagtg gctcaatcac gatcaacaaa gaaacatata aatatatcga agaatctttc      60
ggaaaaaatc gagggattac attcaaccca ggtcaacata cgtacaaaat aactccgaat     120
cctcacgaca atcccaaata caacaaaaaa caagagcagt tctatgagga aatcgcaaaa     180
ggcgttaaaa ctcttgtaga aaaatcaggc tggaaagata ctctcagcaa cattacagct     240
ctgggtgaaa cctatacatt agctccacgt taa                                  273

<210> SEQ ID NO 105
<211> LENGTH: 90
<212> TYPE: PRT
<213> ORGANISM: Bacillus thuringiensis

<400> SEQUENCE: 105

Gly Val Ser Gly Ser Ile Thr Ile Asn Lys Glu Thr Tyr Lys Tyr Ile
1               5                   10                  15

Glu Glu Ser Phe Gly Lys Asn Arg Gly Ile Thr Phe Asn Pro Gly Gln
                20                  25                  30

His Thr Tyr Lys Ile Thr Pro Asn Pro His Asp Asn Pro Lys Tyr Asn
            35                  40                  45

Lys Lys Gln Glu Gln Phe Tyr Glu Glu Ile Ala Lys Gly Val Lys Thr
        50                  55                  60

Leu Val Glu Lys Ser Gly Trp Lys Asp Thr Leu Ser Asn Ile Thr Ala
65                  70                  75                  80

Leu Gly Glu Thr Tyr Thr Leu Ala Pro Arg
                85                  90
```